US012735711B2

(12) United States Patent
Gomez-Ospina et al.

(10) Patent No.: US 12,735,711 B2
(45) Date of Patent: Sep. 15, 2026

(54) TARGETING THE HUMAN CCR5 LOCUS AS A SAFE HARBOR FOR THE EXPRESSION OF THERAPEUTIC PROTEINS

(71) Applicant: The Board of Trustees of the Leland Stanford Junior University, Stanford, CA (US)

(72) Inventors: Natalia Gomez-Ospina, Stanford, CA (US); Matthew H. Porteus, Stanford, CA (US); Samantha Glynne Scharenberg, Stanford, CA (US); Alvaro Amorin, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 787 days.

(21) Appl. No.: 18/010,773

(22) PCT Filed: Jun. 25, 2021

(86) PCT No.: PCT/US2021/039206
§ 371 (c)(1),
(2) Date: Dec. 15, 2022

(87) PCT Pub. No.: WO2021/263179
PCT Pub. Date: Dec. 30, 2021

(65) Prior Publication Data

US 2023/0265440 A1 Aug. 24, 2023

Related U.S. Application Data

(60) Provisional application No. 63/044,951, filed on Jun. 26, 2020.

(51) Int. Cl.

| | |
|---|---|
| ***C12N 15/63*** | (2006.01) |
| ***A61K 40/10*** | (2025.01) |
| ***A61K 40/40*** | (2025.01) |
| ***C12N 5/0786*** | (2010.01) |
| ***C12N 5/0789*** | (2010.01) |
| ***C12N 9/24*** | (2006.01) |
| ***C12N 15/113*** | (2010.01) |
| ***C12N 15/86*** | (2006.01) |

(52) U.S. Cl.
CPC .......... *C12N 15/1138* (2013.01); *A61K 40/10* (2025.01); *A61K 40/40* (2025.01); *C12N 5/0645* (2013.01); *C12N 5/0647* (2013.01); *C12N 9/24* (2013.01); *C12N 15/86* (2013.01); *C12Y 302/01076* (2013.01); *C12N 2310/321* (2013.01); *C12N 2510/00* (2013.01)

(58) Field of Classification Search
CPC ........................ C12N 15/63; C12Y 302/01076
See application file for complete search history.

(56) References Cited

U.S. PATENT DOCUMENTS

| | | | | |
|---|---|---|---|---|
| 9,757,420 B2 * | 9/2017 | Gregory et al. | A61K 35/28 |
| 2006/0182717 A1 | 8/2006 | Desmaris et al. | |
| 2011/0312029 A1 * | 12/2011 | Enenkel | C12P 21/00 435/69.1 |
| 2012/0308544 A1 * | 12/2012 | Steinfeld | A61K 38/48 424/94.3 |
| 2013/0045539 A1 * | 2/2013 | Delenda et al. | C12N 15/90 435/462 |
| 2014/0112896 A1 | 4/2014 | Rebar | |
| 2019/0032091 A1 | 1/2019 | Dever et al. | |
| 2019/0284533 A1 | 9/2019 | Bonner et al. | |

FOREIGN PATENT DOCUMENTS

| | | | | |
|---|---|---|---|---|
| WO | 2017/044776 A1 | | 3/2017 | |
| WO | WO2018195555 A1 | * | 10/2018 | C12N 15/86 |
| WO | 2019/165050 A1 | | 8/2019 | |
| WO | 2019/217803 A1 | | 11/2019 | |
| WO | 2020/006131 A2 | | 1/2020 | |
| WO | 2020/012149 A1 | | 1/2020 | |
| WO | WO2020227637 A1 | * | 11/2020 | C12N 15/90 |
| WO | 2021/097350 A1 | | 5/2021 | |
| WO | 2021/263179 A1 | | 12/2021 | |

OTHER PUBLICATIONS

Gomez-Ospina et al. (2019) "Human genome-edited hematopoietic stem cells phenotypically correct Mucopolysaccharidosis type I" Nature communications, 10:4045, 14 pages. (Year: 2019).*
Hendel et al. (2015) "Chemically modified guide RNAs enhance CRISPR-Cas genome editing in human primary cells" Nature biotechnology, 33(9), 985-989. (Year: 2015).*
Gomez-Ospina et al. (May 2018) "Engineering the Hematopoietic System for Lysosomal Storage Disorders: Correction of Mucopolysaccharidosis Type I Using Genome-Edited, Human Hematopoietic Stem and Progenitor Cells" In Molecular Therapy, vol. 26, No. 5S1, pp. 310-311, (Year: 2018), Abstract #673, 50 Hampshire St, Floor 5, Cambridge, MA 02139 USA: Cell Press. (Year: 2018).*
International Patent Application No. PCT/US2021/039206, International Preliminary Report on Patentability, Jan. 5, 2023, 12 pages.
International Patent Application No. PCT/US2021/039206, International Search Report and Written Opinion, Oct. 28, 2021, 16 pages.

* cited by examiner

*Primary Examiner* — James Joseph Graber
(74) *Attorney, Agent, or Firm* — Kilpatrick Townsend & Stockton LLP

(57) ABSTRACT

The present disclosure provides methods and compositions for treating lysosomal storage disorders in subjects, comprising genetically modifying cells from the subjects ex vivo by integrating therapeutic transgenes into the CCR5 locus.

13 Claims, 18 Drawing Sheets

Specification includes a Sequence Listing.

5′ - GCAGCATAGTGAGCCCAGAAGGG- 3′
sgRNA
CCR5
E1
E2
E3
E3
P
IDUA
P2
YFP
AAV6 DNA template
HR-GE
PGK
SFFV 0%
31%
33%
Mock
YFP
FSC-A
Count Targeted cells
CB
PB
% Targeted cells
RNP
AAV
SFFV -IDUA-YFP
PGK -IDUA-YFP
PGK-IDUA
80.0% Mono
17.6% Bi
2.5% WT/Indel
n = 400

Day = 0
Day = 30
YFP
FSC-A
31%
4%
65%
100%
98.7%
98.5%
78.4%
0.0%
1.7%
% YFP positive cells
YFP-high
YFP-low
YFP-negative
Days post-sort Fold IDUA activity
Media
Lysate
SFFV
PGK LAMP1 + area (um2)
MPSI
IDUA HSPCs CD34+ HSP C
HSPC-macrophages
% Positive cells
CD34+
CD14+
CD11b+
100 µm

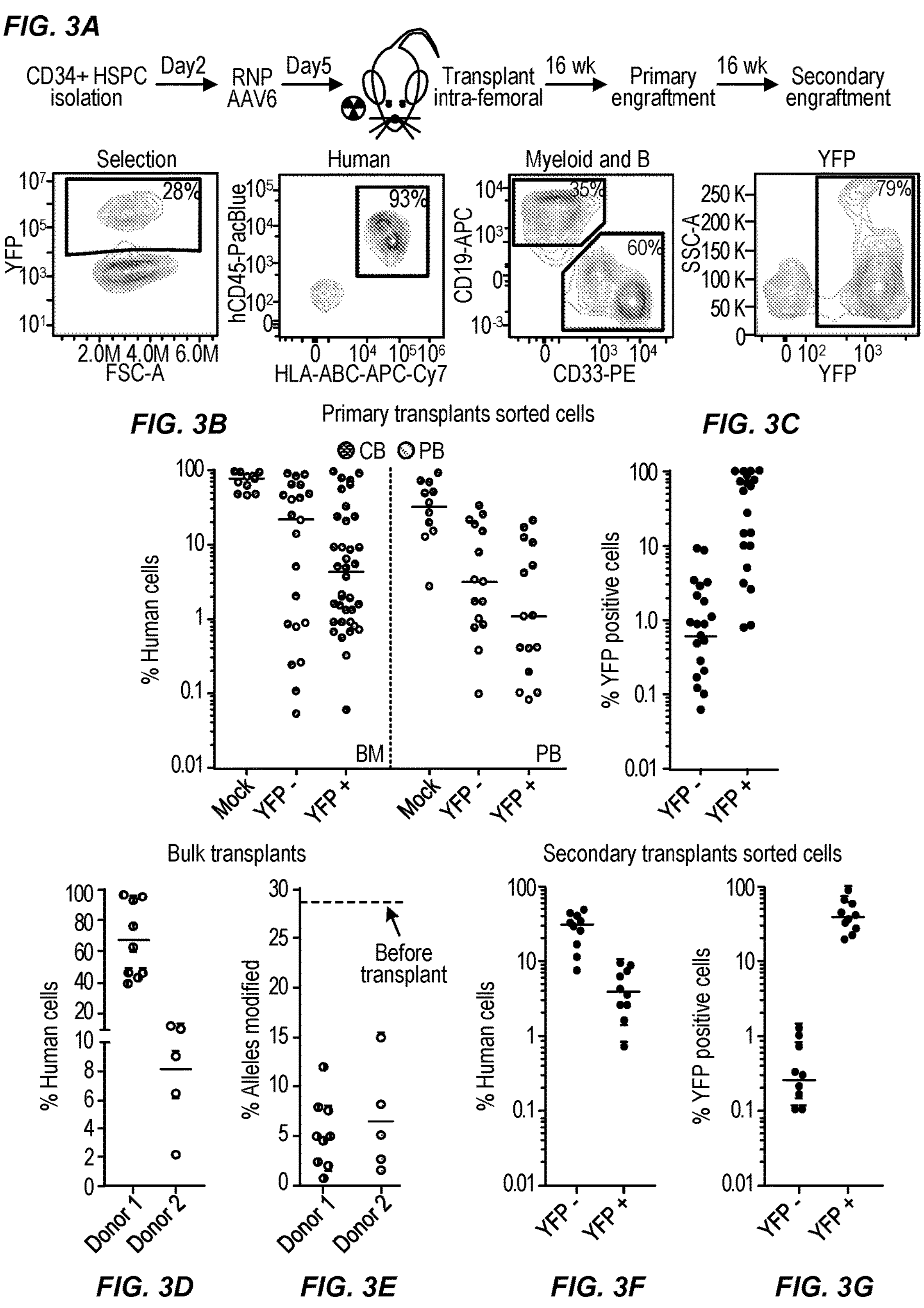
FIG. 3A
CD34+ HSPC isolation
Day2
RNP AAV6
Day5
Transplant intra-femoral
16 wk
Primary engraftment
16 wk
Secondary engraftment
Selection
Human
Myeloid and B
YFP
28%
93%
35%
60%
79%
YFP
FSC-A
hCD45-PacBlue
HLA-ABC-APC-Cy7
CD19-APC
CD33-PE
SSC-A
FIG. 3B
Primary transplants sorted cells
CB
PB
% Human cells
BM
PB
Mock
YFP -
YFP +
FIG. 3C
% YFP positive cells
Bulk transplants
% Human cells
Donor 1
Donor 2
% Alleles modified
Before transplant
Secondary transplants sorted cells
FIG. 3D
FIG. 3E
FIG. 3F
FIG. 3G BULK
SORT
SORT
% cells in BM
100
10
1
0.1
Human
Human
YFP+

BULK
n.s
****
****
Urine GAG (μg/mg)
1500
1250
1000
750
500
250
0
4 wks
8 wks
18 wks BULK
****
****
n.s
Fold GAG
5
4
3
2
1
0
Liver
Spleen
Brain
BULK
% IDUA activity
1000
100
10
1.0
0.1
Serum
Liver
Spleen
Brain SORTED
% IDUA activity
100
10
1
0.1
Serum
Liver
Spleen
Brain
W/X sham
W/X Tx
X/X sham
X/X Tx SORTED
****
****
****
Fold GAG
6
4
2
0
Urine
Liver
Spleen W/X sham
W/X Tx
X/X sham
X/X Tx BULK
Bone thickness (mm)
2.0
1.5
1.0
0.5
0.0
n.s.
****
Zygo
Skull
Femur SORTED
Bone thickness (mm)
2.5
2.0
1.5
1.0
0.5
0.0
***
**
n.s.
*
Zygo
Skull
Femur
W/X sham
X/X sham
X/X Tx
SORTED
W/X sham
X/X shame
X/X Tx
Ambulatory distance (m)
8
6
4
2
0
0 1 2 3 4 5 6 7 8 9 10

SORTED
W/X sham
X/X shame
X/X Tx
Vertical counts
50
40
30
20
10
0
0 1 2 3 4 5 6 7 8 9 10

% Alleles with indels
100
80
60
40
20
0
CB
PB

% Total indels
80
60
40
20
15
10
5
0
-30
-25
-20
-15
-10
-5
0
+5
Indel

Normalized to Mode
100
80
60
40
20
0
MFI:
43
225
RNP
MOCK
$10^{-2}$
0
$10^2$
$10^3$
CCR5
Mock sample
CCAAAGTCCCACTGGGCGGCAGCATAGTGAGCCCAGAAGGGGACAGTAAGAAGGAAAAACAGGTCA
CCR5 sgRNA + Cas9
CCAAAGTCCCACTGGGCGGCAGCATAGTGAGCCCAAGAAGGGGACAGTAAGAAGGAAAAACAGGTC

| Freq (%) | Indel | Sequence |
|---|---|---|
| 71.27 | +1bp | ATTGTATTTCCAAAGTCCCACTGGGCGGCAGCATAGTGAGCCCAAGAAGGGGACAGTAAGAAGGAAAAACAGGTCAGAG |
| 20.90 | 0 | ATTGTATTTCCAAAGTCCCACTGGGCGGCAGCATAGTGAGCCCA-GAAGGGGACAGTAAGAAGGAAAAACAGGTCAGAG |
| 0.78 | +2bp | ATTGTATTTCCAAAGTCCCACTGGGCGGCAGCATAGTGAGCCCAAAGAAGGGGACAGTAAGAAGGAAAAACAGGTCAGA |
| 0.68 | +1bp | ATTGTATTTCCAAAGTCCCACTGGGCGGCAGCATAGTGAGCCCACGAAGGGGACAGTAAGAAGGAAAAACAGGTCAGAG |
| 0.40 | -12bp | ATTGTATTTCCAAAGTCCCACTGGGCGGCAGCATA------------GGGGACAGTAAGAAGGAAAAACAGGTCAGAGA |
| 0.36 | -8bp | ATTGTATTTCCAAAGTCCCACTGGGCGGCAGCATAGTGA--------GGGGACAGTAAGAAGGAAAAACAGGTCAGAGA |
| 0.32 | -5bp | ATTGTATTTCCAAAGTCCCACTGGGCGGCAGCATAGTGA-----GAAGGGGACAGTAAGAAGGAAAAACAGGTCAGAGA |
| 0.30 | +1bp | ATTGTATTTCCAAAGTCCCACTGGGCGGCAGCATAGTGAGCCCCAGAAGGGGACAGTAAGAAGGAAAAACAGGTCAGAG |
| 0.29 | -7bp | ATTGTATTTCCAAAGTCCCACTGGGCGGCAGCATAGTG-------AAGGGGACAGTAAGAAGGAAAAACAGGTCAGAGA |
| 0.29 | -3bp | ATTGTATTTCCAAAGTCCCACTGGGCGGCAGCATAGTGAGCCCA---GGGGACAGTAAGAAGGAAAAACAGGTCAGAGA |
| 0.29 | -2bp | ATTGTATTTCCAAAGTCCCACTGGGCGGCAGCATAGTGAGCCCA--AGGGGACAGTAAGAAGGAAAAACAGGTCAGAGA |
| 0.25 | -9bp | ATTGTATTTCCAAAGTCCCACTGGGCGGCAGCATA---------GAAGGGGACAGTAAGAAGGAAAAACAGGTCAGAGA |
| 0.19 | +4bp | ATTGTATTTCCAAAGTCCCACTGGGCGGCAGCATAGTGAGCCCAGTAAGAAGGGGACAGTAAGAAGGAAAAACAGGTCA |
| 0.17 | -1bp | ATTGTATTTCCAAAGTCCCACTGGGCGGCAGCATAGTGAGCCCAG-AGGGGACAGTAAGAAGGAAAAACAGGTCAGAGA |
| 0.17 | +2bp | ATTGTATTTCCAAAGTCCCACTGGGCGGCAGCATAGTGAGCCCACAGAAGGGGACAGTAAGAAGGAAAAACAGGTCAGA |
| 0.17 | +1bp | ATTGTATTTCCAAAGTCCCACTGGGCGGCAGCATAGTGAGCCCAGTAAGGGGACAGTAAGAAGGAAAAACAGGTCAGAG |
| 0.15 | -10bp | ATTGTATTTCCAAAGTCCCACTGGGCGGCAGCATAGTGAGCCC----------AGTAAGAAGGAAAAACAGGTCAGAGA |
| 0.15 | +1bp | ATTGTATTTCCAAAGTCCCACTGGGCGGCAGCATAGTGAGCTCCAGAAGGGGACAGTAAGAAGGAAAAACAGGTCAGAG |
| 0.13 | +3bp | ATTGTATTTCCAAAGTCCCACTGGGCGGCAGCATAGTGAGCCCAGGAGAAGGGGACAGTAAGAAGGAAAAACAGGTCAG |
| 0.13 | +1bp | ATTGTATTTCCAAAGTCCCACTGGGCGGCAGCATAGTGAGCCGCAGAAGGGGACAGTAAGAAGGAAAAACAGGTCAGAG |
| 0.10 | -11bp | ATTGTATTTCCAAAGTCCCACTGGGCGGCAGCATAGTGAG-----------ACAGTAAGAAGGAAAAACAGGTCAGAGA |

*FIG. 7E*

*FIG. 8A*
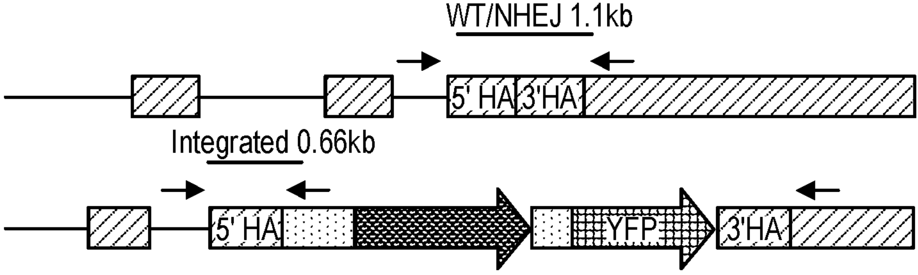
*FIG. 8B*
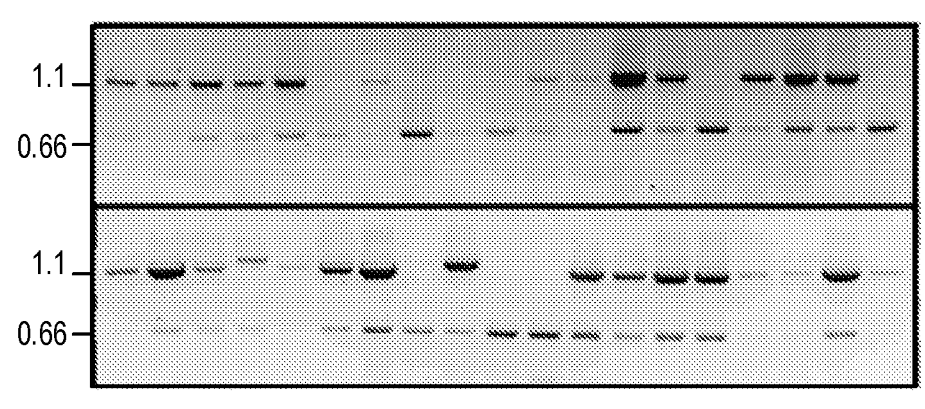
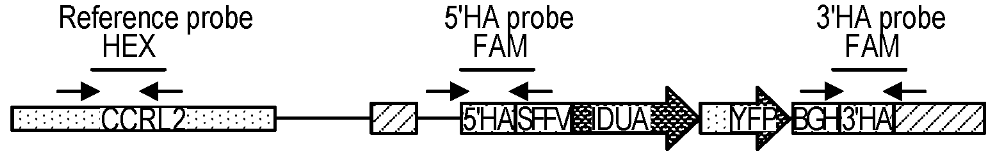
*FIG. 8C*
*FIG. 8D*
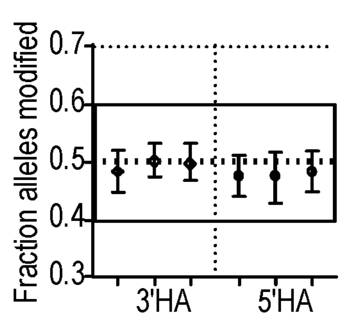
*FIG. 8E*
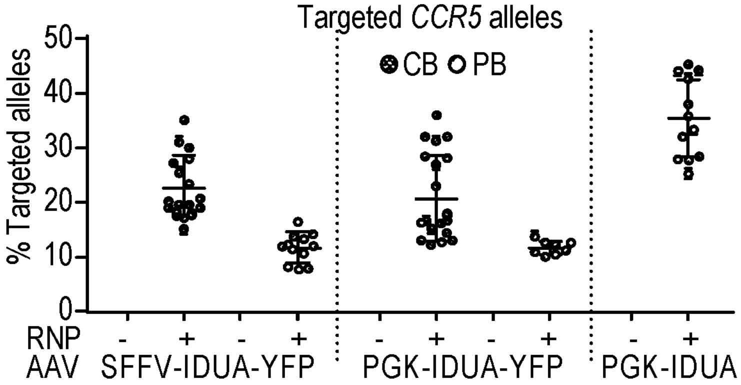

FIG. 11A
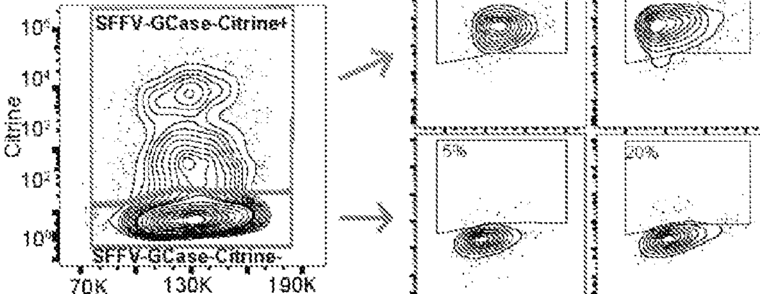
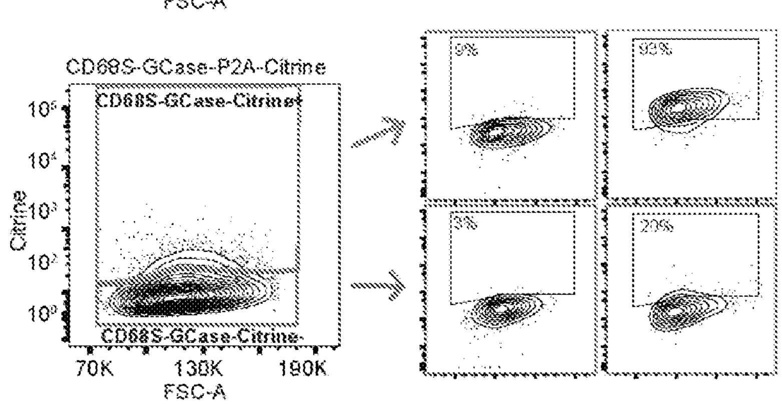
FIG. 11B
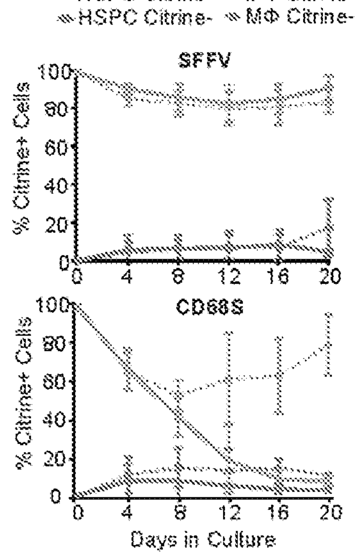
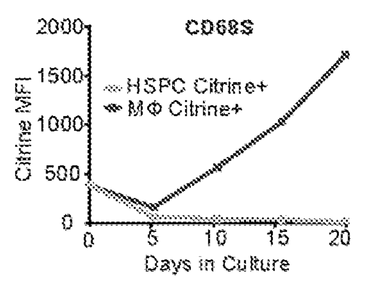
FIG. 11C
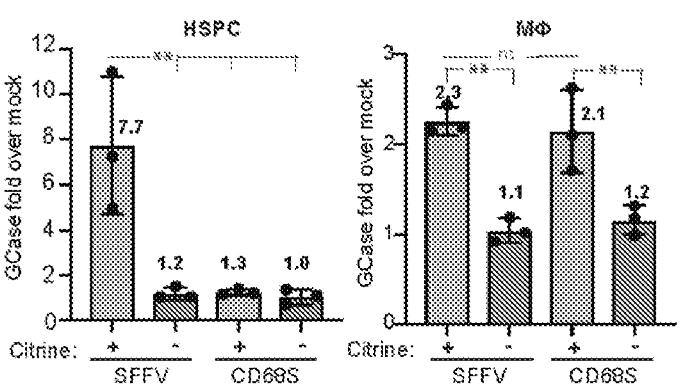
Sort HSPC MΦ
% Alleles Targeted
Citrine: + - + -
SFFV CD68S
FIG. 11D FIG. 11E FIG. 11F Total Colonies
100
80
60
40
20
0
Mock
SFFV-Citrine+
SFFV-Citrine-
CD68S-Citrine+
CD68S-Citrine- CFU-E BFU-E CFU-GM CFU-GEMM
% Colonies
100
75
50
25
0
Mock
SFFV-Citrine+
SFFV-Citrine-
CD68S-Citrine+
CD68S-Citrine- BONE MARROW
% Human Cells
100
10
1
0.1
Mock
CD68S-GCase
CD68S-GCase-P2A-Citrine SPLEEN
% Human Cells
100
10
1
0.1
Mock
CD68S-GCase
CD68S-GCase-P2A-Citrine

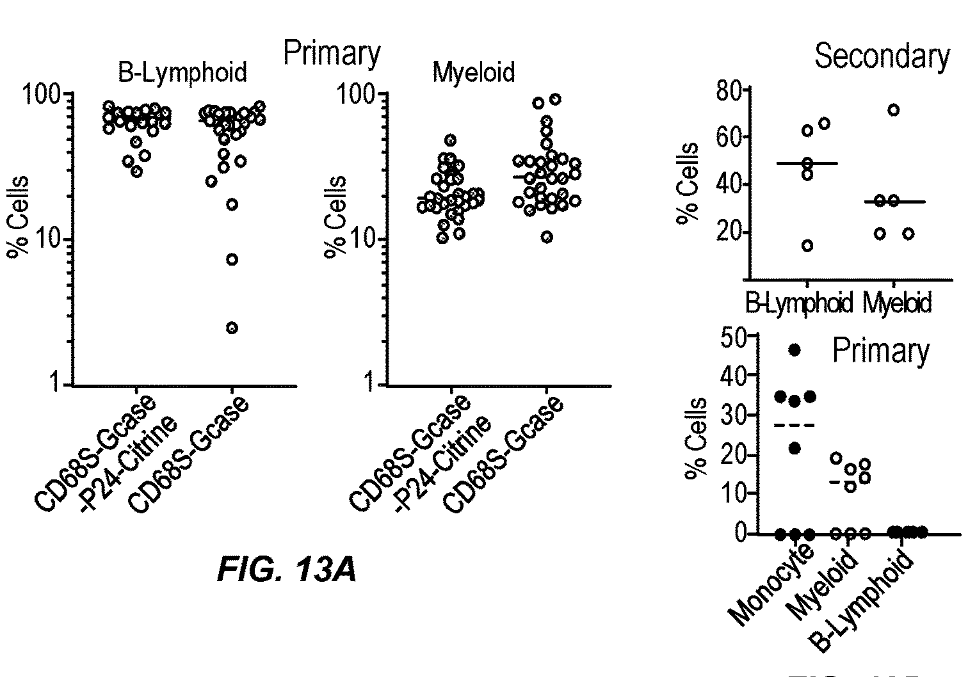
FIG. 13A
FIG. 13B
FIG. 13D
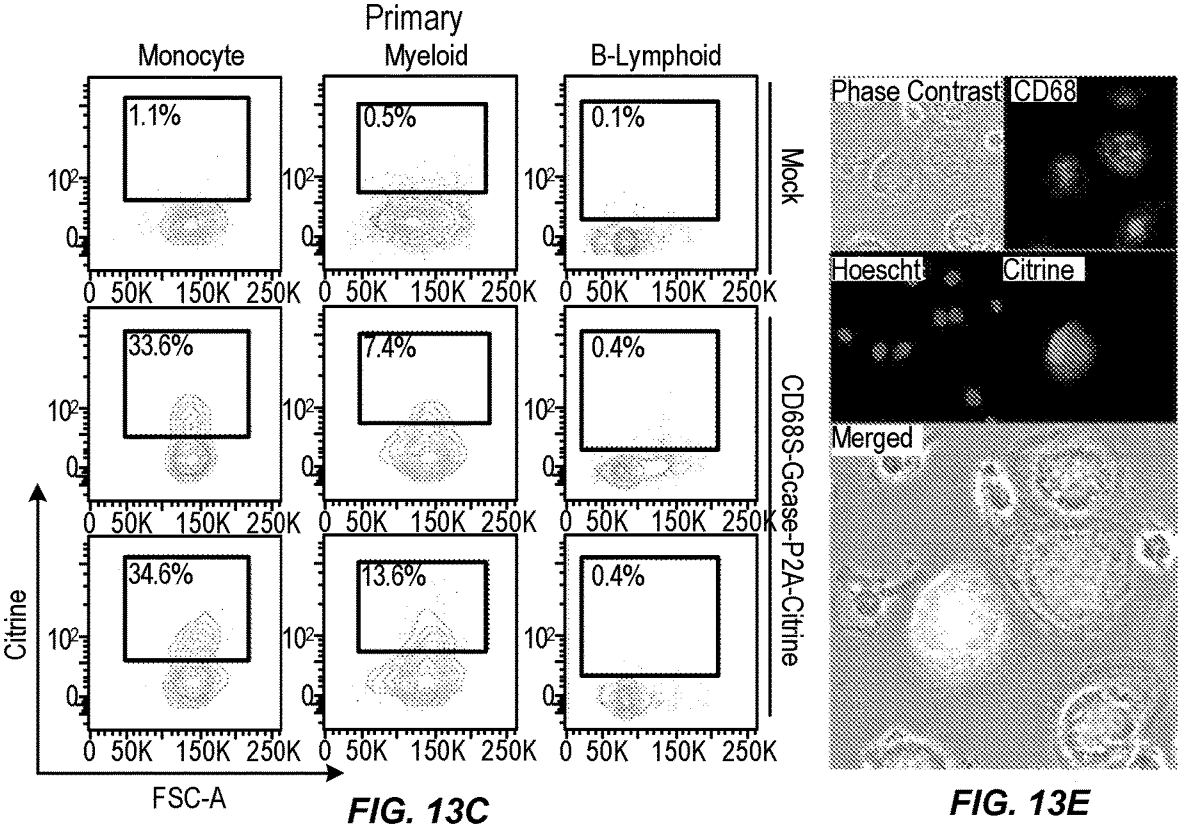
FIG. 13C
FIG. 13E

Lung
Peritoneal Macophages
Liver
SSC-A
Mouse CD45+/CD11b+
97%
99%
97%
CD11b-PE
mCD45-PE-Cy7
hCD45-PacBlue
27%
71%
62%
35%
65%
32%
Human CD45+/CD11b+
27%
26%
61%
Human CD45+/CD11b+/Citrine+
24%
15%
37%
Citrine hCD45+
hCD45+/Citrine+
% Human cells
Lung
Peritoneal Mϕ
Liver hCD45+CD11b+
hCD45+CD11b+/Citrine+

% Targeted Alleles
70
60
50
40
30
20
10
0
BM
Lung
Spleen
Liver
Peritoneal Mϕ
Citrine-
Citrine+

GCase Fold over mock
3.0
2.0
1.0
0
BM
SP
Lung

SEQUENCE LISTING

```
<160> NUMBER OF SEQ ID NOS: 52

<210> SEQ ID NO 1
<211> LENGTH: 500
<212> TYPE: DNA
<213> ORGANISM: Homo sapiens

<400> SEQUENCE: 1

tttcatgaat tcccccaaca gagccaagct ctccatctag tggacaggga agctagcagc     60

aaaccttccc ttcactacaa aacttcattg cttggccaaa aagagagtta attcaatgta    120

gacatctatg taggcaatta aaaacctatt gatgtataaa acagtttgca ttcatggagg    180

gcaactaaat acattctagg actttataaa agatcacttt ttatttatgc acagggtgga    240

acaagatgga ttatcaagtg tcaagtccaa tctatgacat caattattat acatcggagc    300

cctgccaaaa aatcaatgtg aagcaaatcg cagcccgcct cctgcctccg ctctactcac    360

tggtgttcat ctttggtttt gtgggcaaca tgctggtcat cctcatcctg ataaactgca    420

aaaggctgaa gagcatgact gacatctacc tgctcaacct ggccatctct gacctgtttt    480

tccttcttac tgtccccttc                                                 500


<210> SEQ ID NO 2
<211> LENGTH: 500
<212> TYPE: DNA
<213> ORGANISM: Homo sapiens

<400> SEQUENCE: 2

tgggctcact atgctgccgc ccagtgggac tttggaaata caatgtgtca actcttgaca     60

gggctctatt ttataggctt cttctctgga atcttcttca tcatcctcct gacaatcgat    120

aggtacctgg ctgtcgtcca tgctgtgttt gctttaaaag ccaggacggt cacctttggg    180

gtggtgacaa gtgtgatcac ttgggtggtg gctgtgtttg cgtctctccc aggaatcatc    240

tttaccagat ctcaaaaaga aggtcttcat tacacctgca gctctcattt tccatacagt    300

cagtatcaat tctggaagaa tttccagaca ttaaagatag tcatcttggg gctggtcctg    360

ccgctgcttg tcatggtcat ctgctactcg ggaatcctaa aaactctgct tcggtgtcga    420

aatgagaaga agaggcacag ggctgtgagg cttatcttca ccatcatgat tgtttatttt    480

ctcttctggg ctccctacaa                                                 500


<210> SEQ ID NO 3
<211> LENGTH: 23
<212> TYPE: DNA
<213> ORGANISM: Homo sapiens

<400> SEQUENCE: 3

gcagcatagt gagcccagaa ggg                                              23
```

<210> SEQ ID NO 4
<211> LENGTH: 20
<212> TYPE: DNA
<213> ORGANISM: Homo sapiens

<400> SEQUENCE: 4
gcagcatagt gagcccagaa 20

<210> SEQ ID NO 5
<211> LENGTH: 102
<212> TYPE: RNA
<213> ORGANISM: Artificial Sequence
<220> FEATURE:
<223> OTHER INFORMATION: Description of Artificial Sequence: Synthetic polynucleotide

<400> SEQUENCE: 5
gcagcauagu gagcccagaa guuuuagagc uagaaauagc aaguuaaaau aaggcuaguc 60
cguuaucaac uugaaaaagu ggcaccgagu cggugcuuuu uu 102

<210> SEQ ID NO 6
<211> LENGTH: 4599
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
tttcatgaat tcccccaaca gagccaagct ctccatctag tggacaggga agctagcagc 60
aaaccttccc ttcactacaa aacttcattg cttggccaaa aagagagtta attcaatgta 120
gacatctatg taggcaatta aaaacctatt gatgtataaa acagtttgca ttcatggagg 180
gcaactaaat acattctagg actttataaa agatcacttt ttatttatgc acagggtgga 240
acaagatgga ttatcaagtg tcaagtccaa tctatgacat caattattat acatcggagc 300
cctgccaaaa aatcaatgtg aagcaaatcg cagcccgcct cctgcctccg ctctactcac 360
tggtgttcat ctttggtttt gtgggcaaca tgctggtcat cctcatcctg ataaactgca 420
aaaggctgaa gagcatgact gacatctacc tgctcaacct ggccatctct gacctgtttt 480
tccttcttac tgtccccttc tctagatacc gggtagggga ggcgcttttc ccaaggcagt 540
ctggagcatg cgctttagca gccccgctgg gcacttggcg ctacacaagt ggcctctggc 600
ctcgcacaca ttccacatcc accggtaggc gccaaccggc tccgttcttt ggtggcccct 660
tcgcgccacc ttctactcct cccctagtca ggaagttccc ccccgccccg cagctcgcgt 720
cgtgcaggac gtgacaaatg gaagtagcac gtctcactag tctcgtgcag atggacagca 780
ccgctgagca atggaagcgg gtaggccttt ggggcagcgg ccaatagcag ctttgctcct 840
tcgctttctg ggctcagagg ctgggaaggg gtgggtccgg gggcgggctc aggggcgggc 900
tcaggggcgg ggcgggcgcc cgaaggtcct ccggaggccc ggcattctgc acgcttcaaa 960
agcgcacgtc tgccgcgctg ttctcctctt cctcaggatc catgcgtccc ctgcgccccc 1020
gcgccgcgct gctggcgctc ctggcctcgc tcctggccgc gcccccggtg gccccggccg 1080
aggccccgca cctggtgcat gtggacgcgg cccgcgcgct gtggcccctg cggcgcttct 1140
ggaggagcac aggcttctgc ccccgctgc cacacagcca ggctgaccag tacgtcctca 1200
gctgggacca gcagctcaac ctcgcctatg tgggcgccgt ccctcaccgc ggcatcaagc 1260
aggtccggac ccactggctg ctggagcttg tcaccaccag gggtccact ggacggggcc 1320

```
tgagctacaa cttcacccac ctggacgggt acctggacct tctcagggag aaccagctcc   1380
tcccagggtt tgagctgatg ggcagcgcct cgggccactt cactgacttt gaggacaagc   1440
agcaggtgtt tgagtggaag gacttggtct ccagcctggc caggagatac atcggtaggt   1500
acggactggc gcatgtttcc aagtggaact tcgagacgtg gaatgagcca gaccaccacg   1560
actttgacaa cgtctccatg accatgcaag gcttcctgaa ctactacgat gcctgctcgg   1620
agggtctgcg cgccgccagc cccgccctgc ggctgggagg ccccggcgac tccttccaca   1680
ccccaccgcg atccccgctg agctggggcc tcctgcgcca ctgccacgac ggtaccaact   1740
tcttcactgg ggaggcgggc gtgcggctgg actacatctc cctccacagg aagggtgcgc   1800
gcagctccat ctccatcctg gagcaggaga aggtcgtcgc gcagcagatc cggcagctct   1860
tccccaagtt cgcggacacc cccatttaca acgacgaggc ggacccgctg gtgggctggt   1920
ccctgccaca gccgtggagg gcggacgtga cctacgcggc catggtggtg aaggtcatcg   1980
cgcagcatca gaacctgcta ctggccaaca ccacctccgc cttcccctac gcgctcctga   2040
gcaacgacaa tgccttcctg agctaccacc cgcacccctt cgcgcagcgc acgctcaccg   2100
cgcgcttcca ggtcaacaac acccgcccgc cgcacgtgca gctgttgcgc aagccggtgc   2160
tcacggccat ggggctgctg gcgctgctgg atgaggagca gctctgggcc gaagtgtcgc   2220
aggccgggac cgtcctggac agcaaccaca cggtgggcgt cctggccagc gcccaccgcc   2280
cccagggccc ggccgacgcc tggcgcgccg cggtgctgat ctacgcgagc gacgacaccc   2340
gcgcccaccc caaccgcagc gtcgcggtga ccctgcggct gcgcggggtg ccccccggcc   2400
cgggcctggt ctacgtcacg cgctacctgg acaacgggct ctgcagcccc gacggcgagt   2460
ggcggcgcct gggccggccc gtcttcccca cggcagagca gttccggcgc atgcgcgcgg   2520
ctgaggaccc ggtggccgcg gcgcccccgcc ccttacccgc cggcggccgc ctgaccctca   2580
gacctgcact tagattgcct tccctttgt tggtccacgt ttgcgctagg cccgagaaac   2640
cgccaggaca agtaacacgg cttcgggcgc tgccacttac tcaggggcag ctggtgctgg   2700
tttggtcaga cgagcatgtc ggaagcaaat gcctttggac ctacgagata caattttcac   2760
aggatggtaa ggcttacact ccggtctcaa gaaagcccag tacctttaac ctttttgtgt   2820
tcagtccaga tactggagca gtaagcggtt catatagagt cagagcgctg gattactggg   2880
ccaggcccgg acctttctca gatccggtcc cctacctgga agttcccgtg ccgcggggtc   2940
ctccatcacc aggcaaccca ggaagcggag ctactaactt cagcctgctg aagcaggctg   3000
gagacgtgga ggagaaccct ggacctgggg caggtgccac cggccgcgcc atggacgggc   3060
cgcgcctgct gctgttgctg cttctggggg tgtcccttgg aggtgccaag gaggcatgcc   3120
ccacaggcct gtacacacac agcggtgagt gctgcaaagc ctgcaacctg ggcgagggtg   3180
tggcccagcc ttgtggagcc aaccagaccg tgtgtgagcc ctgcctggac agcgtgacgt   3240
tctccgacgt ggtgagcgcg accgagccgt gcaagccgtg caccgagtgc gtggggctcc   3300
agagcatgtc ggcgccatgc gtggaggccg acgacgccgt gtgccgctgc gcctacggct   3360
actaccagga tgagacgact gggcgctgcg aggcgtgccg cgtgtgcgag gcgggctcgg   3420
gcctcgtgtt ctcctgccag gacaagcaga acaccgtgtg cgaggagtgc cccgacggca   3480
cgtattccga cgaggccaac cacgtggacc cgtgcctgcc ctgcaccgtg tgcgaggaca   3540
ccgagcgcca gctccgcgag tgcacacgct gggccgacgc cgagtgcgag gagatccctg   3600
gccgttggat tacacggtcc acacccccag agggctcgga cagcacagcc cccagcaccc   3660
```

```
aggagcctga ggcacctcca gaacaagacc tcatagccag cacggtggcg ggtgtggtga   3720

ccacagtgat gggcagctcc cagcccgtgg tgacccgagg caccaccgac aacctcatcc   3780

ctgtctattg ctccatcctg gctgctgtgg ttgtgggtct tgtggcctac atagccttca   3840

agaggtaata actcgagccg ctgatcagcc tcgactgtgc cttctagttg ccagccatct   3900

gttgtttgcc cctcccccgt gccttccttg accctggaag gtgccactcc cactgtcctt   3960

tcctaataaa atgaggaaat tgcatcgcat tgtctgagta ggtgtcattc tattctgggg   4020

ggtggggtgg ggcaggacag caagggggag gattgggaag acaatagcag gcatgctggg   4080

gatgcggtgg gctactagtt gggctcacta tgctgccgcc cagtgggact ttggaaatac   4140

aatgtgtcaa ctcttgacag ggctctattt tataggcttc ttctctggaa tcttcttcat   4200

catcctcctg acaatcgata ggtacctggc tgtcgtccat gctgtgtttg ctttaaaagc   4260

caggacggtc acctttgggg tggtgacaag tgtgatcact tgggtggtgg ctgtgtttgc   4320

gtctctccca ggaatcatct ttaccagatc tcaaaaagaa ggtcttcatt acacctgcag   4380

ctctcatttt ccatacagtc agtatcaatt ctggaagaat ttccagacat taaagatagt   4440

catcttgggg ctggtcctgc cgctgcttgt catggtcatc tgctactcgg gaatcctaaa   4500

aactctgctt cggtgtcgaa atgagaagaa gaggcacagg gctgtgaggc ttatcttcac   4560

catcatgatt gtttattttc tcttctgggc tccctacaa                          4599
```

<210> SEQ ID NO 7
<211> LENGTH: 3711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
tttcatgaat tcccccaaca gagccaagct ctccatctag tggacaggga agctagcagc     60

aaaccttccc ttcactacaa aacttcattg cttggccaaa aagagagtta attcaatgta    120

gacatctatg taggcaatta aaaacctatt gatgtataaa acagtttgca ttcatggagg    180

gcaactaaat acattctagg actttataaa agatcacttt ttatttatgc acagggtgga    240

acaagatgga ttatcaagtg tcaagtccaa tctatgacat caattattat acatcggagc    300

cctgccaaaa aatcaatgtg aagcaaatcg cagcccgcct cctgcctccg ctctactcac    360

tggtgttcat ctttggtttt gtgggcaaca tgctggtcat cctcatcctg ataaactgca    420

aaaggctgaa gagcatgact gacatctacc tgctcaacct ggccatctct gacctgtttt    480

tccttcttac tgtccccttc tctagatacc gggtagggga ggcgcttttc ccaaggcagt    540

ctggagcatg cgctttagca gccccgctgg gcacttggcg ctacacaagt ggcctctggc    600

ctcgcacaca ttccacatcc accggtaggc gccaaccggc tccgttcttt ggtggcccct    660

tcgcgccacc ttctactcct cccctagtca ggaagttccc cccgccccg cagctcgcgt    720

cgtgcaggac gtgacaaatg gaagtagcac gtctcactag tctcgtgcag atggacagca    780

ccgctgagca atggaagcgg gtaggccttt ggggcagcgg ccaatagcag ctttgctcct    840

tcgctttctg ggctcagagg ctgggaaggg gtgggtccgg gggcgggctc aggggcgggc    900

tcaggggcgg ggcgggcgcc cgaaggtcct ccggaggccc ggcattctgc acgcttcaaa    960

agcgcacgtc tgccgcgctg ttctcctctt cctcaggatc catgcgtccc ctgcgccccc   1020

gcgccgcgct gctggcgctc ctggcctcgc tcctggccgc gcccccggtg gccccggccg   1080
```

-continued

```
aggccccgca cctggtgcat gtggacgcgg cccgcgcgct gtggccoctg cggcgcttct   1140
ggaggagcac aggcttctgc cccccgctgc cacacagcca ggctgaccag tacgtcctca   1200
gctgggacca gcagctcaac ctcgcctatg tgggcgccgt ccctcaccgc ggcatcaagc   1260
aggtccggac ccactggctg ctggagcttg tcaccaccag gggtccact ggacggggcc   1320
tgagctacaa cttcacccac ctggacgggt acctggacct tctcagggag aaccagctcc   1380
tcccagggtt tgagctgatg ggcagcgcct cgggccactt cactgacttt gaggacaagc   1440
agcaggtgtt tgagtggaag gacttggtct ccagcctggc caggagatac atcggtaggt   1500
acggactggc gcatgtttcc aagtggaact tcgagacgtg gaatgagcca gaccaccacg   1560
actttgacaa cgtctccatg accatgcaag gcttcctgaa ctactacgat gcctgctcgg   1620
agggtctgcg cgccgccagc cccgccctgc ggctgggagg ccccggcgac tccttccaca   1680
ccccaccgcg atccccgctg agctggggcc tcctgcgcca ctgccacgac ggtaccaact   1740
tcttcactgg ggaggcgggc gtgcggctgg actacatctc cctccacagg aagggtgcgc   1800
gcagctccat ctccatcctg gagcaggaga aggtcgtcgc gcagcagatc cggcagctct   1860
tccccaagtt cgcggacacc cccatttaca acgacgaggc ggacccgctg gtgggctggt   1920
ccctgccaca gccgtggagg gcggacgtga cctacgcggc catggtggtg aaggtcatcg   1980
cgcagcatca gaacctgcta ctggccaaca ccacctccgc cttcccctac gcgctcctga   2040
gcaacgacaa tgccttcctg agctaccacc cgcacccctt cgcgcagcgc acgctcaccg   2100
cgcgcttcca ggtcaacaac acccgcccgc cgcacgtgca gctgttgcgc aagccggtgc   2160
tcacggccat ggggctgctg gcgctgctgg atgaggagca gctctgggcc gaagtgtcgc   2220
aggccgggac cgtcctggac agcaaccaca cggtgggcgt cctggccagc gcccaccgcc   2280
cccagggccc ggccgacgcc tggcgcgccg cggtgctgat ctacgcgagc gacgacaccc   2340
gcgcccaccc caaccgcagc gtcgcggtga ccctgcggct gcgcggggtg ccccccggcc   2400
cgggcctggt ctacgtcacg cgctacctgg acaacgggct ctgcagcccc gacggcgagt   2460
ggcggcgcct gggccggccc gtcttcccca cggcagagca gttccggcgc atgcgcgcgg   2520
ctgaggaccc ggtggccgcg gcgccccgcc ccttacccgc cggcggccgc ctgaccctgc   2580
gccccgcgct gcggctgccg tcgcttttgc tggtgcacgt gtgtgcgcgc cccgagaagc   2640
cgcccgggca ggtcacgcgg ctccgcgccc tgcccctgac ccaagggcag ctggttctgg   2700
tctggtcgga tgaacacgtg ggctccaagt gcctgtggac atacgagatc cagttctctc   2760
aggacggtaa ggcgtacacc ccggtcagca ggaagccatc gaccttcaac ctctttgtgt   2820
tcagcccaga cacaggtgct gtctctggct cctaccgagt tcgagccctg gactactggg   2880
cccgaccagg ccccttctcg gaccctgtgc cgtacctgga ggtccctgtg ccaagagggc   2940
ccccatcccc gggcaatcca tagctcgagc cgctgatcag cctcgactgt gccttctagt   3000
tgccagccat ctgttgtttg cccctccccc gtgccttcct tgaccctgga aggtgccact   3060
cccactgtcc tttcctaata aaatgaggaa attgcatcgc attgtctgag taggtgtcat   3120
tctattctgg ggggtggggt ggggcaggac agcaaggggg aggattggga agacaatagc   3180
aggcatgctg gggatgcggt gggctactag ttgggctcac tatgctgccg cccagtggga   3240
ctttggaaat acaatgtgtc aactcttgac agggctctat tttataggct tcttctctgg   3300
aatcttcttc atcatcctcc tgacaatcga taggtacctg gctgtcgtcc atgctgtgtt   3360
tgctttaaaa gccaggacgg tcacctttgg ggtggtgaca agtgtgatca cttgggtggt   3420
ggctgtgttt gcgtctctcc caggaatcat ctttaccaga tctcaaaaag aaggtcttca   3480
```

```
ttacacctgc agctctcatt ttccatacag tcagtatcaa ttctggaaga atttccagac   3540

attaaagata gtcatcttgg ggctggtcct gccgctgctt gtcatggtca tctgctactc   3600

gggaatccta aaaactctgc ttcggtgtcg aaatgagaag aagaggcaca gggctgtgag   3660

gcttatcttc accatcatga ttgtttattt tctcttctgg gctccctaca a            3711
```

<210> SEQ ID NO 8
<211> LENGTH: 3340
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
tttcatgaat tcccccaaca gagccaagct ctccatctag tggacaggga agctagcagc     60

aaaccttccc ttcactacaa aacttcattg cttggccaaa aagagagtta attcaatgta    120

gacatctatg taggcaatta aaaacctatt gatgtataaa acagtttgca ttcatggagg    180

gcaactaaat acattctagg actttataaa agatcacttt ttatttatgc acagggtgga    240

acaagatgga ttatcaagtg tcaagtccaa tctatgacat caattattat acatcggagc    300

cctgccaaaa aatcaatgtg aagcaaatcg cagcccgcct cctgcctccg ctctactcac    360

tggtgttcat ctttggtttt gtgggcaaca tgctggtcat cctcatcctg ataaactgca    420

aaaggctgaa gagcatgact gacatctacc tgctcaacct ggccatctct gacctgtttt    480

tccttcttac tgtccccttc tctagactgt tcccatagct acttgccaca actgccaagc    540

aagtttcgct gagtttgaca catggatccc tgtggatcaa ctgccctagg actccgtttg    600

cacccatgtg acactgttga ctttgccctg acgaagcagg gccaacagtc ccctaactta    660

attacaaaaa ctaatgacta agagagaggt ggctagagct gaggcccctg agtcaggctg    720

tgggtgggat catctccagt acaggaagtg agactttcat ttcctccttt ccaagagagg    780

gctgagggag cagggttgag caactggtgc agacagccta gctggacttt gggtgaggcg    840

gttcagccat atcgaattct gctggggcta ctggcaggta aggaggaagg aggctgaggg    900

gagggggccc ctgggaggga gcctgccctg ggttgctaac catctcctct ctgccaaaag    960

cccaggggat tcgaaggatc catggagttt tcaagtcctt ccagagagga atgtcccaag   1020

cctttgagta gggtaagcat catggctggc agcctcacag gattgcttct acttcaggca   1080

gtgtcgtggg catcaggtgc ccgcccctgc atccctaaaa gcttcggcta cagctcggtg   1140

gtgtgtgtct gcaatgccac atactgtgac tcctttgacc ccccgacctt tcctgccctt   1200

ggtaccttca gccgctatga gagtacacgc agtgggcgac ggatggagct gagtatgggg   1260

cccatccagg ctaatcacac gggcacaggc ctgctactga ccctgcagcc agaacagaag   1320

ttccagaaag tgaagggatt tggaggggcc atgacagatg ctgctgctct caacatcctt   1380

gccctgtcac cccctgccca aaatttgcta cttaaatcgt acttctctga agaaggaatc   1440

ggatataaca tcatccgggt acccatggcc agctgtgact tctccatccg cacctacacc   1500

tatgcagaca cccctgatga tttccagttg cacaacttca gcctcccaga ggaagatacc   1560

aagctcaaga taccccctgat tcaccgagcc ctgcagttgg cccagcgtcc cgtttcactc   1620

cttgccagcc cctggacatc acccacttgg ctcaagacca atggagcggt gaatgggaag   1680

gggtcactca agggacagcc cggagacatc taccaccaga cctgggccag atactttgtg   1740

aagttcctgg atgcctatgc tgagcacaag ttacagttct gggcagtgac agctgaaaat   1800
```

```
gagccttctg ctgggctgtt gagtggatac cccttccagt gcctgggctt caccccctgaa  1860

catcagcgag acttcattgc ccgtgaccta ggtcctaccc tcgccaacag tactcaccac  1920

aatgtccgcc tactcatgct ggatgaccaa cgcttgctgc tgccccactg ggcaaaggtg  1980

gtactgacag acccagaagc agctaaatat gttcatggca ttgctgtaca ttggtacctg  2040

gactttctgg ctccagccaa agccacccta ggggagacac accgcctgtt ccccaacacc  2100

atgctctttg cctcagaggc ctgtgtgggc tccaagttct gggagcagag tgtgcggcta  2160

ggctcctggg atcgagggat gcagtacagc cacagcatca tcacgaacct cctgtaccat  2220

gtggtcggct ggaccgactg gaaccttgcc ctgaaccccg aaggaggacc caattgggtg  2280

cgtaactttg tcgacagtcc catcattgta gacatcacca aggacacgtt ttacaaacag  2340

cccatgttct accaccttgg ccacttcagc aagttcattc ctgagggctc ccagagagtg  2400

gggctggttg ccagtcagaa gaacgacctg gacgcagtgg cactgatgca tcccgatggc  2460

tctgctgttg tggtcgtgct aaaccgctcc tctaaggatg tgcctcttac catcaaggat  2520

cctgctgtgg gcttcctgga gacaatctca cctggctact ccattcacac ctacctgtgg  2580

cgtcgccagt agctcgagcc gctgatcagc ctcgactgtg ccttctagtt gccagccatc  2640

tgttgtttgc ccctcccccg tgccttcctt gaccctggaa ggtgccactc ccactgtcct  2700

ttcctaataa aatgaggaaa ttgcatcgca ttgtctgagt aggtgtcatt ctattctggg  2760

gggtggggtg gggcaggaca gcaaggggga ggattgggaa gacaatagca ggcatgctgg  2820

ggatgcggtg ggctactagt tgggctcact atgctgccgc ccagtgggac tttggaaata  2880

caatgtgtca actcttgaca gggctctatt ttataggctt cttctctgga atcttcttca  2940

tcatcctcct gacaatcgat aggtacctgg ctgtcgtcca tgctgtgttt gctttaaaag  3000

ccaggacggt cacctttggg gtggtgacaa gtgtgatcac ttgggtggtg gctgtgtttg  3060

cgtctctccc aggaatcatc tttaccagat ctcaaaaaga aggtcttcat tacacctgca  3120

gctctcattt tccatacagt cagtatcaat tctggaagaa tttccagaca ttaaagatag  3180

tcatcttggg gctggtcctg ccgctgcttg tcatggtcat ctgctactcg ggaatcctaa  3240

aaactctgct tcggtgtcga aatgagaaga agaggcacag ggctgtgagg cttatcttca  3300

ccatcatgat tgtttatttt ctcttctggg ctccctacaa                        3340
```

<210> SEQ ID NO 9
<211> LENGTH: 23
<212> TYPE: DNA
<213> ORGANISM: Unknown
<220> FEATURE:
<223> OTHER INFORMATION: Description of Unknown:
      off-target seqeunce

<400> SEQUENCE: 9

```
acagaataga gagcccagaa agg                                            23
```

<210> SEQ ID NO 10
<211> LENGTH: 23
<212> TYPE: DNA
<213> ORGANISM: Unknown
<220> FEATURE:
<223> OTHER INFORMATION: Description of Unknown:
      off-target seqeunce

<400> SEQUENCE: 10

```
acagcataga gggcccagaa ggg                                            23
```

<210> SEQ ID NO 11
<211> LENGTH: 23
<212> TYPE: DNA
<213> ORGANISM: Unknown
<220> FEATURE:
<223> OTHER INFORMATION: Description of Unknown:
off-target seqeunce

<400> SEQUENCE: 11
acagcatagt gaacccagga ggg 23

<210> SEQ ID NO 12
<211> LENGTH: 23
<212> TYPE: DNA
<213> ORGANISM: Unknown
<220> FEATURE:
<223> OTHER INFORMATION: Description of Unknown:
off-target seqeunce

<400> SEQUENCE: 12
gctgcatagt gaacccagta tgg 23

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13
gggaggattg ggaagaca 18

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
aggtgttcag gagaaggaca 20

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
probe

<400> SEQUENCE: 15
gctggggatg cggtgg 16

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 16
cctcctggct gagaaaaag 19

```
<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

gctgtatgaa tccaggtcc                                                    19


<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18

caggataagg cagctgt                                                      17


<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

caccatgctt gacccagttt                                                   20


<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

cgcattgtct gagtaggtgt                                                   20


<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21

ttatagatgg agaacaactc                                                   20


<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22

gttggacagc aatcatacag                                                   20


<210> SEQ ID NO 23
```

<211> LENGTH: 200
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 23
ggtgggagct agatattagg gtaggaagcc agatgctagg tatgagagag ccaacagcct 60
cagccctctg cttggcttat agatggagaa caactctagg cagaggtctc aaaggctggg 120
gctgtgttgg acagcaatca tacagtgggt gtcctggcca gcacccatca ccctgaaggc 180
tccgcagcgg cctggagtac 200

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
catggccctg ttgggtgagt aatga 25

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
tgtggtactc caggccgctg 20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
ggaaccccta gtgatggagt t 21

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
cggcctcagt gagcga 16

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic probe

<400> SEQUENCE: 28
tctgcgcgct cg 12

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gctgtatgaa ctcaggtcc 19

<210> SEQ ID NO 30
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 30
ccaaagtccc actgggcggc agcatagtga gcccagaagg ggacagtaag aaggaaaaac 60
aggtca 66

<210> SEQ ID NO 31
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 31
ccaaagtccc actgggcggc agcatagtga gcccaagaag ggacagtaa gaaggaaaaa 60 caggtc 66

<210> SEQ ID NO 32
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
attgtatttc caaagtccca ctgggcggca gcatagtgag cccaagaagg ggacagtaag 60
aaggaaaaac aggtcagag 79

<210> SEQ ID NO 33
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
attgtatttc caaagtccca ctgggcggca gcatagtgag cccagaaggg gacagtaaga 60
aggaaaaaca ggtcagag 78

<210> SEQ ID NO 34
<211> LENGTH: 79

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34

attgtatttc caaagtccca ctgggcggca gcatagtgag cccaaagaag gggacagtaa     60

gaaggaaaaa caggtcaga                                                  79


<210> SEQ ID NO 35
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35

attgtatttc caaagtccca ctgggcggca gcatagtgag cccacgaagg ggacagtaag     60

aaggaaaaac aggtcagag                                                  79


<210> SEQ ID NO 36
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36

attgtatttc caaagtccca ctgggcggca gcatagggga cagtaagaag gaaaaacagg     60

tcagaga                                                               67


<210> SEQ ID NO 37
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

attgtatttc caaagtccca ctgggcggca gcatagtgag gggacagtaa gaaggaaaaa     60

caggtcagag a                                                          71


<210> SEQ ID NO 38
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

attgtatttc caaagtccca ctgggcggca gcatagtgag aaggggacag taagaaggaa     60

aaacaggtca gaga                                                       74


<210> SEQ ID NO 39
<211> LENGTH: 79
<212> TYPE: DNA
<213> ORGANISM: Artificial Sequence
<220> FEATURE:
<223> OTHER INFORMATION: Description of Artificial Sequence: Synthetic
```

oligonucleotide

<400> SEQUENCE: 39
attgtatttc caaagtccca ctgggcggca gcatagtgag ccccagaagg ggacagtaag 60
aaggaaaaac aggtcagag 79

<210> SEQ ID NO 40
<211> LENGTH: 72
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
attgtatttc caaagtccca ctgggcggca gcatagtgaa ggggacagta agaaggaaaa 60
acaggtcaga ga 72

<210> SEQ ID NO 41
<211> LENGTH: 76
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
attgtatttc caaagtccca ctgggcggca gcatagtgag cccaggggac agtaagaagg 60
aaaaacaggt cagaga 76

<210> SEQ ID NO 42
<211> LENGTH: 77
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
attgtatttc caaagtccca ctgggcggca gcatagtgag cccaagggga cagtaagaag 60
gaaaaacagg tcagaga 77

<210> SEQ ID NO 43
<211> LENGTH: 70
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
attgtatttc caaagtccca ctgggcggca gcatagaagg ggacagtaag aaggaaaaac 60
aggtcagaga 70

<210> SEQ ID NO 44
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44

```
attgtatttc caaagtccca ctgggcggca gcatagtgag cccagtaaga aggggacagt     60

aagaaggaaa aacaggtca                                                  79


<210> SEQ ID NO 45
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

attgtatttc caaagtccca ctgggcggca gcatagtgag cccagagggg acagtaagaa     60

ggaaaaacag gtcagaga                                                   78


<210> SEQ ID NO 46
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

attgtatttc caaagtccca ctgggcggca gcatagtgag cccacagaag gggacagtaa     60

gaaggaaaaa caggtcaga                                                  79


<210> SEQ ID NO 47
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

attgtatttc caaagtccca ctgggcggca gcatagtgag cccagtaagg ggacagtaag     60

aaggaaaaac aggtcagag                                                  79


<210> SEQ ID NO 48
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48

attgtatttc caaagtccca ctgggcggca gcatagtgag cccagtaaga aggaaaaaca     60

ggtcagaga                                                             69


<210> SEQ ID NO 49
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49

attgtatttc caaagtccca ctgggcggca gcatagtgag ctccagaagg ggacagtaag     60

aaggaaaaac aggtcagag                                                  79
```

```
<210> SEQ ID NO 50
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50

attgtatttc caaagtccca ctgggcggca gcatagtgag cccaggagaa ggggacagta     60

agaaggaaaa acaggtcag                                                  79


<210> SEQ ID NO 51
<211> LENGTH: 79
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

attgtatttc caaagtccca ctgggcggca gcatagtgag ccgcagaagg ggacagtaag     60

aaggaaaaac aggtcagag                                                  79


<210> SEQ ID NO 52
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

attgtatttc caaagtccca ctgggcggca gcatagtgag acagtaagaa ggaaaaacag     60

gtcagaga                                                              68
```

TARGETING THE HUMAN CCR5 LOCUS AS A SAFE HARBOR FOR THE EXPRESSION OF THERAPEUTIC PROTEINS

CROSS REFERENCE TO RELATED APPLICATIONS

The present application is a U.S. national phase entry of International Patent Application No. PCT/US21/39206, filed on Jun. 25, 2021, which claims priority to U.S. Provisional Pat. Appl. No. 63/044,951, filed on Jun. 26, 2020, which applications are incorporated herein by reference in their entireties.

STATEMENT AS TO RIGHTS TO INVENTIONS MADE UNDER FEDERALLY SPONSORED RESEARCH AND DEVELOPMENT

This invention was made with government support under Grant No. NS102398 awarded by the National Institutes of Health. The government has certain rights in the invention.

SEQUENCE LISTING

The instant application contains a Sequence Listing which has been submitted electronically in .txt format and is hereby incorporated by reference in its entirety. Said .txt copy, created on Aug. 12, 2021, is named 079445-1254392-005510PC_SL and is 30,326 bytes in size.

BACKGROUND

Lysosomal storage diseases (LSDs) such as Mucopolysaccharidosis type I, Gaucher disease, and Krabbe disease comprise a large group of genetic disorders caused by deficiencies in lysosomal proteins, and many lack effective treatments. Collectively LSDs have an incidence in the population of about 1 in 7000 births and have severe effects including early death. While clinical trials are in progress on possible treatments for some of these diseases, there is currently no approved treatment for many LSDs. Current treatment options for some but not all LSDs include enzyme replacement therapy (ERT), a medical treatment which replaces an enzyme that is deficient or absent in the body. In some instances, this is done by giving the patient an intravenous (IV) infusion of a solution containing the enzyme. Enzyme replacement therapies, however, can have limited efficacy for various reasons. An alternative approach for treating LSDs would be genome editing. Recently developed genome editing tools combine precise gene addition with genetic alterations that can add therapeutic benefit (16). Among these, Clustered Regularly Interspaced Short Palindromic Repeats-associated protein-9 nuclease (CRISPR/Cas9) is the simplest to engineer and has been used to successfully modify human hematopoietic stem and progenitor cells (HSPCs) in culture (17,18).

This platform consists of two main components: (1) a sgRNA/Cas9 ribonucleoprotein complex (RNP) functioning as an RNA-guided endonuclease, and (2) a designed homologous repair template, delivered using a vector such as adeno-associated viral vector serotype six (AAV6). The RNP can be comprised of a 100-bp, chemically-modified, synthetically-generated, single guide RNA (sgRNA) complexed with *Streptococcus pyogenes* Cas9-endonuclase and delivered into the cells by, e.g., electroporation (31). In the nucleus, the RNP binds to the target sequence and Cas9 catalyzes a double-stranded break, stimulating one of two repair pathways: 1) non-homologous end joining (NHEJ), in which broken ends are directly ligated, often producing small insertions and deletions (indels); and 2) homology-directed repair (HDR), in which recombination with the supplied homologous repair template is used for precise sequence changes (32). In human hematopoietic stem and progenitor cells (HSPCs), the AAV6 genome is an efficient delivery method for the homologous repair templates containing an experimenter-defined genetic change flanked by homology arms centered at the break site (27). Accordingly, the HDR pathway can be leveraged not only to achieve single-base pair changes, but also to integrate entire expression cassettes, thus enabling stable expression of tailorable combinations of regulatory regions, transgenes, and selectable markers (29,33,34).

Although its therapeutic potential in LSDs remains to be explored, to maximize therapeutic correction by autologous transplantation of genetically modified HSPCs in some LSDs, functional enzymes must sometimes be expressed at higher-than-endogenous levels. This can be achieved by inserting an expression cassette (exogenous promoter-gene of interest) into non-essential genomic region (or "safe harbor"). A safe harbor provides a platform that is independent of specific patient mutations, is easily adaptable to various lysosomal enzymes and, compared to lentiviral transduction, ensures more predictable and consistent transgene expression because the insertion sites are restricted (up to 2 in autosomes). Moreover, its disruption has no effect on cell proliferation and no known potential for oncogenic transformation.

Mucopolysaccharidosis type I (MPSI) is a common LSD caused by insufficient iduronidase (IDUA) activity, which results in glycosaminoglycan (GAG) accumulation and progressive multi-systemic deterioration that severely affects the neurological and musculoskeletal systems (1). Current interventions for MPSI include enzyme replacement therapy (ERT) and allogeneic hematopoietic stem cell transplantation (allo-HSCT); both have limited efficacy. For example, ERT does not cross the blood-brain barrier, requires costly life-long infusions, and inhibitory antibodies can further decrease enzyme bioavailability (2). Allo-HSCT results in better outcomes than ERT by providing a persistent source of enzyme and tissue macrophages that can migrate into affected organs, including the brain, to deliver local enzyme (3,4,5). However, allo-HSCT also has significant limitations, including the uncertain availability of suitable donors, delay in treatment (allowing for irreversible progression), and transplant-associated morbidity and mortality such as graft-versus-host disease and drug-induced immunosuppression.

Human and animal studies in MPSI have shown that the therapeutic efficacy of HSCT can be enhanced by increasing the levels of circulating IDUA. In humans, patients transplanted with non-carrier donors had better clinical responses than patients transplanted with HSPCs from MPSI heterozygotes with decreased enzyme expression (6). In mice, transplantation of virally transduced murine hematopoietic stem and progenitor cells (HSPCs) expressing supra-normal enzyme levels (7,8) dramatically corrected the phenotype. Based on this, autologous transplantation of lentivirus-transduced HSPCs overexpressing lysosomal enzymes is being explored in human trials for LSDs including severe MPSI (ClinicalTrials.gov, NCT03488394) and Metachromatic leukodystrophy (9). The peroxisomal disorder X-linked adrenoleukodystrophy has also been successfully treated by lentiviral transduced autologous HSPCs, though supra-normal expression of the missing enzyme is probably not critical as cross-correction is not a feature of this disease (10,11). This autologous approach eliminates the need to find immunologically matched donors and reduces some of the potential complications from allogeneic transplants. However, concerns remain about the potential for tumorigenicity associated with random insertion of the viral genomes (12,13), carry-over of infectious particles (14), the immune response to some of the vectors, and variable transgene expression (15).

Gaucher Disease (GD) is genetic disorder caused by mutations in the GBA gene that result in glucocerebrosidase (GCase) deficiency and the accumulation of glycolipids in cell types with high glycolipid degradation burden, especially macrophages (1b). GD encompasses a spectrum of clinical findings from a perinatal-lethal form to mildly symptomatic forms. Three major clinical types delineated by the presence (types 2 and 3) or absence (type 1) of central nervous system involvement are commonly used for determining prognosis and management (2b). In western countries, GD type 1 (GD1) is the most common phenotype (~94% of patients) and typically manifests with hepatosplenomegaly, bone disease, cytopenias, and variably with pulmonary disease, as well as elevated risk for malignancies and Parkinson's disease (3b,4b).

The pathophysiology in GD1 is thought to be driven by glucocerebroside-engorged macrophages that infiltrate the bone marrow, spleen and liver, and promote chronic inflammation as well as low-grade activation of coagulation and complement cascades (5b-7b). Current therapies for GD1 include orally-available small-molecule inhibitors of glucosylceramide synthase (substrate reduction therapy or SRT) and glucocerebrosidase enzyme replacement (ERT) targeted to macrophages via mannose receptor-mediated uptake (8b-13b). While ameliorative for visceral and skeletal disease manifestations, these therapies are chronically administered, life-long, and costly. Allogeneic hematopoietic stem cell transplantation (allo-HSCT) has been applied successfully as a one-time treatment for GD1 (14b) and its therapeutic effect is likely achieved through supplying graft-derived GCase-competent macrophages. However, because of the significant transplant-related morbidity and mortality of allo-HSCT, ERT and SRT are standard of care for patients with GD1 (15b,16b).

The effectiveness of macrophage-targeted ERT and allo-HSCT for treating GD1 suggests that restoration of GCase function in macrophages alone is sufficient for phenotypic correction in GD1. Consequently, restoring GCase activity in the patient's own hematopoietic system to establish an autologous approach that averts many of the risks of allo-HSCT could be a safer and potentially curative therapy for this disease. Furthermore, unlike ERT and the best tolerated SRT, it could provide enzyme reconstitution in the brain that could benefit neuronopathic forms of the disease (14b). For these reasons, non-targeted gene addition into human hematopoietic stem and progenitor cells (HSPCs) have been explored, first using retroviruses (17b-20b) and later lentiviral vectors, and have yielded promising results in murine GD models (21b-23b). Nevertheless, concerns remain about the potential for insertional mutagenesis and malignant transformation in viral gene transfer (24b,25b) stressing the need for the development of "targeted" gene addition strategies to generate genetically modified HSPCs for human therapy.

Krabbe disease (also called globoid cell leukodystrophy) is an inherited neurological disorder, one of a group of disorders called leukodystrophies, that results from the loss of myelin (demyelination) of nerve cells in the nervous system. Krabbe disease can begin in infants (infantile form) or in childhood, adolescence, or adulthood (late-onset forms) and is caused by a deficiency in galactocerebrosidase (GALC) enzyme activity.

There is a need for new, safe, and effective approaches for introducing transgenes into cells encoding therapeutic proteins for the treatment of lysosomal storage disorders, for example into autologous HSPCs in vivo or ex vivo. The present disclosure satisfies this need and provides other advantages as well.

BRIEF SUMMARY

The present disclosure provides methods and compositions for treating lysosomal storage disorders (LSDs), in particular through the genetic modification of cells taken from a subject with an LSD in order to introduce a functional copy of a therapeutic gene into the cells, and subsequently reintroducing the modified cells back into the subject. In particular, the present methods and compositions involve the homologous-recombination mediated introduction of therapeutic transgenes into the genome of cells at the CCR5 locus.

Accordingly, in one aspect, the present disclosure provides a method of genetically modifying a cell from a subject with a lysosomal storage disorder (LSD), the method comprising: introducing into a cell isolated from the subject a single guide RNA (sgRNA) targeting the CCR5 locus, an RNA-guided nuclease, and a homologous donor template comprising a transgene encoding a therapeutic protein that is absent or deficient in the subject, wherein: the sgRNA binds to the nuclease and directs it to a target sequence at the CCR5 locus in the genome comprising the sequence shown as SEQ ID NO:3 or SEQ ID NO:4, whereupon the nuclease cleaves the CCR5 locus at the target sequence, wherein: the homologous donor template comprises a first homology region comprising the sequence of SEQ ID NO:1 or a fragment thereof to one side of the transgene, and a second homology region comprising the sequence of SEQ ID NO:2 or a fragment thereof to the other side of the transgene, and the transgene is integrated into the genome by homology directed recombination (HDR) at the site of the cleaved CCR5 locus, and wherein: the integrated transgene directs the expression of the therapeutic protein in the cell.

In some embodiments, the method further comprises isolating the cell from the subject prior to the introducing of the sgRNA, RNA-guided nuclease, and homologous donor template. In some embodiments, the sgRNA comprises chemical modifications at one or more nucleotides. In some such modifications, the sgRNA comprises 2'-O-methyl-3'-phosphorothioate (MS) modifications at one or more nucleotides. In some such embodiments, the 2'-O-methyl-3'-phosphorothioate (MS) modifications are present at the three terminal nucleotides of the 5' and 3' ends. In some embodiments, the target sequence of sgRNA comprises the sequence of SEQ ID NO:3 or SEQ ID NO:4. In some embodiments, the sgRNA comprises the sequence of SEQ ID NO:5. In some embodiments, the RNA-guided nuclease is Cas9. In some embodiments, the sgRNA and the RNA-guided nuclease are introduced into the cell as a ribonucleoprotein (RNP). In some embodiments, the RNP is introduced into the cell by electroporation. In some embodiments, the transgene is present within an expression cassette. In some such embodiments, the expression cassette comprises a coding sequence for the therapeutic protein, operably linked to a promoter, and an exogenous polyadenylation signal. In some embodiments, the polyadenylation signal is a bovine growth hormone polyadenylation signal. In some embodiments, the homologous donor template is introduced into the cells using a recombinant adeno-associated virus (rAAV) vector. In some such embodiments, the recombinant adeno-associated virus is serotype 6 (rAAV6).

In some embodiments, the LSD is mucopolysaccharidosis type 1, and the therapeutic protein is iduronidase. In some embodiments, the transgene is part of an expression cassette comprising the coding sequence for iduronidase, operably linked to a phosphoglycerate kinase (PGK) promoter or a spleen focus-forming virus (SFFV) promoter. In some embodiments, the homologous donor template comprises the sequence of SEQ ID NO: 6 or SEQ ID NO: 7. In some embodiments, the cell is a $CD34^+$ hematopoietic stem and progenitor cell (HSPC). In some embodiments, the LSD is Gaucher disease, and the therapeutic protein is glucocerebrosidase. In some such embodiments, the transgene is part of an expression cassette comprising the coding sequence for glucocerebrosidase, operably linked to a CD68 promoter or derivative thereof. In some embodiments, the donor template comprises the sequence of SEQ ID NO: 8. In some embodiments, the cell is a $CD34^+$ hematopoietic stem and progenitor cell (HSPC). In some embodiments, the LSD is Krabbe disease, and the therapeutic protein is galactocerebrosidase. In some embodiments, the transgene is part of an expression cassette comprising the coding sequence for galactocerebrosidase, operably linked to a CD68 promoter or a derivative thereof. In some such embodiments, the cell is a $CD34^+$ hematopoietic stem and progenitor cell (HSPC) or a neuronal stem cell.

In another aspect, the present disclosure provides a method of treating a subject in need thereof with a lysosomal storage disorder, comprising (i) genetically modifying a cell from the subject using any of the herein-described methods, and (ii) reintroducing the cell into the subject, wherein the reintroducing is effective to treat the subject.

In some embodiments, the cell is reintroduced into the subject by systemic transplantation. In some embodiments, the cell is reintroduced into the subject by local transplantation. In some embodiments, the transplantation is intrafemoral or intrahepatic. In some embodiments, the cell is cultured, selected, and/or induced to undergo differentiation in vitro prior to being reintroduced into the subject.

In another aspect, the present disclosure provides an sgRNA that specifically targets the CCR5 gene, wherein the target sequence of the sgRNA comprises the nucleotide sequence of SEQ ID NO:3 or SEQ ID NO:4.

In some embodiments, the sgRNA comprises the nucleotide sequence of SEQ ID NO:5. In some embodiments, the sgRNA comprises chemical modifications at one or more nucleotides. In some such embodiments, the sgRNA comprises 2'-O-methyl-3'-phosphorothioate (MS) modifications at one or more nucleotides. In some embodiments, the 2'-O-methyl-3'-phosphorothioate (MS) modifications are present at the three terminal nucleotides of the 5' and 3' ends.

In another aspect, the present disclosure provides a homologous donor template comprising: (i) an expression cassette comprising: (a) a coding sequence for a therapeutic protein, operably linked to (b) a promoter, and (c) a polyadenylation signal at the 3' end of the coding sequence; (ii) a first CCR5 homology region located to one side of the expression cassette within the donor template, wherein the first CCR5 homology region comprises SEQ ID NO:1 or a fragment thereof, and (iii) a second CCR5 homology region located to the other side of the expression cassette within the donor template, wherein the second CCR5 homology region comprises SEQ ID NO:2 or a fragment thereof.

In some embodiments, the therapeutic protein is iduronidase. In some embodiments, the therapeutic protein is glucocerebrosidase. In some embodiments, the therapeutic protein is galactocerebrosidase. In some embodiments, the donor template comprises the sequence of SEQ ID NO: 6, SEQ ID NO: 7, or SEQ ID NO: 8.

In another aspect, the present invention provides an HSPC comprising any of the herein-described sgRNAs and/or homologous donor templates.

In another aspect, the present disclosure provides a genetically modified HSPC comprising an integrated transgene at the CCR5 locus, wherein the integrated transgene comprises a coding sequence for iduronidase, glucocerebrosidase, or galactocerebrosidase. In some embodiments, the HSPC was modified using any of the herein-described methods.

BRIEF DESCRIPTION OF THE DRAWINGS

FIG. 1A: Schematic of targeted integration of IDUA and expression cassettes. The AAV6 genome was constructed to have 500 bp arms of homology centered on the cut site, and the IDUA sequence placed under the control of the SFFV or the PGK promoter (E=Exon). In two DNA templates, YFP was expressed downstream of IDUA using the self-cleaving P2A peptide. FIG. 1A discloses SEQ ID NO: 3. FIG. 1B: Representative FACs and histogram plots 3-days post-modification of mock and human HSPCs that underwent RNP and AAV6 exposure with YFP-containing expression cassettes. FIG. 1C: Targeting frequencies in cord blood (CB, red dots) and adult peripheral blood (PB, blue dots)-derived HSPCs read by percent fluorescent cells in YFP-expressing cassettes and percent colonies with targeted CCR5 alleles by single cell-derived colony genotyping in cassettes without the reporter. Each dot represents the average of duplicates for a human cell donor. For RNP+AAV6 conditions with YFP templates, n=20 and n=11 independent human donors for CB and PB respectively. For the template without selection n=6 independent human donors in CB and PB. Data shown as mean±SD. FIG. 1D: Distribution of wild type (WT), mono and bi-allelically modified cells (n=400) in YFP-positive HSPCs FIGS. 2A-2F. Enhanced IDUA expression by IDUA-HSPCs and derived macrophages. FIGS. 2C, 2E, 2F: Each column represents average of triplicates in n=3 independent biological samples. All data expressed as mean±SD, ***$p<0.001$ in two-sided unpaired t-test. Source data are provided as a Source Data file.

FIGS. 3A-3G. IDUA-HSPCs maintain long-term repopulation capacity. FIG. 3A: Schematic and representative FACS plots showing phenotyping by flow of human, myeloid, B-cell, and targeted cells after engraftment. FIG. 3B: Percent human cell chimerism in bone marrow (BM) and peripheral blood (PM) of mice 16-weeks post-transplant with CB (blue dots) and PB (red dots)-derived HSPCs targeted with PGK-IDUA-YFP cassette. Each point represents an individual mouse; mock (n=11), YFP− (n=21), and YFP+ (n=36). FIG. 3C: Percent human, YFP+ cells in BM of mice in BM 16-weeks post-transplant. FIG. 3D: Percent human cell chimerism in BM in mice transplanted with bulk cells without selection with two different human cell donors; donor 1 n=9, donor 2 n=5. FIG. 3E: Percent modified alleles in engrafted cells by ddPCR. 28% was the starting allele modification frequency for both human donors. FIG. 3F: Percent human cell chimerism in BM of mice in secondary transplants 32 weeks after genome editing; YFP− (n=10), and YFP+ (n=10). FIG. 3G: Percent human, YFP+ cells in BM of mice in secondary transplants.

FIG. 4A: Percent human and YFP+ cells in BM in experiments using bulk and sorted cells. FIG. 4B: Urinary GAGs at 4, 8, and 18 weeks in experiments using bulk cells (n=5 mice per cohort, two measurements per mouse). FIG. 4C: Plasma and tissue IDUA activity in experiments using bulk cells (n=5 per cohort). FIG. 4D: Fold GAG storage in liver, spleen, and brain (normalized by W/X sham, n=5 per cohort). FIG. 4E: Plasma and tissue IDUA activity in experiments using sorted cells (n=5 for W/X Tx and sham mice, and n=13 for X/X Tx and sham mice). FIG. 4F: Fold GAG urinary excretion and tissue storage in experiments using sorted cells (normalized by W/X sham). Median values shown in all scatter plots. FIGS. 4D, 4F show box plots with whiskers at the 5-95th percentiles. ****$p<0.0001$ in one-way ANOVA test. Post hoc comparisons were made with the Tukey's multiple comparisons test.

FIG. 5A: Representative photos showing facial features in mice transplanted with bulk cells. FIG. 5B: Bony features in mice transplanted with bulk cells (W/X sham (clear), X/X sham (blue), and X/X Tx (red), n=5 mice per cohort. Box plots with whiskers show median, min and max. FIG. 5C: Bony features in mice transplanted with sorted cells (W/X sham (clear or gray, n=11), X/X sham (blue, n=10), and X/X Tx (red, n=11). FIG. 5D: Ambulatory distance in mice transplanted with sorted cells. W/X sham vs. X/X sham: **; W/X sham vs. X/X Tx: n.s.; X/X sham vs. X/X Tx: *. FIG. 5E: Vertical rearing in mice transplanted with sorted cells. W/X sham vs. X/X sham: * W/X sham vs. X/X Tx: n.s.; X/X sham vs. X/X Tx: *. FIG. 5F: Memory retention in mice transplanted with sorted cells. FIG. 5G: Quantification of digging behavior in mice transplanted with sorted cells. FIGS. 5H-5I: Measurement of neuroinflammation in the cerebral cortex, n=3 mice in five sections. FIG. 5H: Microglia (Isolectin B4, n=15 brain sections from three independent mice, and (FIG. 5I) astrocytes (GFAP, n=15 brain sections from 3 independent mice. For FIGS. 5D-5G, data shown as mean±SEM. For FIGS. 5H-5I: data shown as mean±SD. All comparisons between groups were performed using one-way ANOVA test and post hoc comparisons were made with the Tukey's multiple comparisons test. *$p<0.05$, $p<0.01$, *$p<0.001$, and ****$p<0.0001$. Open field testing and vertical rearings were analyzed using within-subject modeling by calculating the area under the curve for each mouse within the first five minutes and comparing between groups with one-way ANOVA. Source data are provided as a Source Data file FIG. 6. OFF-target analysis of the CCR5 sgRNA. Percent reads with Indels at 62 off-target sites (OT) predicted using COSMID. For each site, red dots indicate samples treated with WT Cas9 and blue dots indicate samples treated with HiFi Cas9. The limit of detection for NGS is 0.1% and is indicated on the graph by a dashed line.

FIGS. 7A-7E. Characterization of the CCR5 sgRNA. FIG. 7A: Indel frequency in Cord blood (CB, red) and adult peripheral blood (PB, blue)-derived cells by the RNP complex. Data expressed as mean±SD. CB n=13 and PB n=13. Each dot represents a different biological sample. FIG. 7B: Representative indel distribution from next generation sequencing reads. FIG. 7C: Representative histogram of CCR5 protein expression in mock and RNP-treated cells showing an 80% reduction in protein expression after RNP electroporation. FIG. 7D: Sample sequence traces around the CCR5 sgRNA sequence (gray box, PAM in red) in mock samples and RNP-treated CB-derived HSPCs showing predominant single A insertion. FIG. 7D discloses SEQ ID NOS 30-31, respectively, in order of appearance. FIG. 7E: Representative summary of indels with frequencies greater than 0.1%. FIG. 7E discloses SEQ ID NOS 32-52, respectively, in order of appearance.

FIGS. 8A-8E. Efficiency of modification at the CCR5 locus. FIG. 8A: Schematic showing the three primer-based genotyping scheme to distinguish mono and bi-allelic integration into the CCR5 locus on CFA-derived colonies. This strategy did not distinguish WT versus alleles with indels (NHEJ). FIG. 8B: Example agarose gels of 40 colonies genotyped in this manner. A single 1.1 Kb band was interpreted as WT/NHEJ in both alleles, while a single 0.6 Kb band was read as bi-allelic integration. FIG. 8C: Schematic of probe design for ddPCR analysis. Fraction of modified alleles was obtained by using a second reference probe to the CCRL2 gene also on chromosome 3p. FIG. 8D: Two probes where each straddled a 5' or 3' homology arm were designed. The accuracy of the assays was compared using genomic DNA from colonies derived from mono-allelic cells (0.5 fraction of alleles modified). Error bars indicate 95% CI. The 3' HA probe was selected. FIG. 8E: CCR5 allele targeting frequencies in CB (red n=20) and PB (blue n=11)-derived IDUA expressing HSPCs as measured by ddPCR. For the template without selection CB=6, PB=6. Data shown as mean±SD. Source data are provided as a Source Data file.

FIGS. 9A-9E. Efficient targeting of GCase to the CCR5 locus in human HSPCs 48-hours post-modification. FIG. 9A: Schematic of gene targeting mediated by sgRNA/Cas9 RNP and rAAV targeting vectors. FIG. 9A discloses SEQ ID NO: 4. FIG. 9B: Schematic of expected CD68S promoter activation. FIG. 9C: Representative flow plots of Citrine expression versus forward scatter (FSC) for HSPCs without treatment (mock), treated with rAAV alone (AAV), and treated with RNP and rAAV (RNP+AAV). FIG. 9D: Flow cytometric quantification of Citrine+ HSPCs targeted with SFFV-GCase-P2A-Citrine and CD68S-GCase-P2A-Citrine vectors (n=9). FIG. 9E: Percent of CCR5 alleles with integrated CD68S-GBA-P2A-Citrine and SFFV-GBA-P2A-Citrine cassettes in AAV only (white), bulk (black), FACS-enriched Citrine− (gray) and Citrine+ (green) HSPCs, and in CD68S-GCase-targeted unselected cells (black). Data shown as mean±SD.

FIG. 10A: Representative images showing phase contrast, phagosomes visualized by pHrodo-labeled *E. coli*, and nuclei in mock-treated human HSPCs after 20 days in macrophage differentiation media. FIG. 10B: Human CD34, CD14, and CD11b marker expression in HSPC-derived macrophages and human monocyte-derived macrophages after in vitro differentiation compared to undifferentiated cells ($CD34^+$ HSPCs). FIG. 10C: Representative images showing phase contrast, Citrine expression, phagosomes visualized by pHrodo-labeled *E. coli*, and nuclei in mock-treated, SFFV-GCase-P2A-Citrine, and CD68S-GCase-P2A-Citrine targeted macrophages. FIG. 10D: Human CD14, and CD11b marker expression in the same cells with and without in vitro differentiation. Left graph: CD11b+. Middle graph: $CD14^+$. Right graph: CD11b+/$CD14^+$. FIG. 10E: Representative FACS plots of FMO's and Mock sample showing CD11b and CD14 expression in HSPC maintenance or Macrophage differentiation media. FIG. 10F: Representative FACS plots showing CD11b and CD14 expression in CD68S-GCase-Citrine+ and SFFV-GCase-Citrine+ cells in HSPC maintenance or macrophage differentiation media. Data shown as mean±SD (n=3).

FIGS. 11A-11F. The CD68S promoter confines GCase expression to the monocyte/macrophage lineage. FIG. 11A: Representative flow plots depicting Citrine+ and Citrine− populations at the time of sort (day 0, 48-h post-modification) and after 20 days in HSPC maintenance (HSPC) or macrophage differentiation (MΦ) cultures. FIG. 11B: Citrine expression expressed as % Citrine+ cells over time in HSPC and MΦ cultures (n=3 biological replicates). FIG. 11C: Citrine expression expressed MFI over time in HSPC and MΦ cultures in the CD68S-GCase-P2A-Citrine-targeted cells. FIG. 11D: Fold GCase activity in HSPC and FIG. 11E: MΦ cultures in targeted cells compared to unmodified (mock-treated) cells (n=3). Comparisons between groups were performed using one-way ANOVA test and post-hoc comparisons were made with the Tukey's multiple comparisons test. : $p<0.01$. FIG. 11**F: Percent of targeted CCR5 alleles at the time of sort and after 20 days in HSPC and MΦ cultures (n=3). Data shown as mean±SD. Source data are provided as a Source Data file.

FIG. 12A: Total number of colonies formed from mock, Citrine+ and Citrine− SFFV and CD68S-driven constructs. FIG. 12B: Distribution of phenotypes of colonies formed. Erythroid progenitors (burst forming unit-erythroid or BFU-E (red)) and colony-forming unit-erythroid or CFU-E (blue), granulocyte-macrophage progenitors (CFU-GM, green), and multi-potential granulocyte, erythroid, macrophage, megakaryocyte progenitor cells (CFU-GEMM, purple). FIG. 12C: Primary human engraftment (16-wks) in the bone marrow in transplants using CD68S-GCase-targeted and CD68S-GCase-P2A-Citrine-targeted cells (Blue circles: 0.25E6, green: 1E6, and red: 2E6 cells transplanted; n=31,33). FIG. 12D: Primary human engraftment in the spleen. FIG. 12E: Targeted allele frequency in CD68S-GCase- and CD68S-GCase-P2A-Citrine-targeted cells before transplantation (Pre-Tx) and 16-wks post-transplantation (Post-Tx) in engrafted human cells in bone marrow of mice with human chimerism >1% (n=29,31). FIG. 12F: Secondary human engraftment (32-wks) in the bone marrow (n=8, 3 with chimerism <1%). FIG. 12G: Targeted allele frequency before (Pre-Tx) and after transplant (Post-Tx) in the bone marrow cells of secondary mice. FIGS. 12A-12B: Data shown as mean±SD. (c-g) Medians shown.

FIGS. 13A-13E. In vivo monocyte/macrophage lineage differentiation of GCase-targeted HSPCs. FIG. 13A: Distribution of B-lymphoid and myeloid lineage cells within the engrafted human cell population in the bone marrow from mice transplanted with CD68S-GCase and CD68S-GCase-P2A-Citrine-targeted HSPCs (n=29, 31). FIG. 13B: Distribution of B-lymphoid and lineage cells within the engrafted human cell population from secondary transplants. Empty: vector without Citrine (n=5). FIG. 13C: Representative FACS plots showing Citrine expression in human CD33+ (myeloid), $CD14^+$ (monocyte) and CD19 (B-cells). FIG. 13D: Percent Citrine positive cells in monocyte, myeloid, and B-cell populations in mice with human CCR5 allele modification fraction >10%. FIG. 13E: Representative epi-fluorescence microscopy images of in vitro generation of human CD68S-GBA1-P2A-Citrine-targeted macrophages from sorted $CD14^+$ monocytes. Images depict morphology (brightfield), nuclei (Hoechst), CD68S (red), and Citrine (green). FIGS. 13A, 13B, 13D: Median shown. Source data are provided as a Source Data file.

FIGS. 14A-14H. Improved macrophage differentiation of GCase-targeted HSPCs in NSG-SGM3 mice. FIG. 14A: Human cell engraftment 16-weeks post-transplantation in the bone marrow (BM), spleen (SP), and peripheral blood (PB) in transplants using CD68S-GCase-P2A-Citrine-targeted cells (n=5). FIG. 14B: Modified allele frequency from engrafted CD68S-GCase-P2A-Citrine-targeted cells (n=5). FIG. 14C: Percent human B-cell ($CD19^+$), myeloid ($CD33^+$), and monocyte ($CD14^+$) populations in BM, SP, and PB shown in white. Citrine positive cells in each population are shown in green. FIG. 14D: Representative FACS plots showing $CD45^+$, $CD45^+/CD11b^+$ and $CD45^+/CD11b^+$/Citrine populations in macrophage preparations from lung, peritoneal macrophages, and liver. FIG. 14E: Percent human $CD45^+$ and human $CD45^+$/Citrine cells (n=5). FIG. 14F: Percent human $CD45^+/CD11b^+$ and human $CD45^+/CD11b^+$/Citrine cells (n=5). FIG. 14G: Fold GCase activity in human $Citrine^+$ cells compared to human $Citrine^-$ cells in BM, SP, and lung from three different mice FIG. 1411: Modified allele frequency in human $Citrine^+$ cells compared to human $Citrine^-$ cells in BM, SP, and lung from three different mice.

DETAILED DESCRIPTION

1. Introduction

Figures 1A, 1B, 1C, 1D:
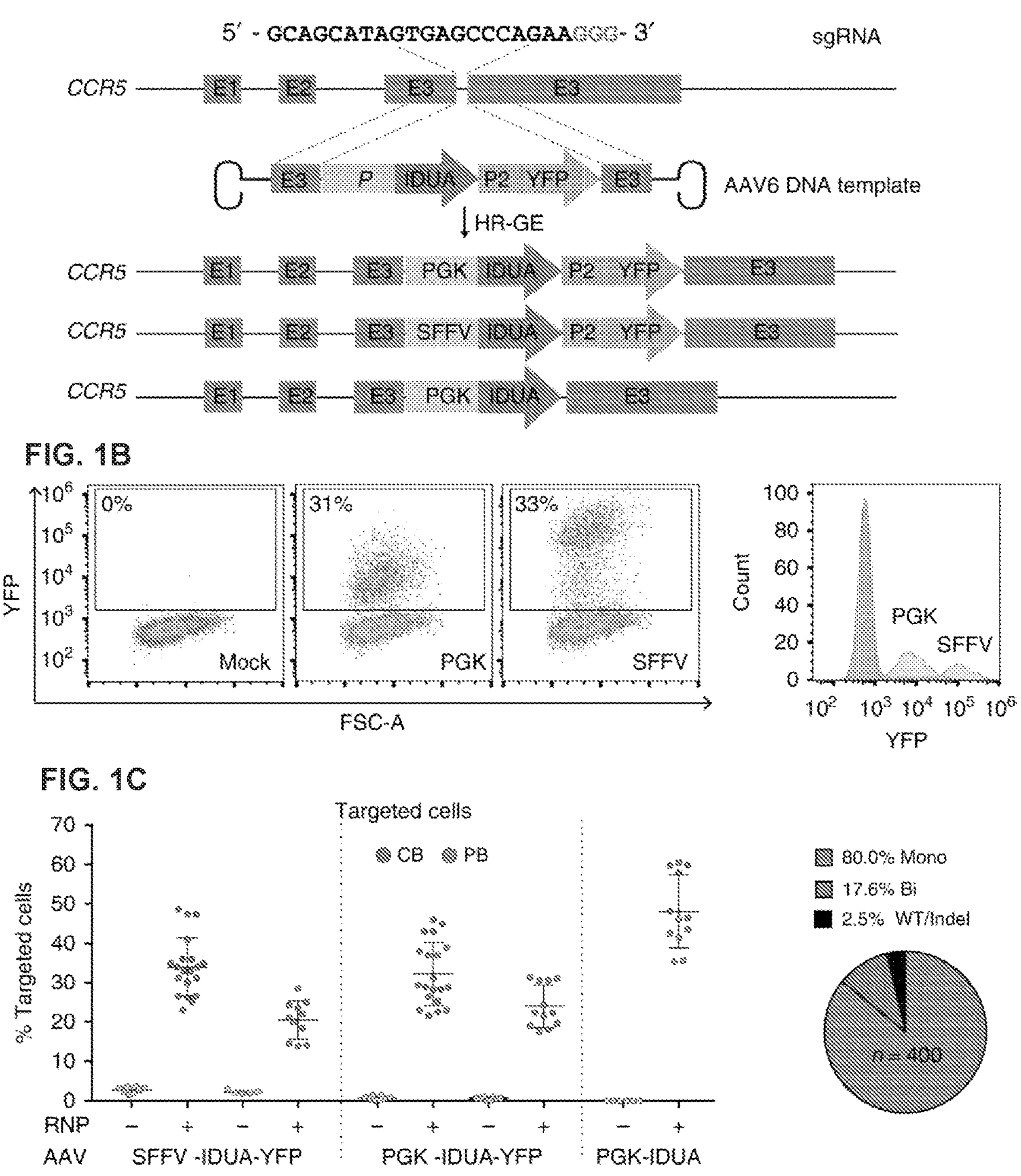
FIGS. 1A-1D. Efficient CRIPR/Cas9-mediated integration of IDUA overexpression cassettes into the CCR5 locus in human $CD34^+$ HSPCs.

The present disclosure provides methods and compositions for the treatment of lysosomal storage disorders in subjects through the introduction and integration at the CCR5 locus of transgenes encoding therapeutic proteins. The methods involve the introduction of ribonucleoproteins (RNPs) comprising single guide RNAs (sgRNAs) and RNA-guided nucleases (e.g., Cas9) into cells from the subject, as well as the introduction of homologous templates for repair. In particular, the methods and compositions can be used to efficiently introduce and express functional transgenes encoding enzymes that are deficient in the subject. In particular embodiments, the RNP complexes, e.g., comprising CCR5 sgRNA and Cas9 protein, are delivered to cells via electroporation, followed by the transduction of the homologous template using an AAV6 viral vector. The homologous templates for repair are constructed to have arms of homology centered on the cut site, located on either side of the coding sequence for a therapeutic protein of interest, under the control of a designated promoter. Transcription is terminated using an exogenous polyadenylation signal. Depending on the promoter, the system can achieve, e.g., supraphysiological expression and/or cell-specific expression. This system can be used to modify any human cell.

2. General

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb), base pairs (bp), or nucleotides (nt). Sizes of single-stranded DNA and/or RNA can be given in nucleotides. These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

3. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells, and so forth.

The terms "about" and "approximately" as used herein shall generally mean an acceptable degree of error for the quantity measured given the nature or precision of the measurements. Typically, exemplary degrees of error are within 20 percent (%), preferably within 10%, and more preferably within 5% of a given value or range of values. Any reference to "about X" specifically indicates at least the values X, 0.8X, 0.81X, 0.82X, 0.83X, 0.84X, 0.85X, 0.86X, 0.87X, 0.88X, 0.89X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, 1.1X, 1.11X, 1.12X, 1.13X, 1.14X, 1.15X, 1.16X, 1.17X, 1.18X, 1.19X, and 1.2X. Thus, "about X" is intended to teach and provide written description support for a claim limitation of, e.g., "0.98X."

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)).

The term "gene" means the segment of DNA involved in producing a polypeptide chain. It may include regions preceding and following the coding region (leader and trailer) as well as intervening sequences (introns) between individual coding segments (exons).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. The promoter can be a heterologous promoter.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. The promoter can be a heterologous promoter. In the context of promoters operably linked to a polynucleotide, a "heterologous promoter" refers to a promoter that would not be so operably linked to the same polynucleotide as found in a product of nature (e.g., in a wild-type organism).

As used herein, a first polynucleotide or polypeptide is "heterologous" to an organism or a second polynucleotide or polypeptide sequence if the first polynucleotide or polypeptide originates from a foreign species compared to the organism or second polynucleotide or polypeptide, or, if from the same species, is modified from its original form. For example, when a promoter is said to be operably linked to a heterologous coding sequence, it means that the coding sequence is derived from one species whereas the promoter sequence is derived from another, different species; or, if both are derived from the same species, the coding sequence is not naturally associated with the promoter (e.g., is a genetically engineered coding sequence).

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The terms "expression" and "expressed" refer to the production of a transcriptional and/or translational product, e.g., of a therapeutic protein and/or a nucleic acid sequence encoding a therapeutic protein. In some embodiments, the term refers to the production of a transcriptional and/or translational product encoded by a gene (e.g., a iduronidase, glucocerebrosidase, or galactocerebrosidase gene) or a portion thereof. The level of expression of a DNA molecule in a cell may be assessed on the basis of either the amount of corresponding mRNA that is present within the cell or the amount of protein encoded by that DNA produced by the cell.

A "therapeutic protein" as used herein refers to a protein or a functional fragment thereof, encoded by a "therapeutic gene", that is deficient in a patient with a lysosomal storage disorder (LSD) or whose expression would be beneficial in a patient with an LSD. Typically, the therapeutic protein is a lysosomal enzyme, but any secreted protein that would be beneficial for a patient with an LSD can be used. In particular embodiments, the therapeutic protein is iduronidase (in particular for patients with mucopolysaccharidosis type I, which is caused by mutations in the IDUA gene), glucocerebrosidase (in particular for patients with Gaucher disease, which is caused by mutations in the GBA gene), or galactocerebrosidase (in particular for patients with Krabbe disease, which is caused by mutations in the GALC gene).

The term "treating" or "treatment" refers to any one of the following: ameliorating one or more symptoms of a disease or condition (e.g., a lysosomal storage disorder); preventing the manifestation of such symptoms before they occur; slowing down or completely preventing the progression of the disease or condition (as may be evident by longer periods between reoccurrence episodes, slowing down or prevention of the deterioration of symptoms, etc.); enhancing the onset of a remission period; slowing down the irreversible damage caused in the progressive-chronic stage of the disease or condition (both in the primary and secondary stages); delaying the onset of said progressive stage; or any combination thereof.

As used herein, the terms "subject", "individual" or "patient" refer, interchangeably, to a warm-blooded animal such as a mammal. In particular embodiments, the term refers to a human. A subject may have, be suspected of having, or be predisposed to a lysosomal storage disorder as described herein. The term also includes livestock, pet animals, or animals kept for study, including horses, cows, sheep, poultry, pigs, cats, dogs, zoo animals, goats, primates (e.g. chimpanzee), and rodents. A "subject in need thereof" refers to a subject that has one or more symptoms of a lysosomal storage disorder (LSD), that has received a diagnosis of an LSD, that is suspected of having or being predisposed to a LSD, that shows a deficiency of one or more therapeutic proteins as described herein, or that is thought to potentially benefit from increased expression of a therapeutic protein as described herein.

An "effective amount" refers to an amount of a compound or composition, as disclosed herein effective to achieve a particular biological, therapeutic, or prophylatic result. Such results include, without limitation, the treatment of a disease or condition disclosed herein as determined by any means suitable in the art.

"Iduronidase" is an enzyme (see, e.g., UniProt ID P35475 for human Alpha-L-iduronidase), encoded by the IDUA gene (see, e.g., NCBI Gene ID 3425 for human IDUA), that hydrolyzes the terminal alpha-L-iduronic acid residues of two glycosaminoglycans, dermatan sulfate and heparan sulfate. This hydrolysis reaction is required for the degradation of these glycosaminoglycans in lysosomes. Mutations in this gene that result in enzymatic deficiency lead to, e.g., mucopolysaccharidosis type I (MPS I), a lysosomal storage disorder (LSD) as described herein. Any iduronidase enzyme, from any source, or any polynucleotide encoding an iduronidase enzyme, can be used in the present methods, so long that it is capable of hydrolyzing terminal alpha-L-iduronic acid residues and restoring or increasing enzyme function in cells, e.g., cells of a subject with MPS I. In particular embodiments, the iduronidase used in the present methods is encoded by a polynucleotide comprising nucleotides 1002-2960 of SEQ ID NO:6 or SEQ ID NO:7, or to a functional iduronidase encoded by a polynucleotide comprising a sequence with, e.g., 50%, 55%, 60%, 65%, 70%, 75%, 80%, 85%, 90%, 91%, 92%, 93%, 94%, 95%, 96%, 97%, 98%, 99%, or more identity to nucleotides 1002-2960 of SEQ ID NO:6 or SEQ ID NO:7.

"Glucocerebrosidase" or "beta-glucocerebrosidase" or "glucosylceramidase beta" is a lysosomal enzyme (see, e.g., UniProt ID P04062 for human glucocerebrosidase/glucosylceramidase), encoded by the GBA gene (see, e.g., NCBI Gene ID 2629 for human GBA), that hydrolyzes glucosylceramide into free ceramide and glucose. Mutations in this gene that result in enzymatic deficiency lead, e.g., to Gaucher disease, a lysosomal storage disorder (LSD) as described herein that involves an accumulation of glucocerebrosides. Any glucocerebrosidase or glucosylceramidase enzyme, from any source, or any polynucleotide encoding a glucocerebrosidase or glucosylceramidase enzyme, can be used in the present methods, so long that it is capable of hydrolyzing a beta-glucosidic linkage in glucosylceramide and thereby restoring or increasing enzyme function in cells, e.g., cells of a subject with Gaucher disease. In particular embodiments, the iduronidase used in the present methods is encoded by a polynucleotide comprising nucleotides 982-2589 of SEQ ID NO:8, or to a functional iduronidase encoded by a polynucleotide comprising a sequence with, e.g., 50%, 55%, 60%, 65%, 70%, 75%, 80%, 85%, 90%, 91%, 92%, 93%, 94%, 95%, 96%, 97%, 98%, 99%, or more identity to nucleotides 982-2589 of SEQ ID NO:8.

"Galactocerebrosidase" or "galactoceramidase" is a lysosomal enzyme (see, e.g., UniProt ID P54803 for human galactocerebrosidase/galactoceramidase), encoded by the GALC gene (see, e.g., NCBI Gene ID 2581 for human GALC), that hydrolyzes galactoester bonds of glycolipids such as galactosylceramide and galctosylsphingosine. Mutations in this gene that result in enzymatic deficiency lead, e.g., to Krabbe disease, a lysosomal storage disorder (LSD) as described herein. Any galactocerebrosidase or galactoceramidase enzyme, from any source, or any polynucleotide encoding a galactocerebrosidase or galactoceramidase enzyme, can be used in the present methods, so long that it is capable of hydrolyzing galactoester bonds of glycolipids and thereby restoring or increasing enzyme function in cells, e.g., cells of a subject with Krabbe disease.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles. In some cases, conservatively modified variants of a therapeutic protein can have an increased stability, assembly, or activity as described herein.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

As used in herein, the terms "identical" or percent "identity," in the context of describing two or more polynucleotide or amino acid sequences, refer to two or more sequences or specified subsequences that are the same. Two sequences that are "substantially identical" have at least 60% identity, preferably 65%, 70%, 75%, 80%, 85%, 90%, 91%, 92%, 93%, 94%, 95%, 96%, 97%, 98%, 99%, or 100% identity, when compared and aligned for maximum correspondence over a comparison window, or designated region as measured using a sequence comparison algorithm or by manual alignment and visual inspection where a specific region is not designated. With regard to polynucleotide sequences, this definition also refers to the complement of a test sequence. With regard to amino acid sequences, in some cases, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST 2.0 algorithm and the default parameters discussed below are used.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

An algorithm for determining percent sequence identity and sequence similarity is the BLAST 2.0 algorithm, which is described in Altschul et al., (1990) *J. Mol. Biol.* 215: 403-410. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The "CRISPR-Cas" system refers to a class of bacterial systems for defense against foreign nucleic acids. CRISPR-Cas systems are found in a wide range of bacterial and archaeal organisms. CRISPR-Cas systems fall into two classes with six types, I, II, III, IV, V, and VI as well as many sub-types, with Class 1 including types I and III CRISPR systems, and Class 2 including types II, IV, V and VI; Class 1 subtypes include subtypes I-A to I-F, for example. See, e.g., Fonfara et al., *Nature* 532, 7600 (2016); Zetsche et al., *Cell* 163, 759-771 (2015); Adli et al. (2018). Endogenous CRISPR-Cas systems include a CRISPR locus containing repeat clusters separated by non-repeating spacer sequences that correspond to sequences from viruses and other mobile genetic elements, and Cas proteins that carry out multiple functions including spacer acquisition, RNA processing from the CRISPR locus, target identification, and cleavage. In class 1 systems these activities are effected by multiple Cas proteins, with Cas3 providing the endonuclease activity, whereas in class 2 systems they are all carried out by a single Cas, Cas9.

A "homologous repair template" refers to a polynucleotide sequence that can be used to repair a double stranded break (DSB) in the DNA, e.g., a CRISPR/Cas9-mediated break at the CCR5 locus as induced using the herein-described methods and compositions. The homologous repair template comprises homology to the genomic sequence surrounding the DSB, i.e., comprising CCR5 homology arms of the invention. In some embodiments, two distinct homologous regions are present on the template, with each region comprising at least 50, 100, 200, 300, 400, 500, 600, 700, 800, 900 or more nucleotides or more of homology with the corresponding genomic sequence. In particular embodiments, the templates comprise two homology arms comprising about 500 nucleotides of homology extending from either site of the sgRNA target site. The repair template can be present in any form, e.g., on a plasmid that is introduced into the cell, as a free floating doubled stranded DNA template (e.g., a template that is liberated from a plasmid in the cell), or as single stranded DNA. In particular embodiments of the present invention, the template is present within a viral vector, e.g., an adeno-associated viral vector such as AAV6. In particular embodiments, the templates comprise an expression cassette comprising a sequence encoding a therapeutic protein, e.g., iduronidase, glucocerebrosidase, or galactocerebrosidase, operably linked to a promoter, such that the expression cassette is integrated into the genome at the CCR5 locus and the therapeutic protein is expressed.

As used herein, "homologous recombination" or "HR" refers to insertion of a nucleotide sequence during repair of double-strand breaks in DNA via homology-directed repair mechanisms. This process uses a "donor template" or "homologous repair template" with homology to nucleotide sequence in the region of the break as a template for repairing a double-strand break. The presence of a double-stranded break facilitates integration of the donor sequence. The donor sequence may be physically integrated or used as a template for repair of the break via homologous recombination, resulting in the introduction of all or part of the nucleotide sequence. This process is used by a number of different gene editing platforms that create the double-strand break, such as meganucleases, such as zinc finger nucleases (ZFNs), transcription activator-like effector nucleases (TALENs), and the CRISPR-Cas9 gene editing systems. In particular embodiments of the present invention, HR involves double-stranded breaks induced by CRISPR-Cas9.

A "lysosomal storage disorder" or "LSD" refers to an inherited metabolic disease characterized by an abnormal build-up of various toxic materials in the body's cells as a result of enzyme deficiencies. There are nearly 50 of these disorders altogether, and they affect different parts of the body, including the skeleton, brain, skin, heart, and central nervous system. Non-limiting examples include Sphingolipidoses, Farber disease (ASAH1 deficiency), Krabbe disease (galactosylceramidase or GALC deficiency), Galactosialidosis, Gangliosidoses, Alpha-galactosidase, Fabry disease (α-galactosidase deficiency-GLA, or agalsidase alpha/beta), Schindler disease (alpha-NAGA deficiency), GM1 gangliosidosis, GM2 gangliosidoses (beta-hexosaminidase deficiency), Sandhoff disease (hexosaminidase-B deficiency), Tay-Sachs disease (hexosaminidase-A deficiency), Gaucher's disease Type 1/2/3 (glucocerebrosidase deficiency-gene name: GBA), Wolman disease (LAL deficiency), Niemann-Pick disease type A/B (sphingomyelin phosphodiesterase 1deficiency—SMPD1 or acid sphingomyelinase), Sulfatidosis, Metachromatic leukodystrophy, Hurler syndrome (alpha-L iduronidase deficiency—IDUA), Hunter syndrome or MPS2 (iduronate-2-sulfatase deficiency-idursulfase or IDS), Sanfilippo syndrome, Morquio, Maroteaux-Lamy syndrome, Sly syndrome (β-glucuronidase deficiency), Mucolipidosis, I-cell disease, Lipidosis, Neuronal ceroid lipofuscinoses, Batten disease (tripeptidyl peptidase-1 deficiency), Pompe (alglucosidase alpha deficiency), hypophosphatasia (asfotase alpha deficiency), MPS1 (laronidase deficiency), MPS3A (heparin N-sulfatase deficiency), MPS3B (alpha-N-acetylglucosaminidase deficiency), MPS3C (heparin-α-glucosaminide N-acetyltransferase deficiency), MPS3D (N-acetylglucosamine 6-sulfatase deficiency), MPS4 (elosulfase alpha deficiency), MPS6 (glasulfate deficiency), MPS7 (B-glucoronidase deficiency), phenylketonuria (phenylalanine hydroxylase deficiency), and MLD (arylsulphatase A deficiency). In particular embodiments, the LSD treated using the present methods and compositions is Mucopolysaccharidosis type 1, Gaucher Disease, or Krabbe Disease.

4. CRISPR/Cas Systems Targeting the CCR5 Safe Harbor Locus

The present disclosure provides methods and compositions for integrating and expressing transgenes encoding therapeutic proteins, e.g., therapeutic proteins such as iduronidase, glucocerebrosidase, or galactocerebrosidase, into the CCR5 safe harbor locus in cells from a subject with a lysosomal storage disorder (LSD). In particular embodiments, the cells are hematopoietic stem and progenitor cells (HSPCs) or neuronal stem cells. The cells can be modified using the methods described herein and then reintroduced into the subject, wherein the expression of the therapeutic protein in the modified cells in vivo can restore enzyme activity that is missing or deficient in the subject with the LSD.

The present invention is based in part on the identification of CRISPR guide sequences that specifically direct the cleavage of CCR5, e.g., within exon 3 of CCR5, by RNA-guided nucleases such as Cas9. In particular embodiments, the methods involve the introduction of ribonucleoproteins (RNPs) comprising an sgRNA targeting CCR5 and Cas9, as well as a template DNA molecule comprising CCR5 homology arms flanking the transgene encoding the therapeutic protein. Using the present methods, high rates of targeted integration at the CCR5 locus and expression of the therapeutic gene can be achieved, with the result that the transplantation and long-term engraftment of the modified cells can lead to a reduction or elimination of symptoms caused by the enzyme deficiency associated with the LSD.

sgRNAs

The single guide RNAs (sgRNAs) used in the present invention target the CCR5 locus. sgRNAs interact with a site-directed nuclease such as Cas9 and specifically bind to or hybridize to a target nucleic acid within the genome of a cell, such that the sgRNA and the site-directed nuclease co-localize to the target nucleic acid in the genome of the cell. The sgRNAs as used herein comprise a targeting sequence comprising homology (or complementarity) to a target DNA sequence at the CCR5 locus, and a constant region that mediates binding to Cas9 or another RNA-guided nuclease. The sgRNA can target any sequence within CCR5 adjacent to a PAM sequence. In some embodiments, the target sequence is within exon 3 of CCR5. In particular embodiments, the target sequence of the sgRNA comprises the sequence shown as SEQ ID NO: 3 or SEQ ID NO: 4. In particular embodiments, the sgRNA comprises the sequence shown as SEQ ID NO:5, or a sequence having, e.g., at least 90%, 91%, 92%, 93%, 94%, 95%, 96%, 97%, 98%, 99%, or more identity to SEQ ID NO:5, or comprising, e.g., 1, 2, 3 or more nucleotide substitutions in SEQ ID NO:5.

The targeting sequence of the sgRNAs may be, e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or 15-25, 18-22, or 19-21 nucleotides in length, and shares homology with a targeted genomic sequence, in particular at a position adjacent to a CRISPR PAM sequence. The sgDNA targeting sequence is designed to be homologous to the target DNA, i.e., to share the same sequence with the non-bound strand of the DNA template or to be complementary to the strand of the template DNA that is bound by the sgRNA. The homology or complementarity of the targeting sequence can be perfect (i.e., sharing 100% homology or 100% complementarity to the target DNA sequence) or the targeting sequence can be substantially homologous (i.e., having less than 100% homology or complementarity, e.g., with 1-4 mismatches with the target DNA sequence).

Each sgRNA also includes a constant region that interacts with or binds to the site-directed nuclease, e.g., Cas9. In the nucleic acid constructs provided herein, the constant region of an sgRNA can be from about 70 to 250 nucleotides in length, or about 75-100 nucleotides in length, 75-85 nucleotides in length, or about 80-90 nucleotides in length, or 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length. The overall length of the sgRNA can be, e.g., from about 80-300 nucleotides in length, or about 80-150 nucleotides in length, or about 80-120 nucleotides in length, or about 90-110 nucleotides in length, or, e.g, 90, 91, 92, 93, 94, 95, 96, 97, 98, 99, 100, 101, 102, 103, 104, 105, 106, 107, 108, 109, or 110 nucleotides in length.

It will be appreciated that it is also possible to use two-piece gRNAs (cr:tracrRNAs) in the present methods, i.e., with separate crRNA and tracrRNA molecules in which the target sequence is defined by the crispr RNA (crRNA), and the tracrRNA provides a binding scaffold for the Cas nuclease.

In some embodiments, the sgRNAs comprise one or more modified nucleotides. For example, the polynucleotide sequences of the sgRNAs may also comprise RNA analogs, derivatives, or combinations thereof. For example, the probes can be modified at the base moiety, at the sugar moiety, or at the phosphate backbone (e.g., phosphorothioates). In some embodiments, the sgRNAs comprise 3' phosphorothiate internucleotide linkages, 2'-O-methyl-3'-phosphoacetate modifications, 2'-fluoro-pyrimidines, S-constrained ethyl sugar modifications, or others, at one or more nucleotides. In particular embodiments, the sgRNAs comprise 2'-O-methyl-3'-phosphorothioate (MS) modifications at one or more nucleotides (see, e.g., Hendel et al. (2015) *Nat. Biotech.* 33(9):985-989, the entire disclosure of which is herein incorporated by reference). In particular embodiments, the 2'-O-methyl-3'-phosphorothioate (MS) modifications are at the three terminal nucleotides of the 5' and 3' ends of the sgRNA.

The sgRNAs can be obtained in any of a number of ways. For sgRNAs, primers can be synthesized in the laboratory using an oligo synthesizer, e.g., as sold by Applied Biosystems, Biolytic Lab Performance, Sierra Biosystems, or others. Alternatively, primers and probes with any desired sequence and/or modification can be readily ordered from any of a large number of suppliers, e.g., ThermoFisher, Biolytic, IDT, Sigma-Aldritch, GeneScript, etc.

RNA-Guided Nuclease

Any CRISPR-Cas nuclease can be used in the method, i.e., a CRISPR-Cas nuclease capable of interacting with a guide RNA and cleaving the DNA at the target site as defined by the guide RNA. In some embodiments, the nuclease is Cas9 or Cpf1. In particular embodiments, the nuclease is Cas9. The Cas9 or other nuclease used in the present methods can be from any source, so long that it is capable of binding to an sgRNA of the invention and being guided to and cleaving the specific CCR5 sequence targeted by the targeting sequence of the sgRNA. In particular embodiments, Cas9 is from *Streptococcus pyogenes.*

Also disclosed herein are CRISPR/Cas or CRISPR/Cpf1 systems that target and cleave DNA at the CCR5 locus. An exemplary CRISPR/Cas system comprises (a) a Cas (e.g., Cas9) or Cpf1 polypeptide or a nucleic acid encoding said polypeptide, and (b) an sgRNA that hybridizes specifically to CCR5, or a nucleic acid encoding said guide RNA. In some instances, the nuclease systems described herein, further comprises a donor template as described herein. In particular embodiments, the CRISPR/Cas system comprises an RNP comprising an sgRNA targeting CCR5 and a Cas protein such as Cas9. In some embodiments, the Cas9 is a high fidelity (HiFi) Cas9 (37).

In addition to the CRISPR/Cas9 platform (which is a type II CRISPR/Cas system), alternative systems exist including type I CRISPR/Cas systems, type III CRISPR/Cas systems, and type V CRISPR/Cas systems. Various CRISPR/Cas9 systems have been disclosed, including *Streptococcus pyogenes* Cas9 (SpCas9), *Streptococcus thermophilus* Cas9 (StCas9), *Campylobacter jejuni* Cas9 (CjCas9) and *Neisseria cinerea* Cas9 (NcCas9) to name a few. Alternatives to the Cas system include the *Francisella novicida* Cpf1 (FnCpf1), *Acidaminococcus* sp. Cpf1 (AsCpf1), and *Lachnospiraceae bacterium* ND2006 Cpf1 (LbCpf1) systems. Any of the above CRISPR systems may be used to induce a single or double stranded break at the CCR5 locus to carry out the methods disclosed herein.

Introducing the sgRNA and Cas Protein into Cells

The sgRNA and nuclease can be introduced into a cell using any suitable method, e.g., by introducing one or more polynucleotides encoding the sgRNA and the nuclease into the cell, e.g., using a vector such as a viral vector or delivered as naked DNA or RNA, such that the sgRNA and nuclease are expressed in the cell. In particular embodiments, the sgRNA and nuclease are assembled into ribonucleoproteins (RNPs) prior to delivery to the cells, and the RNPs are introduced into the cell by, e.g., electroporation. RNPs are complexes of RNA and RNA-binding proteins. In the context of the present methods, the RNPs comprise the RNA-binding nuclease (e.g., Cas9) assembled with the guide RNA (e.g., sgRNA), such that the RNPs are capable of binding to the target DNA (through the gRNA component of the RNP) and cleaving it (via the protein nuclease component of the RNP). As used herein, an RNP for use in the present methods can comprise any of the herein-described guide RNAs and any of the herein-described RNA-guided nucleases.

Animal cells, mammalian cells, preferably human cells, modified ex vivo, in vitro, or in vivo are contemplated. Also included are cells of other primates; mammals, including commercially relevant mammals, such as cattle, pigs, horses, sheep, cats, dogs, mice, rats; birds, including commercially relevant birds such as poultry, chickens, ducks, geese, and/or turkeys.

In some embodiments, the cell is an embryonic stem cell, a stem cell, a progenitor cell, a pluripotent stem cell, an induced pluripotent stem (iPS) cell, a somatic stem cell, a differentiated cell, a mesenchymal stem cell or a mesenchymal stromal cell, a neural stem cell, a hematopoietic stem cell or a hematopoietic progenitor cell, an adipose stem cell, a keratinocyte, a skeletal stem cell, a muscle stem cell, a fibroblast, an NK cell, a B-cell, a T cell, or a peripheral blood mononuclear cell (PBMC). In particular embodiments, the cells are hematopoietic stem and progenitor cells (HSPCs), e.g., cord blood-derived (CB) or adult peripheral blood-derived (PB) HSPCs, or neuronal stem cells.

To avoid immune rejection of the modified cells when administered to a subject, the cells to be modified are preferably derived from the subject's own cells. Thus, preferably the mammalian cells are autologous cells from the subject to be treated with the modified cells. In some embodiments, however, the cells are allogeneic, i.e., isolated from an HLA-matched or HLA-compatible, or otherwise suitable, donor.

In some embodiments, cells are harvested from the subject and modified according to the methods disclosed herein, which can include selecting certain cell types, optionally expanding the cells and optionally culturing the cells, and which can additionally include selecting cells that contain the transgene integrated into the CCR5 locus. In some embodiments, the cells are induced to undergo differentiation, e.g., into macrophages or monocytes, using methods known in the art and as described herein. In some embodiments, such modified, selected, and/or differentiated cells are then reintroduced into the subject.

Further disclosed herein are methods of using said nuclease systems to produce the modified host cells described herein, comprising introducing into the cell (a) an RNP of the invention that targets and cleaves DNA at the CCR5 locus, and (b) a homologous donor template or vector as described herein. Each component can be introduced into the cell directly or can be expressed in the cell by introducing a nucleic acid encoding the components of said one or more nuclease systems.

Such methods will target integration of the transgene encoding the therapeutic protein to the CCR5 locus in a host cell ex vivo. Such methods can further comprise (a) introducing a donor template or vector into the cell, optionally after expanding said cells, or optionally before expanding said cells, and (b) optionally culturing the cell.

In some embodiments, the disclosure herein contemplates a method of producing a modified mammalian host cell, the method comprising introducing into a mammalian cell: (a) an RNP comprising a Cas nuclease such as Cas9 and an sgRNA specific to the CCR5 locus, and (b) a homologous donor template or vector as described herein.

In any of these methods, the nuclease can produce one or more single stranded breaks within the CCR5 locus, or a double stranded break within the CCR5 locus. In these methods, the CCR5 locus is modified by homologous recombination with said donor template or vector to result in insertion of the transgene into the locus. The methods can further comprise (c) selecting cells that contain the transgene integrated into the CCR5 locus Techniques for insertion of transgenes, including large transgenes, capable of expressing functional proteins, including enzymes, cytokines, antibodies, and cell surface receptors are known in the art. (See, e.g. Bak and Porteus, Cell Rep. 2017 Jul. 18; 20(3): 750-756 (integration of EGFR); Kanojia et al., Stem Cells. 2015 October; 33(10): 2985-94 (expression of anti-Her2 antibody); Eyquem et al., Nature. 2017 Mar. 2; 543(7643):113-117 (site-specific integration of a CAR); O'Connell et al., 2010 PLoS ONE 5(8): e12009 (expression of human IL-7); Tuszynski et al., Nat Med. 2005 May; 11(5):551-5 (expression of NGF in fibroblasts); Sessa et al., Lancet. 2016 Jul. 30; 388(10043):476-87 (expression of arylsulfatase A in ex vivo gene therapy to treat MLD); Rocca et al., Science Translational Medicine 25 Oct. 2017: Vol. 9, Issue 413, eaaj2347 (expression of frataxin); Bak and Porteus, Cell Reports, Vol. 20, Issue 3, 18 Jul. 2017, Pages 750-756 (integrating large transgene cassettes into a single locus), Dever et al., Nature 17 Nov. 2016: 539, 384-389 (adding tNGFR into hematopoietic stem cells (HSC) and HSPCs to select and enrich for modified cells); each of which is hereby incorporated by reference in its entirety.)

Homologous Repair Templates

The transgene to be integrated is typically present within a homologous repair template, or homologous donor template. The transgene can be any transgene whose gene product has a beneficial effect in subjects with a lysosomal storage disorder. In particular embodiments, the transgene is used to replace or compensate for a defective or deficient gene, e.g., a defective iduronidase (IDUA) gene in a subject with Mucopolysaccharidosis type 1, a defective glucocerebrosidase (GBA) gene in a subject with Gaucher disease, or a defective galactocerebrosidase (GALC) gene in a subject with Krabbe disease.

In particular embodiments, the transgene is flanked in the template by CCR5 homology regions. For example, an exemplary template can comprise, in linear order: a first CCR5 homology region, a promoter, a coding sequence for a therapeutic protein, a polyA sequence such as a bovine growth hormone polyadenylation sequence (bGH-PolyA), and a second CCR5 homology region, where the first and second homology regions are homologous to the genomic sequences extending in either direction from the sgRNA target site. In particular embodiments, one of the homology regions comprises the sequence of SEQ ID NO:1, and the other homology region comprises the sequence of SEQ ID NO:2, and/or to a sequence having 60%, 65%, 70%, 75%, 80%, 85%, 90%, 95%, 96%, 97%, 98%, 99%, or greater identity to SEQ ID NO:1 and/or SEQ ID NO:2.

In one embodiment, for the treatment of mucopolysaccharidosis type 1, the therapeutic protein is iduronidase, and the promoter is the phosphoglycerate kinase (PGK) promoter or the spleen focus-forming virus (SFFV) promoter. This system can be used to modify any human cell. In particular embodiments, the system is used to genetically modify human CD34$^{+}$ hematopoietic stem and progenitor cells. In some embodiments, the homologous repair template comprises the sequence shown as SEQ ID NO: 6 or SEQ ID NO:7, or a derivative or fragment of SEQ ID NO:6 or SEQ ID NO:7, e.g., a sequence having 60%, 65%, 70%, 75%, 80%, 85%, 90%, 95%, 96%, 97%, 98%, 99%, or greater identity to SEQ ID NO:6 or SEQ ID NO:7 or to a fragment thereof.

In another embodiment, for the treatment of Gaucher disease, the protein is glucocerebrosidase, and the promoter is the CD68 promoter, e.g., the human CD68 promoter. In some embodiments, the promoter is a shortened derivative of the human CD68 promoter, with expression restricted to the monocyte/macrophage lineage. This system can be used to modify any human cell. In particular embodiments, the system is used to genetically modify human CD34$^+$ hematopoietic stem and progenitor cells. In some embodiments, the homologous repair template comprises the sequence shown as SEQ ID NO: 8, or a derivative or fragment of SEQ ID NO:8, e.g., a sequence having having 60%, 65%, 70%, 75%, 80%, 85%, 90%, 95%, 96%, 97%, 98%, 99%, or greater identity to SEQ ID NO:8 or to a fragment thereof.

In another embodiment, for the treatment of Krabbe disease, the protein is galactocerebrosidase, and the promoter is CD68, e.g., a shortened derivative of the human CD68 promoter with expression restricted to the monocyte/macrophage lineage. As such, expression of the enzyme can be induced primarily in monocytes/macrophages. This system can be used to modify any human cell. In particular embodiments, the system is used to genetically modify human neuronal stem cells or human CD34$^+$ hematopoietic stem and progenitor cells.

In addition to the promoters disclosed above, any promoter that can induce expression of the therapeutic protein in the modified cells can be used, including endogenous and heterologous promoters, inducible promoters, constitutive promoters, cell-specific promoters, and others. In some instances, in addition to the promoter, the transgene is optionally linked to one or more regulatory elements such as enhancers or post-transcriptional regulatory sequences. For example, one can include regulatory sequences (microRNA (miRNA) target sites) in the RNA to avoid expression in certain tissues (post-transcriptional targeting). In some instances, the expression control sequence functions to express the therapeutic transgene following the same expression pattern as in normal individuals (physiological expression) (See Toscano et al., Gene Therapy (2011) 18, 117-127 (2011), incorporated herein by reference in its entirety for its references to promoters and regulatory sequences).

Constitutive mammalian promoters include, but are not limited to, the promoters for the following genes: hypoxanthine phosphoribosyl transferase (HPTR), adenosine deaminase, pyruvate kinase, α-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of Moloney leukemia virus and other retroviruses, and the thymidine kinase promoter of herpes simplex virus. Commonly used promoters including the CMV (cytomegalovirus) promoter/enhancer, EF1a (elongation factor 1a), SV40 (simian virus 40), chicken β-actin and CAG (CMV, chicken β-actin, rabbit β-globin), Ubiquitin C and PGK, all of which provide constitutively active, high-level gene expression in most cell types. Other constitutive promoters are known to those of ordinary skill in the art.

Inducible promoters are activated in the presence of an inducing agent. For example, the metallothionein promoter is activated to increase transcription and translation in the presence of certain metal ions. Other inducible promoters include alcohol-regulated, tetracycline-regulated, steroid-regulated, metal-regulated, nutrient-regulated promoters, and temperature-regulated promoters.

Tissue-specific and/or physiologically regulated expression can also be pursued by modifying mRNA stability and/or translation efficiency (post-transcriptional targeting) of the transgenes. Alternatively, the incorporation of miRNA target recognition sites (miRTs) into the expressed mRNA has been used to recruit the endogenous host cell machinery to block transgene expression (detargeting) in specific tissues or cell types. miRNAs are noncoding RNAs, approximately 22 nucleotides, that are fully or partially complementary to the 3' UTR region of particular mRNA, referred to as miRTs. Binding of a miRNA to its particular miRTs promotes translational attenuation/inactivation and/or degradation. Regulation of expression through miRNAs is described in Geisler and Fechner, World J Exp Med. 2016 May 20, 6(2): 37-54; Brown and Naldini, Nat Rev Genet. 2009 August, 10(8):578-85; Gentner and Naldini, Tissue Antigens. 2012 November, 80(5):393-403.

To facilitate homologous recombination, the transgene is flanked within the polynucleotide or donor construct by sequences homologous to the target genomic sequence, i.e., CCR5. In particular, the transgene is flanked by sequences surrounding the site of cleavage as defined by sgRNA. In a particular embodiment, the transgene is flanked on one side by a sequence comprising SEQ ID NO:1 or a fragment thereof, and on the other side by a sequence comprising SEQ ID NO:2 or a fragment thereof. The homology regions can be of any size, e.g., 50-2000, 100-1500 bp, 300-900 bp, 400-600 bp, or about 50, 100, 200, 300, 400, 410, 420, 430, 440, 450, 460, 470, 480, 490, 500, 510, 520, 530, 540, 550, 560, 570, 580, 590, 600, 700, 800, 900, 1000, 1100, 1200, 1300, 1400, 1500 or more bp.

Any suitable method can be used to introduce the polynucleotide, or donor construct, into the cell. In particular embodiments, the polynucleotide is introduced using a recombinant adeno-associated viral vector (rAAV). For example, the rAAV can be from serotype 1 (e.g., an rAAV1 vector), 2 (e.g., an rAAV2 vector), 3 (e.g., an rAAV3 vector), 4 (e.g., an rAAV4 vector), 5 (e.g., an rAAV5 vector), 6 (e.g., an rAAV6 vector), 7 (e.g., an rAAV7 vector), 8 (e.g., an rAAV8 vector), 9 (e.g., an rAAV9 vector), 10 (e.g., an rAAV10 vector), or 11 (e.g., an rAAV11 vector). In particular embodiments, the vector is an rAAV6 vector. In some instances, the donor template is single stranded, double stranded, a plasmid or a DNA fragment. In some instances, plasmids comprise elements necessary for replication, including a promoter and optionally a 3' UTR.

Further disclosed herein are vectors comprising (a) one or more nucleotide sequences homologous to the CCR5 locus, and (b) a transgene encoding a therapeutic factor of the invention. The vector can be a viral vector, such as a retroviral, lentiviral (both integration competent and integration defective lentiviral vectors), adenoviral, adeno-associated viral or herpes simplex viral vector. Viral vectors may further comprise genes necessary for replication of the viral vector.

In some embodiments, the targeting construct comprises: (1) a viral vector backbone, e.g. an AAV backbone, to generate virus; (2) arms of homology to the target site of at least 200 bp but ideally at least 400 bp on each side to assure high levels of reproducible targeting to the site (see, Porteus, Annual Review of Pharmacology and Toxicology, Vol. 56:163-190 (2016); which is hereby incorporated by reference in its entirety); (3) a transgene encoding a therapeutic protein and capable of expressing the therapeutic protein; (4) an expression control sequence operably linked to the transgene; and optionally (5) an additional marker gene to allow for enrichment and/or monitoring of the modified host cells. Any AAV known in the art can be used. In some embodiments the primary AAV serotype is AAV6.

Suitable marker genes are known in the art and include Myc, HA, FLAG, GFP, truncated NGFR, truncated EGFR, truncated CD20, truncated CD19, as well as antibiotic resistance genes (e.g., pac (puromycin-N-acetyl transferase), aph (aminoglycoside phosphotransferase), or bsd (blasticidin S deaminase), providing resistance to puromycin, G418, and blasticidin, respectively).

In any of the preceding embodiments, the donor template or vector comprises a nucleotide sequence homologous to a fragment of the CCR5 locus, optionally to the sequences shown as SEQ ID NO:1 and/or SEQ ID NO:2 or fragments thereof, wherein the nucleotide sequence is at least 60%, 65%, 70%, 75%, 80%, 85%, 88%, 90%, 92%, 95%, 98%, or 99% identical to at least 100, 150, 200, 250, 300, 350, 400, 450, 500, 550, 600, 650, 700, 750, 800, 850, 900, 1000 or more consecutive nucleotides of the CCR5 locus, e.g., to SEQ ID NO:1 and/or SEQ ID NO:2.

The inserted construct can also include other safety switches, such as a standard suicide gene into the locus (e.g. iCasp9) in circumstances where rapid removal of cells might be required due to acute toxicity. The present disclosure provides a robust safety switch so that any engineered cell transplanted into a body can be eliminated, e.g., by removal of an auxotrophic factor. This is especially important if the engineered cell has transformed into a cancerous cell.

5. Methods of Treatment

Following the integration of the transgene into the genome of the cell, e.g., HSPC, and confirming expression of the encoded therapeutic protein, a plurality of modified cells can be reintroduced into the subject, such that they can repopulate and differentiate into, e.g., macrophages or monocytes, and due to the expression of the integrated transgene, can improve one or more abnormalities or symptoms in the subject with the LSD. In some embodiments, the cells are expanded, selected, or induced to undergo differentiation, prior to reintroduction into the subject.

Disclosed herein, in some embodiments, are methods of treating an LSD in an individual in need thereof, the method comprising providing to the individual enzyme replacement therapy using the genome modification methods disclosed herein. In some instances, the method comprises a modified host cell ex vivo, comprising a transgene encoding an enzyme, i.e., therapeutic protein, integrated at the CCR5 locus, wherein said modified host cell expresses an enzyme that is deficient in the individual, thereby treating the LSD in the individual. In some instances, the enzyme is iduronidase, e.g., when the subject has mucopolysaccharidosis type 1. In some instances, the enzyme is glucocerebrosidase, e.g., when the subject has Gaucher disease. In some instances, the enzyme is galactocerebrosidase, e.g. when the subject has Krabbe disease.

In some embodiments, the genetically modified cells express the therapeutic protein (e.g. iduronidase, glucocerebrosidase, or galactocerebrosidase) at a level that is at least, e.g., about 10%, 20%, 30%, 40%, 50%, 60%, 70%, 80%, 90%, 100%, 110%, 120%, 130%, 140%, 150%, 160%, 170%, 180%, 190%, 200%, or more or more of a level representative of a healthy individual without an LSD. In some embodiments, tissues of the subject, e.g., in plasma, liver, spleen, brain, comprise an enzymatic activity provided by the genetically modified transplanted cells, that is at least about 10%, 20%, 30%, 40%, 50%, 60%, 70%, 80%, 90%, 100%, 110%, 120%, 130%, 140%, 150%, 160%, or more of a level representative of a healthy individual without an LSD.

In some embodiments, the guide RNA displays off-target activity (e.g., >0.1% indels) at less than 10, 9, 8, 7, 6, 5, 4, 3, 2, or 1 location. In particular embodiments, the off-target activity occurs at less than 4, 3, 2, or 1 location. In particular embodiments, the off-target activity occurs at 1 or 0 locations when a HiFi Cas9 is used.

In some embodiments, following introduction of the guide RNA, RNA-guided nuclease, and donor template, at least about 5%, 10%, 15%, 20%, 25%, 30%, 35%, 40%, 45%, 50%, 55%, 60%, 65%, 70%, 75%, 80%, 85%, 90%, or more of the targeted cells comprise an integrated transgene. In some embodiments, following transplantation of the genetically modified cells, chimerism in the subject is at least about 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or more (e.g., 100%).

Pharmaceutical Compositions

Disclosed herein, in some embodiments, are methods, compositions and kits for use of the modified cells, including pharmaceutical compositions, therapeutic methods, and methods of administration. Although the descriptions of pharmaceutical compositions provided herein are principally directed to pharmaceutical compositions which are suitable for administration to humans, it will be understood by the skilled artisan that such compositions are generally suitable for administration to any animals.

In some embodiments, a pharmaceutical composition comprising a modified autologous host cell of the invention is provided. The modified autologous host cell is genetically engineered to comprise an integrated transgene encoding the therapeutic protein at the CCR5 locus. The modified host cell of the disclosure herein may be formulated using one or more excipients to, e.g.: (1) increase stability; (2) alter the biodistribution (e.g., target the cell line to specific tissues or cell types); (3) alter the release profile of an encoded therapeutic factor.

Formulations of the present disclosure can include, without limitation, saline, liposomes, lipid nanoparticles, polymers, peptides, proteins, and combinations thereof. Formulations of the pharmaceutical compositions described herein may be prepared by any method known or hereafter developed in the art of pharmacology. As used herein the term "pharmaceutical composition" refers to compositions including at least one active ingredient (e.g., a modified host cell) and optionally one or more pharmaceutically acceptable excipients. Pharmaceutical compositions of the present disclosure may be sterile.

Relative amounts of the active ingredient (e.g. the modified host cell), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may include between 0.1% and 99% (w/w) of the active ingredient. By way of example, the composition may include between 0.1% and 100%, e.g., between 0.5 and 50%, between 1-30%, between 5-80%, or at least 80% (w/w) active ingredient.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, MD, 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Injectable formulations may be sterilized, for example, by filtration through a bacterial-retaining filter, and/or by incorporating sterilizing agents in the form of sterile solid compositions which can be dissolved or dispersed in sterile water or other sterile injectable medium prior to use.

Dosing and Administration

The modified host cells of the present disclosure included in the pharmaceutical compositions described above may be administered by any delivery route, systemic delivery or local delivery, which results in a therapeutically effective outcome. These include, but are not limited to, enteral, gastroenteral, epidural, oral, transdermal, intracerebral, intracerebroventricular, epicutaneous, intradermal, subcutaneous, nasal, intravenous, intra-arterial, intramuscular, intracardiac, intraosseous, intrathecal, intraparenchymal, intraperitoneal, intravesical, intravitreal, intracavernous), interstitial, intra-abdominal, intralymphatic, intramedullary, intrapulmonary, intraspinal, intrasynovial, intrathecal, intratubular, parenteral, percutaneous, periarticular, peridural, perineural, periodontal, rectal, soft tissue, and topical. In particular embodiments, the cells are transplanted intrafemorally or intrahepatically. In certain embodiments, the composition may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

In some embodiments, a subject will undergo a conditioning regime before cell transplantation. For example, before hematopoietic stem cell transplantation, a subject may undergo myeloablative therapy, non-myeloablative therapy or reduced intensity conditioning to prevent rejection of the stem cell transplant even if the stem cell originated from the same subject. The conditioning regime may involve administration of cytotoxic agents. The conditioning regime may also include immunosuppression, antibodies, and irradiation. Other possible conditioning regimens include antibody-mediated conditioning (see, e.g., Czechowicz et al., 318(5854) Science 1296-9 (2007); Palchaudari et al., 34(7) Nature Biotechnology 738-745 (2016); Chhabra et al., 10:8(351) Science Translational Medicine 351ra105 (2016)) and CAR T-mediated conditioning (see, e.g., Arai et al., 26(5) Molecular Therapy 1181-1197 (2018); each of which is hereby incorporated by reference in its entirety). For example, conditioning needs to be used to create space in the brain for microglia derived from engineered hematopoietic stem cells (HSCs) to migrate in to deliver the protein of interest (as in recent gene therapy trials for ALD and MLD). The conditioning regimen is also designed to create niche "space" to allow the transplanted cells to have a place in the body to engraft and proliferate. In HSC transplantation, for example, the conditioning regimen creates niche space in the bone marrow for the transplanted HSCs to engraft. Without a conditioning regimen, the transplanted HSCs cannot engraft.

Certain aspects of the present disclosure are directed to methods of providing pharmaceutical compositions including the modified host cell of the present disclosure to target tissues of mammalian subjects, by contacting target tissues with pharmaceutical compositions including the modified host cell under conditions such that they are substantially retained in such target tissues. In some embodiments, pharmaceutical compositions including the modified host cell include one or more cell penetration agents, although "naked" formulations (such as without cell penetration agents or other agents) are also contemplated, with or without pharmaceutically acceptable excipients.

The present disclosure additionally provides methods of administering modified host cells in accordance with the disclosure to a subject in need thereof. The pharmaceutical compositions including the modified host cell, and compositions of the present disclosure may be administered to a subject using any amount and any route of administration effective for preventing, treating, or managing the LSD. The exact amount required will vary from subject to subject, depending on the species, age, and general condition of the subject, the severity of the disease, the particular composition, its mode of administration, its mode of activity, and the like. The subject may be a human, a mammal, or an animal. The specific therapeutically or prophylactically effective dose level for any particular individual will depend upon a variety of factors including the disorder being treated and the severity of the disorder; the activity of the specific payload employed; the specific composition employed; the age, body weight, general health, sex and diet of the patient; the time of administration, route of administration; the duration of the treatment; drugs used in combination or coincidental with the specific modified host cell employed; and like factors well known in the medical arts.

In certain embodiments, modified host cell pharmaceutical compositions in accordance with the present disclosure may be administered at dosage levels sufficient to deliver from, e.g., about $1\times10^4$ to $1\times10^5$, $1\times10^5$ to $1\times10^6$, $1\times10^6$ to $1\times10^7$, or more modified cells to the subject, or any amount sufficient to obtain the desired therapeutic or prophylactic, effect. The desired dosage of the modified host cells of the present disclosure may be administered one time or multiple times. In some embodiments, delivery of the modified host cell to a subject provides a therapeutic effect for at least 1 day, 2 days, 3 days, 4 days, 5 days, 6 days, 7 days, 1 week, 2 weeks, 3 weeks, 4 weeks, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years.

The modified host cells may be used in combination with one or more other therapeutic, prophylactic, research or diagnostic agents, or medical procedures, either sequentially or concurrently. In general, each agent will be administered at a dose and/or on a time schedule determined for that agent.

Use of a modified mammalian host cell according to the present disclosure for treatment of a lysosomal disease, disorder or condition is also encompassed by the disclosure.

The present disclosure also contemplates kits comprising compositions or components of the invention, e.g., sgRNA, Cas9, RNPs, and/or homologous templates, as well as, optionally, reagents for, e.g., the introduction of the components into cells. The kits can also comprise one or more containers or vials, as well as instructions for using the compositions in order to modify cells and treat subjects according to the methods described herein.

6. Examples

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1. Human Genome-Edited Hematopoietic Stem Cells Phenotypically Correct Mucopolysaccharidosis Type I

Abstract

Lysosomal enzyme deficiencies comprise a large group of genetic disorders that generally lack effective treatments. A potential treatment approach is to engineer the patient's own hematopoietic system to express high levels of the deficient enzyme, thereby correcting the biochemical defect and halting disease progression. Here, we present an efficient ex vivo genome editing approach using CRISPR-Cas9 that targets the lysosomal enzyme iduronidase to the CCR5 safe harbor locus in human CD34$^+$ hematopoietic stem and progenitor cells (HSPCs). The modified cells secrete supra-endogenous enzyme levels, maintain long-term repopulation and multi-lineage differentiation potential, and can improve biochemical and phenotypic abnormalities in an immunocompromised mouse model of Mucopolysaccharidosis type I. These studies provide support for the development of genome-edited CD34$^+$ hematopoietic stem and progenitor cells as a potential treatment for Mucopolysaccharidosis type I. The safe harbor approach constitutes a flexible platform for the expression of lysosomal enzymes making it applicable to other lysosomal storage disorders.

Introduction

The present example describes the development of an exemplary in vivo genome editing approach for MPSI. We use CCR5 as the target safe harbor to insert an expression cassette to overexpress IDUA in human CD34$^+$ HPSCs and their progeny. CCR5 is considered a non-essential gene because bi-allelic inactivation of CCR5 (CCR5Δ32) has no general detrimental impact on human health, and the only known phenotypes of CCR5 loss are resistance to HIV-1 infection and increased susceptibility to West Nile virus (19). We report that human HSPCs modified using genome editing to express IDUA from the CCR5 locus engraft and ameliorate biochemical, visceral, musculoskeletal, and neurologic manifestations of the disease in a new immunocompromised model of MSPI.

Results

Efficient Targeting of IDUA to the CCR5 Locus in Human HSPCs

Figures 7A, 7B, 7C, 7D:
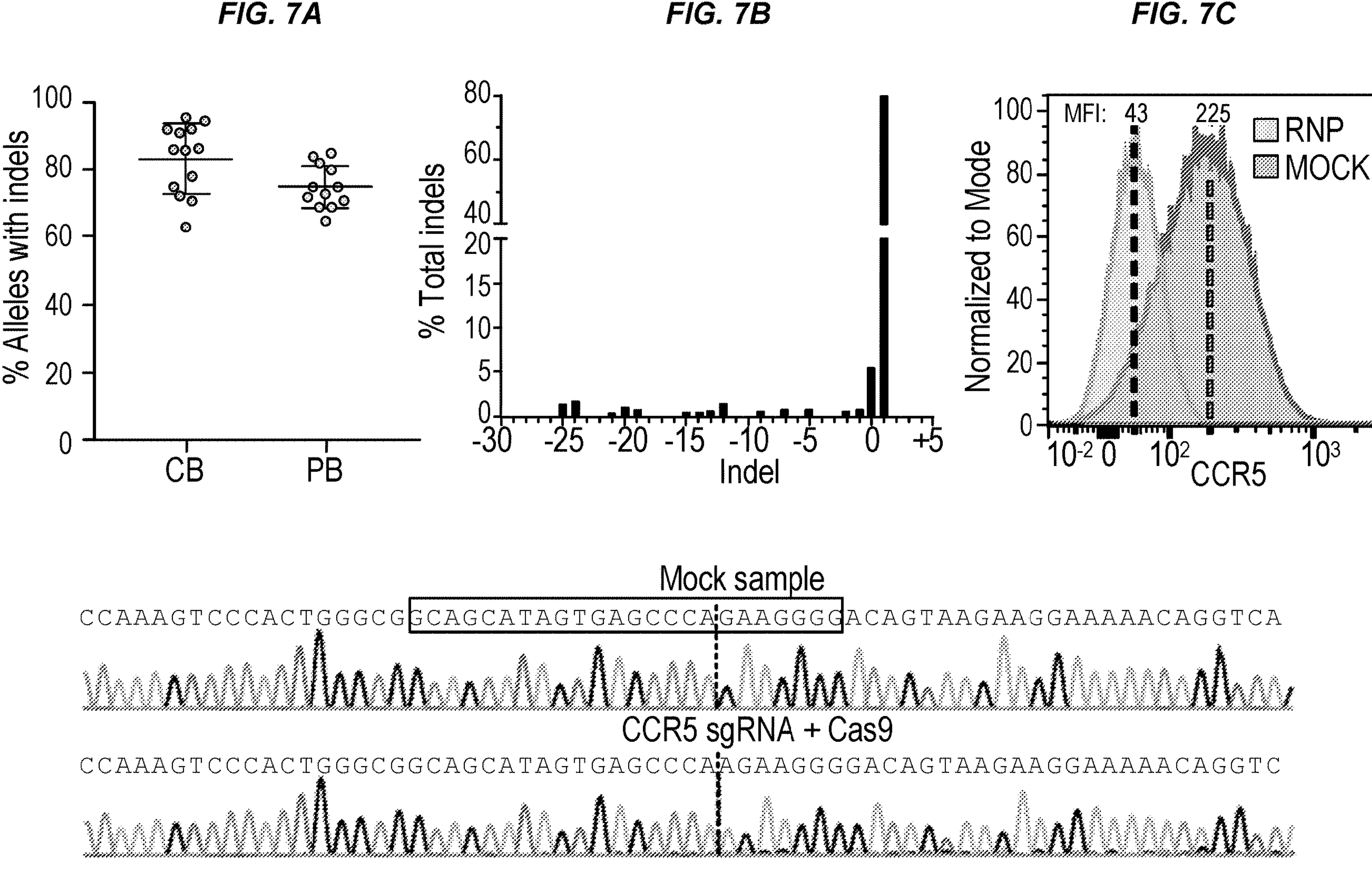
Figures 10A, 10B, 10C, 10D, 10E, 10F:
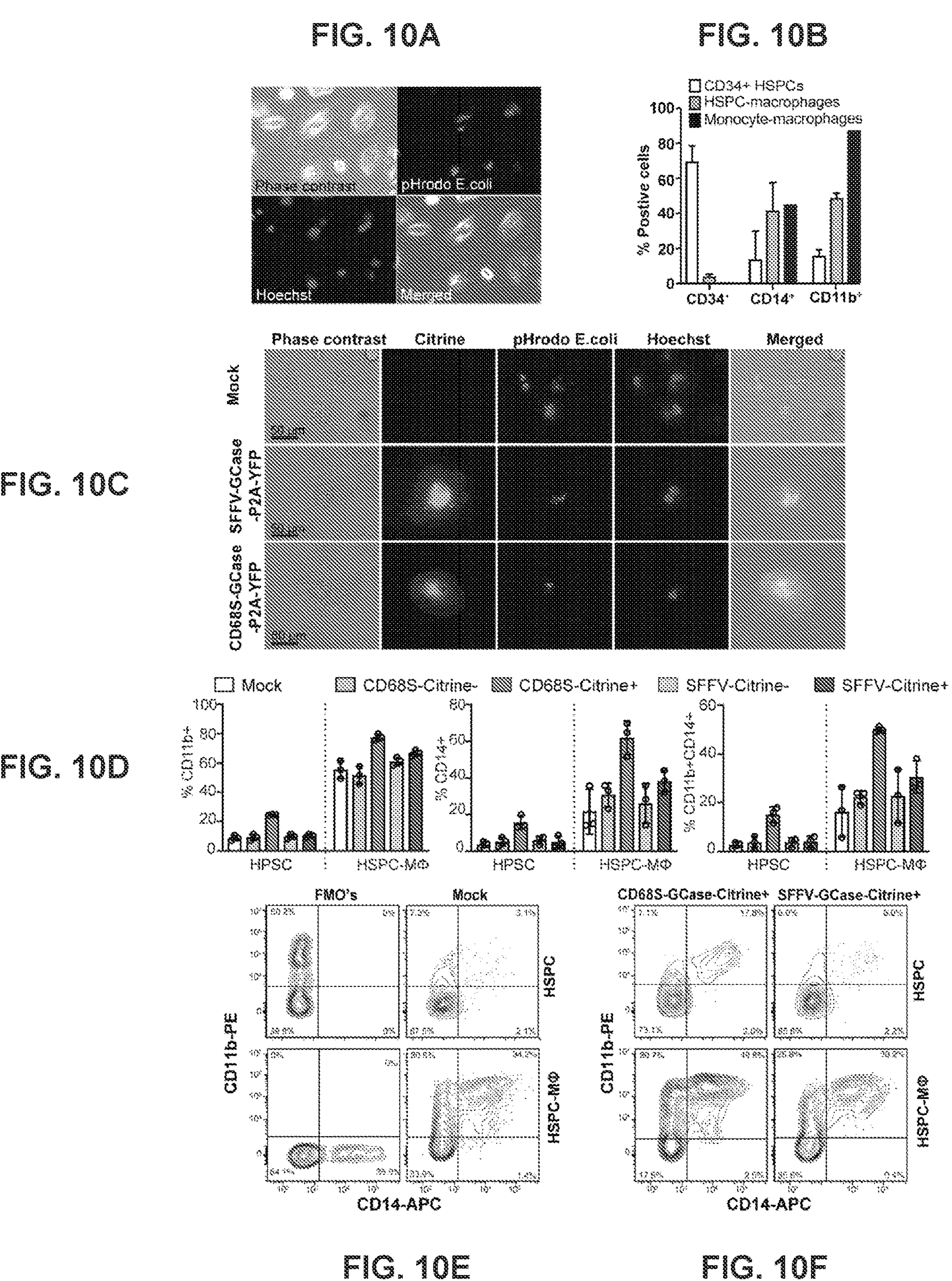
FIGS. 10A-10F. Generation of human GCase-macrophages from genome edited HSPCs

To generate human CD34$^+$ HPSCs overexpressing IDUA, we used sgRNA/Cas9 ribonucleoprotein (RNP) and adeno-associated viral vector serotype six (AAV6) delivery of the homologous templates (20). RNP complexes consisting of 2'-O-methyl 3'phosphorothioate-modified CCR5 sgRNA (21) and Cas9 protein were electroporated into cord blood-derived (CB) and adult peripheral blood-derived HSPCs (PB). The efficiency of double-strand DNA break (DSB) generation by our CCR5 RNP complex was estimated by measuring the frequency of insertions/deletions (Indel) at the predicted cut site. The mean Indel frequencies were 83%±8 (±SD) in CB-HSPCs and 76%±8 in PB-HSPCs, consistent with a highly active sgRNA. The predominant Indel was a single A/T insertion that abrogated CCR5 protein expression (FIG. 7) (22).

To achieve precise genetic modification, the templates for homologous recombination were made by inserting IDUA expression cassettes driven by the spleen focus-forming virus (SFFV) or the phosphoglycerate kinase (PGK) promoter, followed by a yellow fluorescent protein (YFP) downstream of the self-cleaving P2A peptide into the AAV vector genome. A third expression cassette containing IDUA driven by PGK but without a selection marker was also made (FIG. 1A). These strong constitutive promoters were chosen to harness the ability of all hematopoietic lineages to express IDUA and maximize biochemical cross-correction, and because IDUA expression was previously shown not be toxic to HSPCs. Following electroporation, CB and PB cells transduced with the SFFV-IDUA-YFP and PGK-IDUA-YFP viruses were examined for YFP fluorescence to quantify the efficiency of modification. As shown in FIG. 1B, RNP electroporation followed by AAV6 transduction lead to a marked increase in the median fluorescence intensity of the cells. As previously reported, this shift in the fluorescence intensity allows for the identification of cells that have successfully undergone HR-GE18. In CB-derived HSPCs the mean fraction of YFP-positive cells, was 34% 7 and 32%±8 with SFFV and PGK-driven expression cassettes, respectively. In PB-HSPCs, the frequencies were 21%±5, and 24%±5 for the same AAV6 donors (FIG. 1C). AAV6 transduction alone showed <2% YFP-positive cells, while mock cells that underwent electroporation but not AAV transduction had no detectable fluorescence. We measured the efficiency of modification in CB and PB cells transduced with the PGK-IDUA virus lacking the reporter (PGK-IDUA) by genotyping single cell-derived colonies from colony formation assays (CFAs) (FIGS. 8A-8B). In these cells, the frequencies of modification were 54%±10, and 44% 7 in CB and PB-HSPCs, considerably higher than the larger, YFP-containing cassettes, suggesting that efficiency is dependent on insert size (FIG. 1C). Based on these targeting frequencies we conclude that our genome editing protocol is efficient and reproducible for human CB and PB-derived HSPCs.

We also characterized the genomic modifications at CCR5 loci, by quantifying the fraction of targeted alleles in bulk DNA preparations using droplet-digital PCR (ddPCR) (FIGS. 8C, 8D). This data allowed us to estimate the distribution of cells with one (mono-allelic) or two (bi-allelic) alleles targeted in different cell donor samples and indicated that, for the YFP constructs, 65-100% of the cells had mono-allelic modification. Consistent with this, genotyping of YFP-positive colonies in CFAs showed a mean mono-allelic modification frequency of 80%±7.5 (FIG. 1D).

High IDUA Expression in Edited HSPCs and Derived Macrophages

Figures 2A, 2B, 2C, 2D, 2E, 2F:
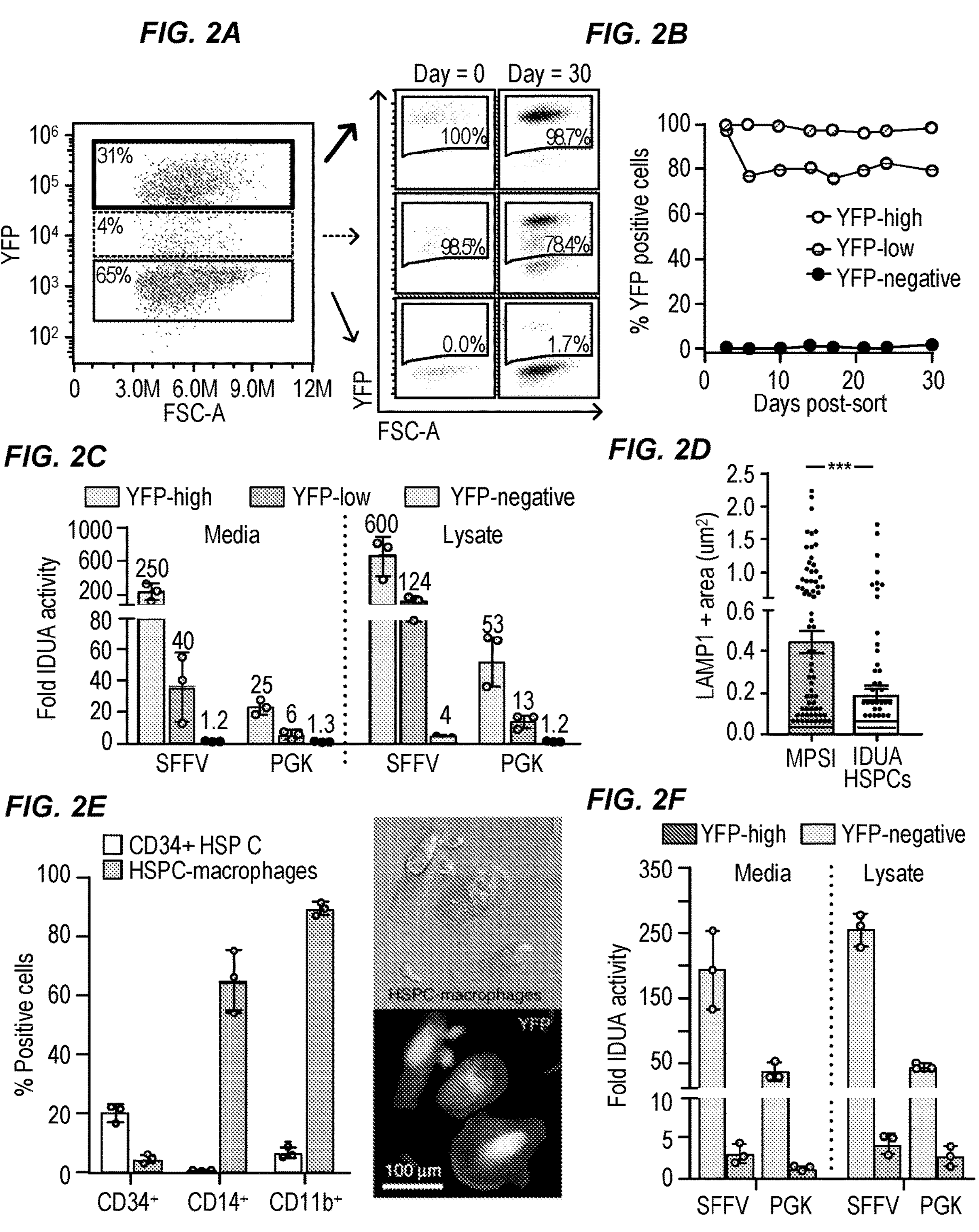
FIG. 2A: Representative FACS plot showing three distinct populations based on YFP expression 3 days post-modification.
FIG. 2B: Percent YFP-positive cells in culture (30 days).
FIG. 2C: Fold increase in IDUA secretion and intracellular expression by YFP-high, YFP-low, and YFP-negative populations compared to mock cells.
FIG. 2D: Average LAMP-1+area in MPSI fibroblasts co-cultured with IDUA-HSPCs. Each dot represents a cell.
FIG. 2E: Human CD34, CD14, and CD11b marker expression in HSPC-derived macrophages after in vitro differentiation compared to undifferentiated cells ($CD34^+$ HSPCs). Macrophage morphology and YFP expression after differentiation.
FIG. 2F: Fold increase in IDUA secretion and intracellular expression in HSPC-macrophages modified with SFFV and PGK expression cassettes.
Figures 4A, 4B, 4C, 4D, 4E, 4F:
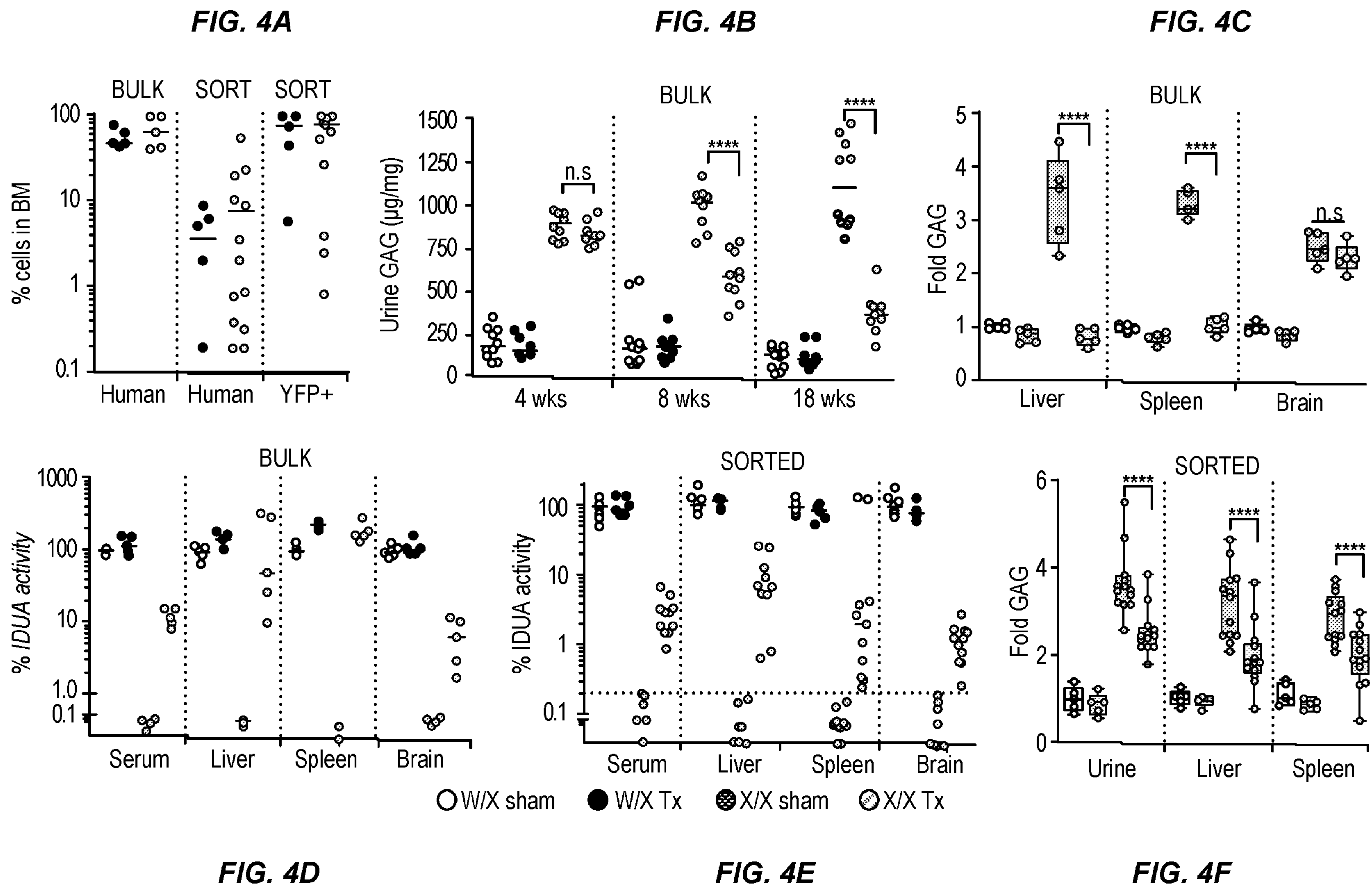
FIGS. 4A-4F. Biochemical correction in NSG-IDUAX/X mice by human IDUA-HSPCs. IDUA activity and GAG accumulation in heterozygous sham-treated (W/X sham− clear), heterozygous transplanted (W/X Tx− black), homozygous sham-treated (X/X sham− blue), and homozygous transplanted (X/X Tx− red) mice.
Figures 5A, 5B, 5C, 5D, 5E:
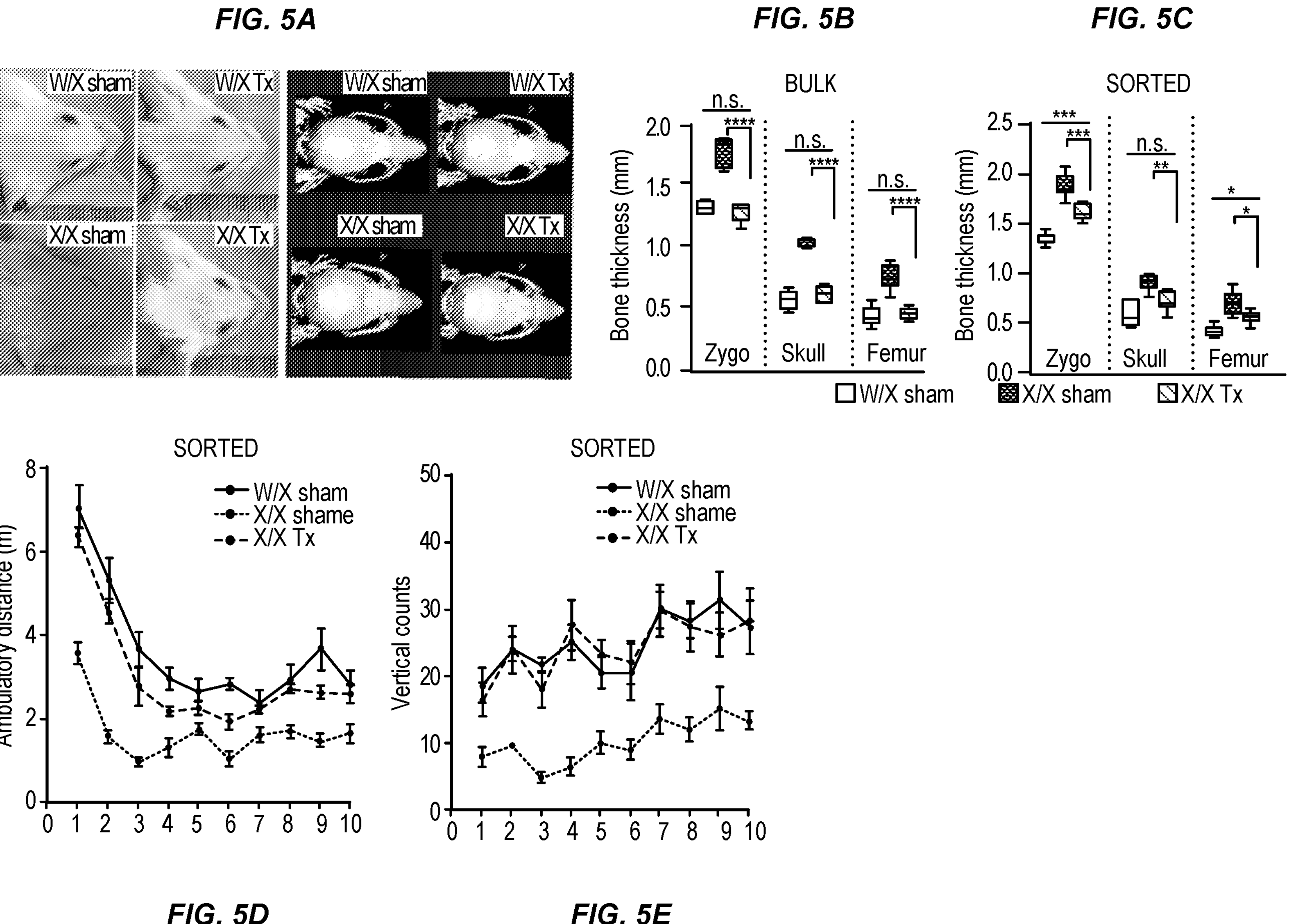
FIGS. 5A-5I. Phenotypic reconstitution in NSG-IDUAX/X mice by human IDUA-HSPCs.
Figures 5F, 5G, 5H, 5I:
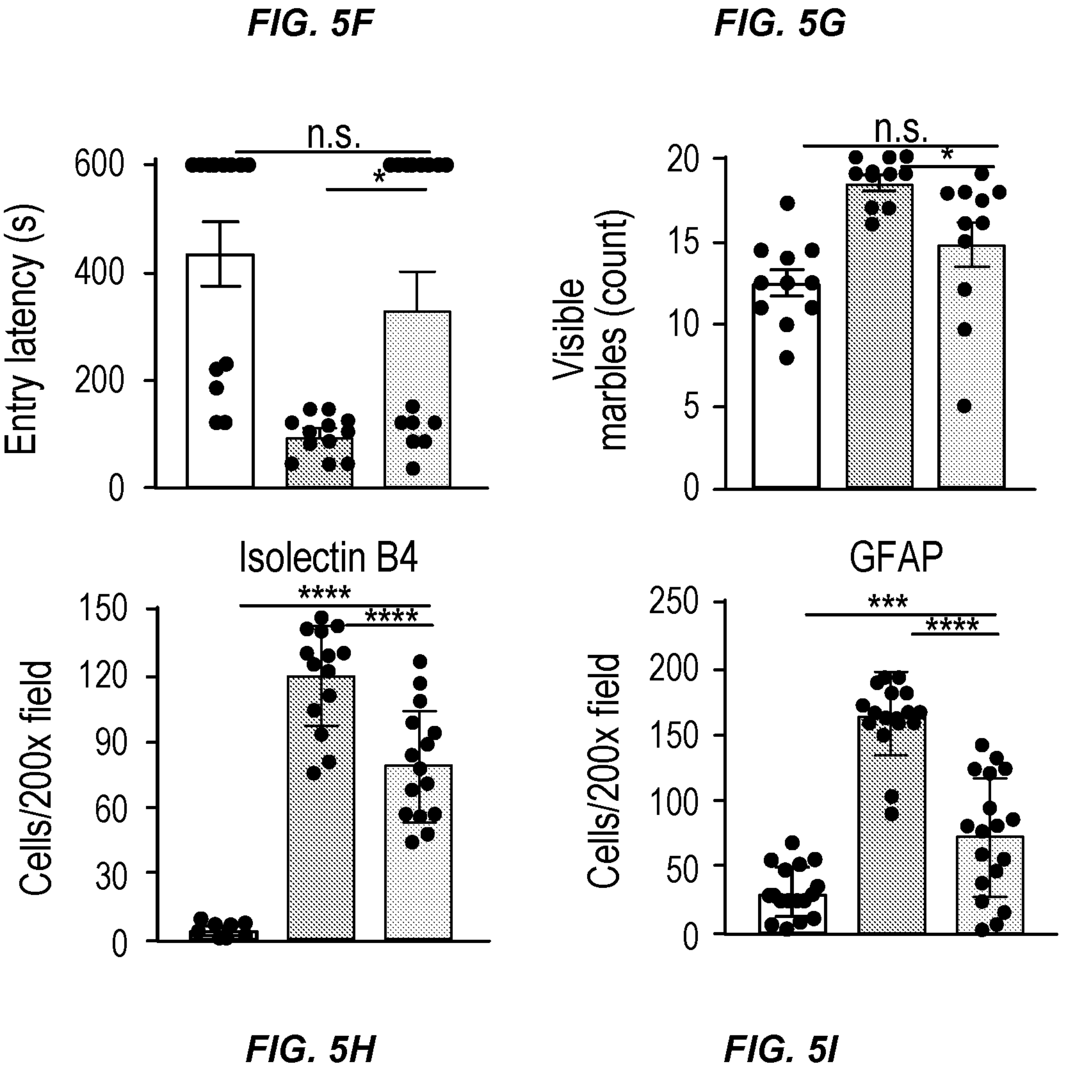
Figure 6:
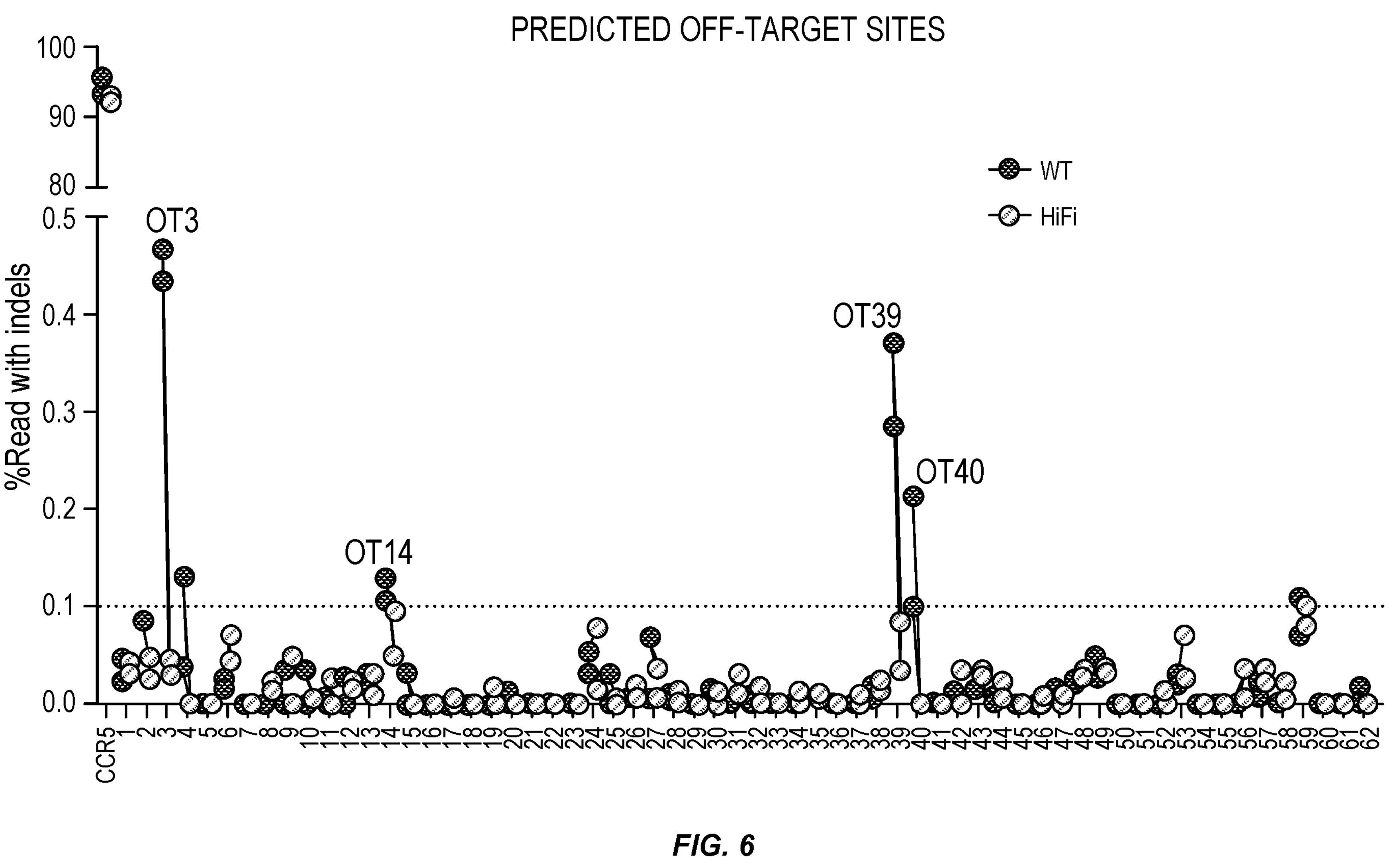

A central concept in our approach is that HSPCs and their progeny will secrete stable, supra-endogenous IDUA levels that can cross-correct the lysosomal defect in affected cells. Examination of modified HSPCs in culture showed that 3 days post-modification, three distinct cell populations could be discerned based on YFP expression: high/medium/low (FIG. 2A). YFP-high cells exhibited persistent fluorescence in culture for at least 30 days, demonstrating stable integration of the cassettes. YFP-negative cells had no detectable YFP expression at the time of selection, though approximately 1% of cells eventually became positive. Most cells with intermediate fluorescence converted to YFP-high (80%) (FIG. 2B). In these cultures, where YFP-positive and negative cells were mixed and grown under expansion conditions, the fraction of YFP-positive cells remained stable for 30 days, suggesting that neither the modification, nor the overexpression of the enzyme, nor reporter expression in vitro impacted the cells' proliferative potential.

When compared to mock-treated cells expressing endogenous IDUA levels, YFP− high cells secreted 250 and 25-fold more enzyme for the SFFV and PGK-driven cassettes respectively, while cell lysates expressed 600 and 50-fold more enzymatic activity (FIG. 2C). Not surprisingly, the SSFV promoter was able to drive substantially higher IDUA expression compared to PGK. When YFP-high IDUA-HSPCs were co-cultured with patient-derived MPSI fibroblasts, they led to a decrease in the average area of lysosomal-associated membrane protein 1 (LAMP-1) positive specks, consistent with reduced lysosomal compartment size and cross-correction of the cellular phenotype (FIG. 2D). These data confirm that IDUA-HSPCs secrete supra-physiological IDUA levels and that the secreted IDUA has the post-translational modifications required for uptake into MPSI cells and cellular cross-correction.

For IDUA-HSPCs to successfully correct biochemical abnormalities in the organs affected in MPSI, they must differentiate into monocytes that will migrate to and differentiate suggest that our CCR5 sgRNA combined with either WT Cas9 or especially HiFi Cas9 has negligible off-target activity on a large screen of bioinformatically predicted sites.

TABLE 1

Summary of off-target sites (OT's) above level of detection (>0.1%). PAM sequences are shown as bold and mismatched bases are shown as italics. For all of these sites the percent of Indels was <0.5% using wild type (WT) Cas9. For 4 of these sites, the use of the HiFi Cas9 abolished off-target activity

| | | | | | | | | |
|---|---|---|---|---|---|---|---|---|
| CCR5 | GCAGCATAGTGAGCCCAGA **AGGG** (SEQ ID NO: 3) | CCR5 | Exon | 0.128 | 93.41 | 95.832 | 92.377 | 93.078 |
| CCR5_OT3 | ACAGAATAGAGAGCCCAGA **AAGG** (SEQ ID NO: 9) | GRID1 | Intergenic | 0 | 0.467 | 0.434 | 0.03 | 0.045 |
| CCR5_OT14 | ACAGCATAGAGGGCCCAGA **AGGG** (SEQ ID NO: 10) | SUOX | Exon | 0 | 0.105 | 0.128 | 0.095 | 0.051 |
| CCR5_OT39 | ACAGCATAGTGAACCCAGGA **GGG** (SEQ ID NO: 11) | TBPL2 | Intergenic | 0.017 | 0.388 | 0.302 | 0.102 | 0.052 |
| CCR5_OT40 | GCTGCATAGTGAACCCAGTA **TGG** (SEQ ID NO: 12) | ZNF609 | Intergenic | 0.032 | 0.122 | 0.245 | 0.031 | 0.014 |

Several studies have shown that in primary cells, Cas9-mediated DSBs result in p53-mediated cell cycle arrest, thereby decreasing the efficiency of HR-GE (38,39). Consequently, concerns have been raised about the potential for enrichment of p53 negative clones when selecting cells that have successfully undergone HR-GE. To examine p53 function in our cells, we targeted four biological samples (two CB and two PB-derived) to express the PGK-IDUA-YFP cassette and separated mock, YFP+ (cells that underwent HR-GE), and YFP− (cells that did not undergo HR-GE). Because p53− clones could be a rare population with a growth advantage, to increase the probability of detection the cells were allowed to expand 100-150-fold (~2 weeks). We first sequenced all TP53 exons (NM_000546.5) in the three conditions in all four samples using a clinically validated, next-generation sequencing assay. No new TP53 sequence variants were found in the HR-GE+ cells despite in vitro expansion. Consistent with this, after treatment with the DNA double-strand break inducer doxorubicin, mock, HR-GE+, and HR-GE− cells had undisguisable responses when assayed for p53 activation, as measured by p53 protein stabilization by FACs, and transcriptional activation of seven p53 targets genes as measured by qPCR.

Collectively, we performed 200 autopsies (101 mice used in primary engraftment, 50 in secondary engraftment, and 49 in NSG-IDUAX/X correction studies) in which no gross tumors were found. Three tumor-like masses were evaluated by histology and confirmed to be Electroporation and Transduction of Cells CCR5 sgRNA was purchased from TriLink BioTechnologies (San Diego, CA, USA) and was previously reported (22). The sgRNA was chemically modified with three terminal nucleotides at both the 5' and 3' ends containing 2' O-Methyl 3' phosphorothioate and HPLC-purified. The genomic sgRNA target sequence (with PAM in bold) was: CCR5: 5'-GCAGCATAGTGAGCCCAGAAGGG-3' (SEQ ID NO: 3). Cas9 protein was purchased from Integrated DNA Technologies. RNP was complexed by mixing Cas9 with sgRNA at a molar ratio of 1:2.5 at room temperature. $CD34^+$ HSPCs were electroporated 2 days after thawing and expansion by using the Lonza Nucleofector 4D (program DZ-100) in P3 primary cell solution as follows: $10\times10^6$ cells/ml, 300 μg/ml Cas9 protein complexed with 150 μg/ml of sgRNA, in 100 µl. Following electroporation, cells were rescued with media at 37° C. after which rAAV6 was added (MOI 15,000 of 15,000 titrated to maximize modification efficiency and cell recovery). A mock-electroporated control was included in most experiments where cells underwent electroporation without Cas9 RNP.

Quantification of Putative CCR5 gRNA Off-Target Activity

Potential off-target sites in the human genome (hg19) were identified and ranked using the recently developed bioinformatics program COSMID (36), allowing up to three base mismatches without insertions or deletions and two base mismatches with either an inserted or deleted base (bulge). The top ranked sites were further investigated. Off-target activity at a total of 67 predicted loci was measured by deep sequencing in two biological replicates of CB-derived HSPCs. Bioinformatically predicted off-target loci were amplified by two rounds of PCR to introduce adaptor and index sequences for the Illumina MiSeq platform. All amplicons were normalized, pooled and quantified using the PerfeCTa NGS quantification kit per manufacturer's instructions (Quantabio, Beverly, MA, USA). Samples were sequenced on an Illumina MiSeq instrument using 2×250 bp paired end reads. INDELs were quantified as previously described66. Briefly, paired-end reads from MiSeq were filtered by an average Phred quality (Qscore) greater than 20 and merged into a longer single read from each pair with a minimum overlap of 30 nucleotides using Fast Length Adjustment of SHort reads. Alignments to reference sequences were performed using Burrows-Wheeler Aligner for each barcode and the percentages of insertions and deletions containing reads within a ±5-bp window of the predicted cut sites were quantified.

Measuring Insertions at the CCR5 Locus with ddPCR

Genomic DNA was extracted from either bulk or sorted populations using QuickExtract DNA Extraction Solution. For droplet-digital PCR (ddPCR), droplets were generated on a QX200 Droplet Generator (Bio-Rad) per manufacturer's protocol. A HEX reference assay detecting copy number input of the CCRL2 gene was used to quantify the chromosome 3 input. The assay designed to detect insertions at CCR5 consisted of: F:5'-GGG AGG ATT GGG AAG ACA-3' (SEQ ID NO: 13), R:5'-AGG TGT TCA GGA GAA GGA CA-3' (SEQ ID NO: 14), and labeled probe: 5'-FAM/AGC AGG CAT/ZEN/GCT GGG GAT GCG GTG G/3IABkFQ-3' (SEQ ID NO: 15). The reference assay designed to detect the CCRL2 genomic sequence: F:5'-CCT CCT GGC TGA GAA AAA G-3' (SEQ ID NO: 16), R:5'-GCT GTA TGA ATC CAG GTC C-3' (SEQ ID NO: 17), and labeled probe: 5'-HEX/TGT TTC CTC/ZEN/CAG GAT AAG GCA GCT GT/3IABkFQ-3' (SEQ ID NO: 18). The accuracy of this assay was established with genomic DNA from a monoallelic colony (50% allele fraction) as template. Final concentration of primer and probes was 900 nM and 250 nM respectively. Twenty microliters of the PCR reaction was used for droplet generation, and 40 µL of the droplets was used in the following PCR conditions: 95°-10 min, 45 cycles of 94°-30 s, 57° C.-30 s, and 72°-2 min, finalize with 98°-10 min and 4° C. until droplet analysis. Droplets were analyzed on a QX200 Droplet Reader (Bio-Rad) detecting FAM and HEX positive droplets. Control samples with non-template control, genomic DNA, and mock-treated samples, and 50% modification control were included. Data was analyzed using QuantaSoft (Bio-Rad).

HSPC Selection and Culturing

Human CD34$^+$ HSPCs mobilized peripheral blood purchased from AllCells (Alameda, CA, USA) and thawed per manufacturer's instructions. CD34$^+$ HSPCs were purified from umbilical cord blood collected donated under informed consent via the Binns Program for Cord Blood Research at Stanford University and used without freezing. In brief, mononuclear cells were isolated by density gradient centrifugation using Ficoll Paque Plus. Following two platelet washes, HSPCs were labeled and positively selected using the CD34$^+$ Microbead Kit Ultrapure (Miltenyi Biotec, San Diego, CA, USA) per manufacturer's protocol. Enriched cells were stained with APC anti-human CD34 (Clone 561; Biolegend, San Jose, CA, USA) and sample purity was assessed on an Accuri C6 flow cytometer (BD Biosciences, San Jose, CA, USA). Cells were cultured at 37° C., 5% CO2, and 5% O2 for 48 hours prior to gene editing. Culture media consisted of StemSpan SFEM II (Stemcell Technologies, Vancouver, Canada) supplemented with SCF (100 ng/ml), TPO (100 ng/ml), Flt3-Ligand (100 ng/ml), IL-6 (100 ng/ml), UM171 (35 nM), and StemRegenin1 (0.75 µM).

Colony Forming Unit Assay and Clonal Genotyping

Cells were single-cell sorted into 96-well plates (Corning) pre-filled with 100 µl of methylcellulose (Methocult, StemCell Technologies).

Single YFP+, YFP−, and mock-treated cells were sorted into methylcellulose media containing SCF, IL3, erythropoietin, and GM-CSF, conditions that support the growth of blood progenitor cells: erythroid progenitors (burst forming unit-erythroid or BFU-E, and colony-forming unit-erythroid or CFU-E), granulocyte-macrophage progenitors (CFU-GM), and multi-potential granulocyte, erythroid, macrophage, megakaryocyte progenitor cells (CFU-GEMM).

After 14 days, colonies were counted and scored as BFU-E, CFU-M, CFU-GM, and CFU-GEMM per the manual for 'Human Colony-forming Unit (CFU) Assays Using MethoCult' from StemCell Technologies. For DNA extraction from 96-well plates, PBS was added to wells with colonies, and the contents were mixed and transferred to a U-bottomed 96-well plate. Cells were pelleted by centrifugation at 300×g for 5 min followed by a wash with PBS. Finally, cells were resuspended in 25 µl QuickExtract DNA Extraction Solution (Epicentre, Madison, WI, USA) and transferred to PCR plates, which were incubated at 65° C. for 10 min followed by 100° C. for 2 min. For CCR5, a 3-primer PCR was set up with a forward primer outside the left homology arm (5'-CACCATGCTTGACCCAGTTT-3' (SEQ ID NO: 19)), a forward primer binding the polyadenylation signal in all inserts (5'-CGCATTGTCT-GAGTAGGTGT-3' (SEQ ID NO: 20)), and a reverse primer binding inside the right homology arm (5'-AGGTGTTCAG-GAGAAGGACA-3' (SEQ ID NO: 14)). Accupower premix was used for PCR reaction and cycled at the parameters: 950-5 min, and 35 cycles of 95°-20 s, 72° C.-60 s. DNA fragments were detected by agarose gel electrophoresis.

Macrophage Differentiation and Flow Cytometry

CD34$^+$ HSPCs were seeded at a density of $2\times10^5$ cells/mL in untreated 6-well polystyrene plates in differentiation medium (SFEM II supplemented with SCF (200 ng/ml), Il-3 (10 ng/mL), IL-6 (10 ng/mL), FLT3-L (50 ng/mL), M-CSF (10 ng/ml), GM-CSF all the behavioral tests. For spontaneous locomotor activity, assessment took place using the open field test in a square arena (76×76 cm2) with opaque white walls, surrounded with privacy blinds to eliminate external room cues. Mice were placed in the center of the open-field arena and allowed to freely move for 10 min while being tracked by Ethovision (Noldus Information Technology, Wageningen, the Netherlands) automated tracking system. Before each trial, the surface of the arena was cleaned with Virkon disinfectant. For analysis, the arena was divided into a central (53.5×53.5 cm2) and a peripheral zone (11.25-cm wide).

Passive Inhibitory Avoidance

The passive inhibitory avoidance test was used to assess fear-based learning and memory. We used a dual-compartment system (GEMINI system, San Diego Instruments), where lighted and dark compartments, equipped with grid floor that can deliver electrical shocks, are separated by an automated gate. On day one, each mouse was habituated to the apparatus by placing it into the lighted compartment. After 30 s, the gate opened allowing access to the dark compartment. When the mice entered the dark compartment, the gate closed and the time to cross after the gate opened is recorded (latency time). On day 2 or training day, the mice receive a 0.5 mA shock for 2 s after a 3 s delay after crossing from the lighted to the dark compartment. On day 3, or testing day, after being placed in the lighted compartment for 5 s, the gate opened allowing access to the dark compartment. The latency to enter the dark compartment was recorded. Maximum time to cross was 10 minutes.

Marble Burying

Repetitive behavior was tested in the marble bury test. Individual mice were introduced into cages containing 20 black glass marbles (1.5 cm diameter, four equidistant rows of five marbles each) on top of bedding 5 cm deep. After 30 min under low-light conditions, mice were removed and the number of marbles that were at least half-covered was determined.

NSG-IDUAX/X Mice

We used CRISPR-Cas9 to knock-in the W401X mutation (UniProtKB—Q8BMG0), analogous to the W402X mutation commonly found in patients with severe MPSI, into NSG mouse embryos. The guide RNA target sequence was searched using crispr.mit.edu and six shortlisted guides close to the target site were first screened by using an in vivo assay in NIH 3T3 cells. Two guides, one each on both sides of the target site, were selected: Guide1 (5'-TTATAGATGGAGAACAACTC-3' (SEQ ID NO: 21)) cleaves 4 bases upstream and Guide3 (5'-GTTGGACAGCAATCATACAG-3' (SEQ ID NO: 22)) cleaves 44 bases downstream of the target site. The guides were prepared by in vitro transcription (HiScribe™ T7 High Yield RNA Synthesis Kit, E2040S, New England Biolabs) of a dsDNA template generated by annealing two oligos (with a T7 promoter in the sense oligo) followed by a standard PCR reaction. The ssODN donor DNA contained an intended point mutation leading to a STOP codon (TGG to TAG): 5'-ggtgggagctagatattagggtaggaagccagatgctaggtatgagagagccaacagcctcagccctctgcttggcttatagATG GAGAACAA/CTCTAGGCAGAGGTCTCAAAGGCTGGGGCTGTGTTGGACAGCAATC ATA/CAGTGGGTGTCCTGGCCAGCACCCATCACCCTGAAGGCTCCGCAGCGGCCT GGAGTAC-3' (SEQ ID NO: 23) (lower case is intron, upper case is exon, guide cut sites marked by "/" and the mutation in bold).

Mouse Zygotes were obtained by mating NSG stud males with super-ovulated NSG females. Female NSG mice 3-4 weeks of age (JAX Laboratories, stock number 005557) were super-ovulated by intraperitoneal injection with 2.5 IU pregnant mare serum gonadotropin (National Hormone & Peptide Program, NIDDK), followed 48 hours later by injection of 2.5 IU human chorionic gonadotropin (hCG, National Hormone & Peptide Program, NIDDK). The animals were sacrificed 14 h following hCG administration and fertilized eggs were collected. CRISPR Injection mixture was prepared by dilution of the components into injection buffer (5 mM Tris, 0.1 mM EDTA, pH 7.5) to obtain the following concentrations: 10 ng/μl Cas9 mRNA (Thermo Fisher Scientific, Carlsbad, CA), 10 ng/μl IDUA1F and IDUA3F guide RNA and 10 ng/μl ssODN Donor (Integrated DNA Technologies, Coraville, IA). Zygote injections and embryo transfers were performed using standard protocols (70). A total of 38 zygotes were injected, the surviving 27 zygotes were transferred, which yielded seven live offspring. Among these a male homozygous for the mutation was used to establish the NSG-IDUAX/X colony. Mice were genotyped by-PCR based amplification followed by Sanger sequencing using the following primers: GENO F: 5'-CATGGCCCTGTTGGGTGAGTAATGA-3' (SEQ ID NO: 24), and GENO R: 5'-TGTGGTACTCCAGGCCGCTG-3' (SEQ ID NO: 25).

Measurement of p53 Protein Stabilization by FACs

Human HPSCs were incubated in doxorubicin (Sigma) at 0.2 μg/ml for 6 h. After harvesting and washing with PBS, the cells were incubated with LIVE/DEAD fixable blue dead cell stain for 15 min (ThermoFisher, USA). The cells were fixed with 2% paraformaldehyde for 10 min at RT, and permeabilized with 0.1% Triton X-100 in PBS for 7. Visigalli, I. et al. Gene therapy augments the efficacy of hematopoietic cell transplantation and fully corrects mucopolysaccharidosis type I phenotype in the mouse model. Blood 116, 5130-5139 (2010).
8. Wang, D. et al. Reprogramming erythroid cells for lysosomal enzyme production leads to visceral and CNS cross-correction in mice with Hurler syndrome. Proc. Natl Acad. Sci. USA 106, 19958-19963 (2009).
9. Biffi, A. et al. Lentiviral hematopoietic stem cell gene therapy benefits metachromatic leukodystrophy. Science 341, 1233158 (2013).
10. Eichler, F. et al. Hematopoietic Stem-Cell Gene Therapy for Cerebral Adrenoleukodystrophy. N. Engl. J. Med. 377, 1630-1638 (2017).
11. Cartier, N. et al. Hematopoietic stem cell gene therapy with a lentiviral vector in X-linked adrenoleukodystrophy. Science 326, 818-823 (2009).
12. McCormack, M. P. & Rabbitts, T. H. Activation of the T-cell oncogene LMO2 after gene therapy for X-linked severe combined immunodeficiency. N. Engl. J. Med. 350, 913-922 (2004).
13. Ranzani, M. et al. Lentiviral vector-based insertional mutagenesis identifies genes associated with liver cancer. Nat. Methods 10, 155-161 (2013).
14. Pan, Y. W., Scarlett, J. M., Luoh, T. T. & Kurre, P. Prolonged adherence of human immunodeficiency virus-derived vector particles to hematopoietic target cells leads to secondary transduction in vitro and in vivo. J. Virol. 81, 639-649 (2007).
15. Persons, D. A., Hargrove, P. W., Allay, E. R., Hanawa, H. & Nienhuis, A. W. The degree of phenotypic correction of murine beta-thalassemia intermedia following lentiviral-mediated transfer of a human gamma-globin gene is influenced by chromosomal position effects and vector copy number. Blood 101, 2175-2183 (2003).
16. Bak, R. O., Gomez-Ospina, N. & Porteus, M. H. Gene editing on center stage. Trends Genet. 34, 11 (2018).
17. Schiroli, G. et al. Preclinical modeling highlights the therapeutic potential of hematopoietic stem cell gene editing for correction of SCID-X1. Sci. Transl. Med. 9, https://doi.org/10.1126/scitranslmed.aan0820 (2017).
30. Lombardo, A. et al. Site-specific integration and tailoring of cassette design for sustainable gene transfer. Nat. Methods 8, 861-869 (2011).

31. Tomatsu, S. et al. Assay for glycosaminoglycans by tandem mass spectrometry and its applications. J. Anal. Bioanal. Tech. 2014, 006 (2014).

32. Fujitsuka, H. et al. Biomarkers in patients with mucopolysaccharidosis type II and IV. Mol. Genet. Metab. Rep. 19, 100455 (2019).

33. Hu, Z., Van Rooijen, N. & Yang, Y. G. Macrophages prevent human red blood cell reconstitution in immunodeficient mice. Blood 118, 5938-5946 (2011).

34. Wilkinson, F. L. et al. Neuropathology in mouse models of mucopolysaccharidosis type I, IIIA and IIIB. PLoS ONE 7, e35787 (2012).

35. Streit, W. J. An improved staining method for rat microglial cells using the lectin from *Griffonia simplicifolia* (GSA I-B4). J. Histochem. Cytochem. 38, 1683-1686 (1990).

36. Cradick, T. J., Qiu, P., Lee, C. M., Fine, E. J. & Bao, G. COSMID: a web-based tool for identifying and validating CRISPR/C as off-target sites. Mol. Ther. Nucleic Acids 3, e214 (2014).

37. Vakulskas, C. A. et al. A high-fidelity Cas9 mutant delivered as a ribonucleoprotein complex enables efficient gene editing in human hematopoietic stem and progenitor cells. Nat. Med. 24, 1216-1224 (2018).

38. Ihry, R. J. et al. p53 inhibits CRISPR-Cas9 engineering in human pluripotent stem cells. Nat. Med. 24, 939-946 (2018).

39. Haapaniemi, E., Botla, S., Persson, J., Schmierer, B. & Taipale, J. CRISPR-Cas9 genome editing induces a p53-mediated DNA damage response. Nat. Med. 24, 927-930 (2018).

40. Aldenhoven, M. et al. Hematopoietic cell transplantation for mucopolysaccharidosis patients is safe and effective: results after implementation of international guidelines. Biol. Blood Marrow Transpl. 21, 1106-1109 (2015).

41. Sadelain, M., Papapetrou, E. P. & Bushman, F. D. Safe harbours for the integration of new DNA in the human genome. Nat. Rev. Cancer 12, 51-58 (2012).

42. Wang, D. et al. Engineering a lysosomal enzyme with a derivative of receptor-binding domain of apoE enables delivery across the blood-brain barrier. Proc. Natl Acad. Sci. USA 110, 2999-3004 (2013).

43. Heyer, W. D., Ehmsen, K. T. & Liu, J. Regulation of homologous recombination in eukaryotes. Annu. Rev. Genet. 44, 113-139 (2010).

44. Yang, D. et al. Enrichment of G2/M cell cycle phase in human pluripotent stem cells enhances HDR-mediated gene repair with customizable endonucleases. Sci. Rep. 6, 21264 (2016).

45. van Galen, P. et al. The unfolded protein response governs integrity of the haematopoietic stem-cell pool during stress. Nature 510, 268-272 (2014).

46. Wilkinson, A. C. et al. Long-term ex vivo haematopoietic-stem-cell expansion allows nonconditioned transplantation. Nature, doi.org/10.1038/s41586-019-1244-x (2019).

47. Fares, I. et al. Cord blood expansion. Pyrimidoindole derivatives are agonists of human hematopoietic stem cell self-renewal. Science 345, 1509-1512 (2014).

48. Robert, F., Barbeau, M., Ethier, S., Dostie, J. & Pelletier, J. Pharmacological inhibition of DNA-PK stimulates Cas9-mediated genome editing. Genome Med. 7, 93 (2015).

49. Maruyama, T. et al. Increasing the efficiency of precise genome editing with CRISPR-Cas9 by inhibition of non-homologous end joining. Nat. Biotechnol. 33, 538-542 (2015).

50. Chu, V. T. et al. Increasing the efficiency of homology-directed repair for CRISPR-Cas9-induced precise gene editing in mammalian cells. Nat. Biotechnol. 33, 543-548 (2015).

51. Yu, S., Song, Z., Luo, J., Dai, Y. & Li, N. Over-expression of RAD51 or RAD54 but not RAD51/4 enhances extra-chromosomal homologous recombination in the human sarcoma (HT-1080) cell line. J. Biotechnol. 154, 21-24 (2011).

52. Charpentier, M. et al. CtIP fusion to Cas9 enhances transgene integration by homology-dependent repair. Nat. Commun. 9, 1133 (2018).

53. Schiroli, G. et al. Precise Gene Editing Preserves Hematopoietic Stem Cell Function following Transient p53-Mediated DNA Damage Response. Cell Stem Cell 24, 551-565.e558 (2019). promoter was chosen to minimize potential complications of GCase overexpression in the stem cell compartment. The Citrine-containing vectors were designated SFFV-GCase-P2A-Citrine and CD68S-GCase-P2A-Citrine. A third AAV, CD68S-GCase, lacking the reporter protein, was developed as a more clinically relevant vector for in vivo studies (FIG. 9A).

The targeting efficiencies achievable for each vector were determined by the percent of Citrine-positive (Citrine+) cells and by the percent of CCR5 alleles with on-target cassette integrations using molecular analysis (giving the cell and allele targeting frequencies, respectively). In the presence of both AAV and RNP, the SFFV-driven cassette resulted in approximately 51.5±9.1% (mean±SD) Citrine+ HSPCs 48-hours post-targeting, while AAV alone produced 5.9±4.2% dim Citrine+ cells, likely reflecting episomal expression (FIGS. 9C, 9D). The fraction of CCR5 alleles with on-target cassette integration in the unselected population was 29±9% as measured by droplet digital PCR (ddPCR) (FIG. 9E). To verify targeting in Citrine+ cells, these cells were sorted by FACS and the fraction of modified alleles measured (FIG. 9E). The allelic modification frequency of HSPCs treated with the SFFV-GCase-P2A-Citrine vector that were Citrine+ (SFFV-GCase-Citrine+) was 65.9±4.9%, corresponding to 69% and 31% mono-allelically and bi-allelically targeted cells, respectively. Genotyping of single cell-derived colonies corroborated that 98% percent of the Citrine+ HSPCs were targeted and, consistent with the ddPCR data, showed 67% monoallelic and 33% bi-allelic targeting.

Figures 9A, 9B, 9C, 9D, 9E:
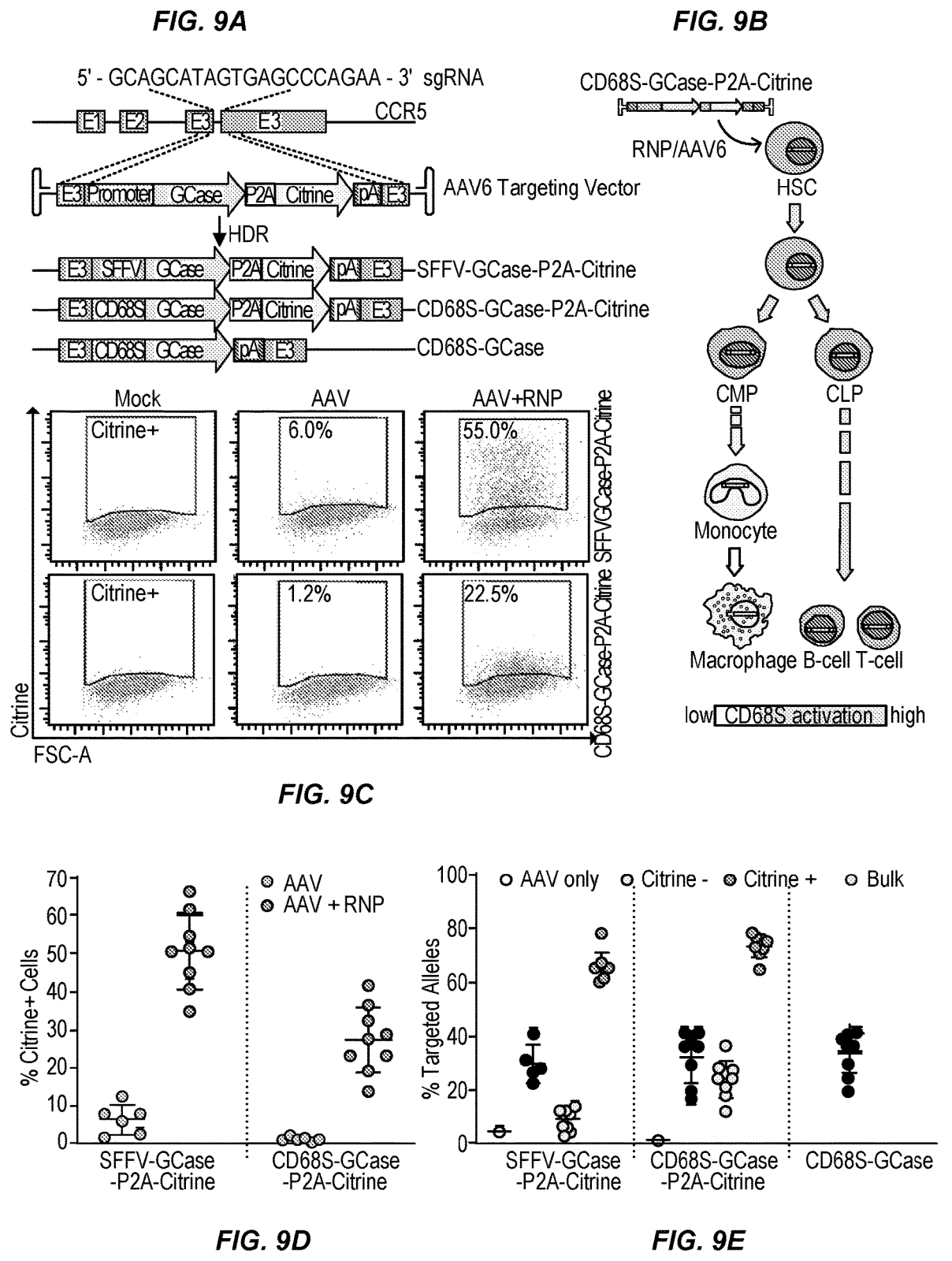

We predicted that because the CD68S promoter should be lineage-specific, Citrine would not be highly expressed in stem and non-myeloid biased progenitor cells and therefore, Citrine expression in HSPCs would not reflect the true editing efficiency of the CD68S-P2A-GCase-Citrine vector (FIG. 9B). Consistent with this, we found that at 48-hours post-modification, Citrine expression from HSPCs treated with the CD68S-GCase-P2A-Citrine AAV and RNP was dim (mean fluorescence intensity (MFI) was 24-fold lower than for the SFFV-GCase-Citrine+ cells) and the mean percentage of CD68S-GCase-Citrine+ HSPCs was 27.7±8.5%, significantly lower than for the SSFV-driven construct despite having comparable CCR5 allele targeting frequencies (32.3±9.6%) (FIGS. 9C-9E). Most importantly, the allele targeting frequency within the CD68S-GCase-Citrine negative population (CD68S-GCase-Citrine-) ranged from 11.8 to 36.4%, confirming the presence of targeted cells lacking Citrine expression (FIG. 9E). We reasoned that the subset of CD68S-GCase-Citrine+ HSPCs likely comprise a subpopulation of granulocyte-monocyte-committed progenitors with increased CD68S promoter activation, while CD68S-GCase-Citrine− HSPCs contain the more primitive $2.5\times10^5$ to $2\times10^6$ HSPCs and were dependent on the $CD34^+$ cell yield per human donor. We focused our long-term engraftment experiments on the CD68S-GCase-P2A-Citrine and CD68S-GCase vectors because of the potential detrimental effect of the SFFV promoter, its observed drop in expression, and its barriers to clinical translation. Targeted cells were transplanted without selection intrafemorally or intrahepaticaly into sublethally irradiated NSG mice. Primary human engraftment was quantified after sixteen weeks as the percentage of cells expressing human CD45 within the total hematopoietic population (mouse $CD45^+$ and human $CD45^+$).

Figures 12A, 12B, 12C, 12D, 12E, 12F, 12G:
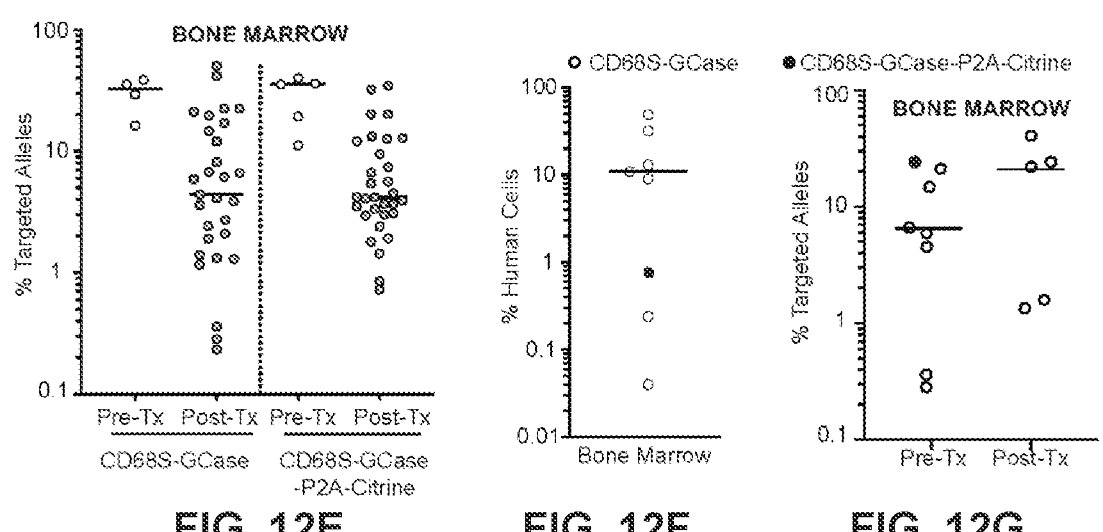
FIGS. 12A-12G. GCase-targeted HSPCs sustain long-term hematopoiesis.

Transplantation of GCase-targeted HSPCs resulted in substantial human cell chimerism. In the bone marrow, the median human cell chimerism was 23.2% (min: 0.17%; max: 91.5%) and 50.6% (0.53%; 91.7%) in CD68S-GCase-targeted and CD68S-GCase-P2A-Citrine-targeted cells, respectively (FIG. 12C). Similar engraftment numbers were seen in the spleen: 20.4% (0.14%; 79.3%) for the cassette lacking Citrine and 35.8% (0.38%; 89.6%) for the cassette containing Citrine (FIG. 12D). To determine the proportion of engrafted cells derived from targeted HSPCs, the targeted allele frequency of the engrafted $hCD45^+$ population in the bone marrow was measured using ddPCR in cell preparations that included mouse and human $CD45^+$ cells as the ddPCR assay recognizes only human alleles (FIG. 12E). The median allele targeting frequencies of the engrafted cell populations were 4.4% (min: 0.23%; max: 51.0%) and 4.2% (0.73%; 34.6%) for the CD68S-GCase and CD68S-GCase-P2A-Citrine cassettes, respectively; however, allele targeting frequency varied highly across human cell donors and mice. The allele targeting frequency of the engrafted cells tended to be lower compared to the transplanted HSPCs, with an observed drop ranging from 1.9 to 12.5-fold. Because cell doses of transplantation varied in the mice targeted with the Citrine-containing construct, the mice were colored-coded and tracked for engraftment and targeting efficiency in engrafted cells. This suggested a correlation between higher cell dose and higher engraftment of modified cells, a finding that is not surprising as there are likely more targeted long-term stem cells available for engraftment.

Serial engraftment studies are the gold standard to determine self-renewal capacity of hematopoietic stem cells. Secondary transplants were performed by isolating human $CD34^+$ cells from bone marrow in eight 16-week mice (7 from CD68S-GCase and one from CD68S-GCase-P2A-Citrine targeted cells) and transplanting them (without pooling) into eight NSG recipient mice. Human engraftment and allele targeting frequency were assessed 16 weeks later (32 weeks post-modification) as previously described. The median human cell chimerism of the capacity to produce human macrophages with heterologous GCase expression. Towards this end, human $CD14^+$ monocytes were isolated via FACS from the bone marrow of transplanted mice 16 weeks post-transplantation and differentiated by adding human macrophage colony stimulating factor (M-CSF). This step was performed in vitro because mouse M-CSF, a cytokine required for macrophage differentiation, does not have activity on human cells (44b). Human macrophages differentiated in this manner showed expression of the lineage marker CD68 as well as Citrine (12.3±4.5% of human CD68+ cells), verifying that engrafted, targeted HSPCs can produce macrophages that express the therapeutic GCase cassette (FIG. 13E).

Figures 14A, 14B, 14C:
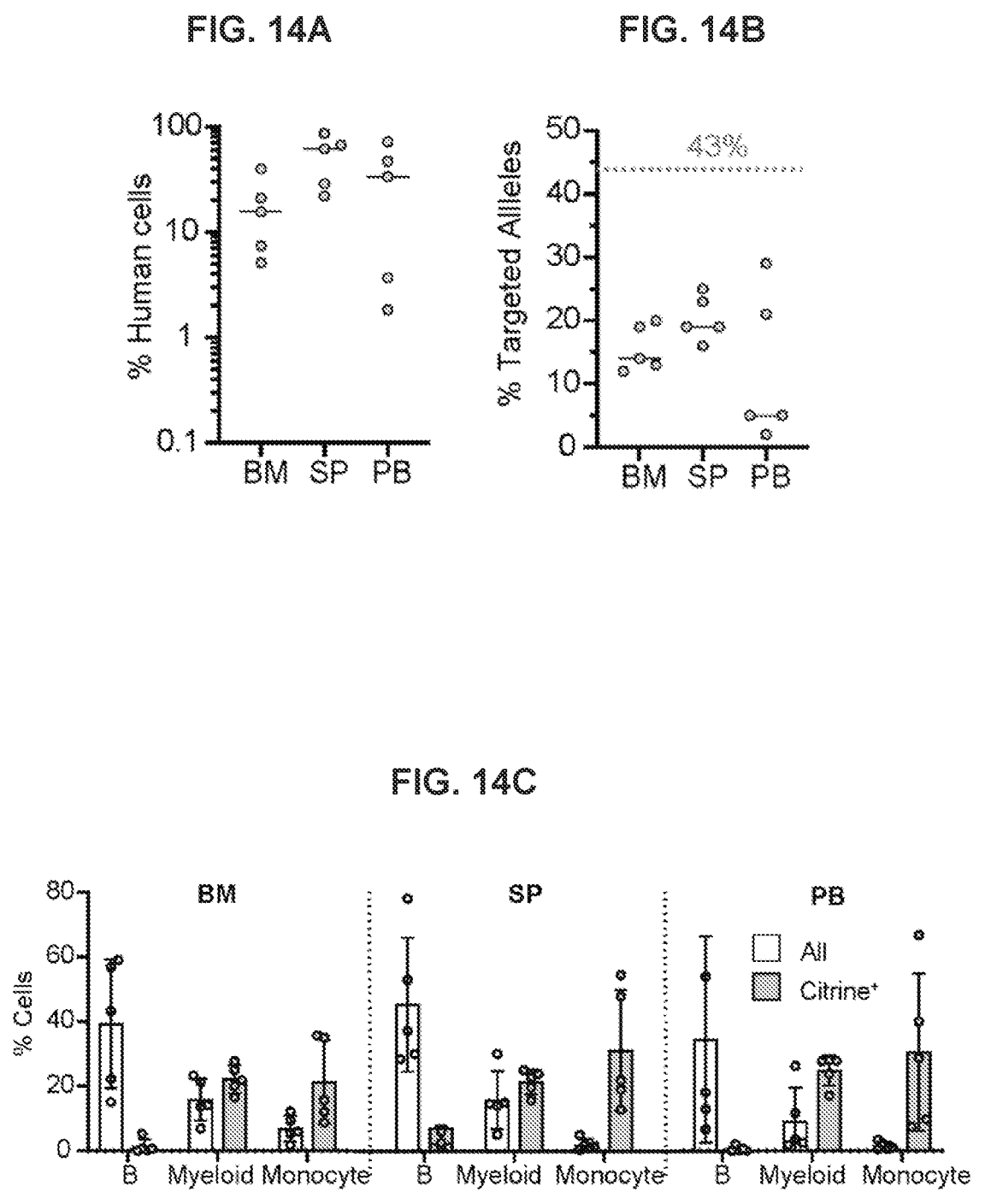
Figures 14, 14D, 14E, 14F:
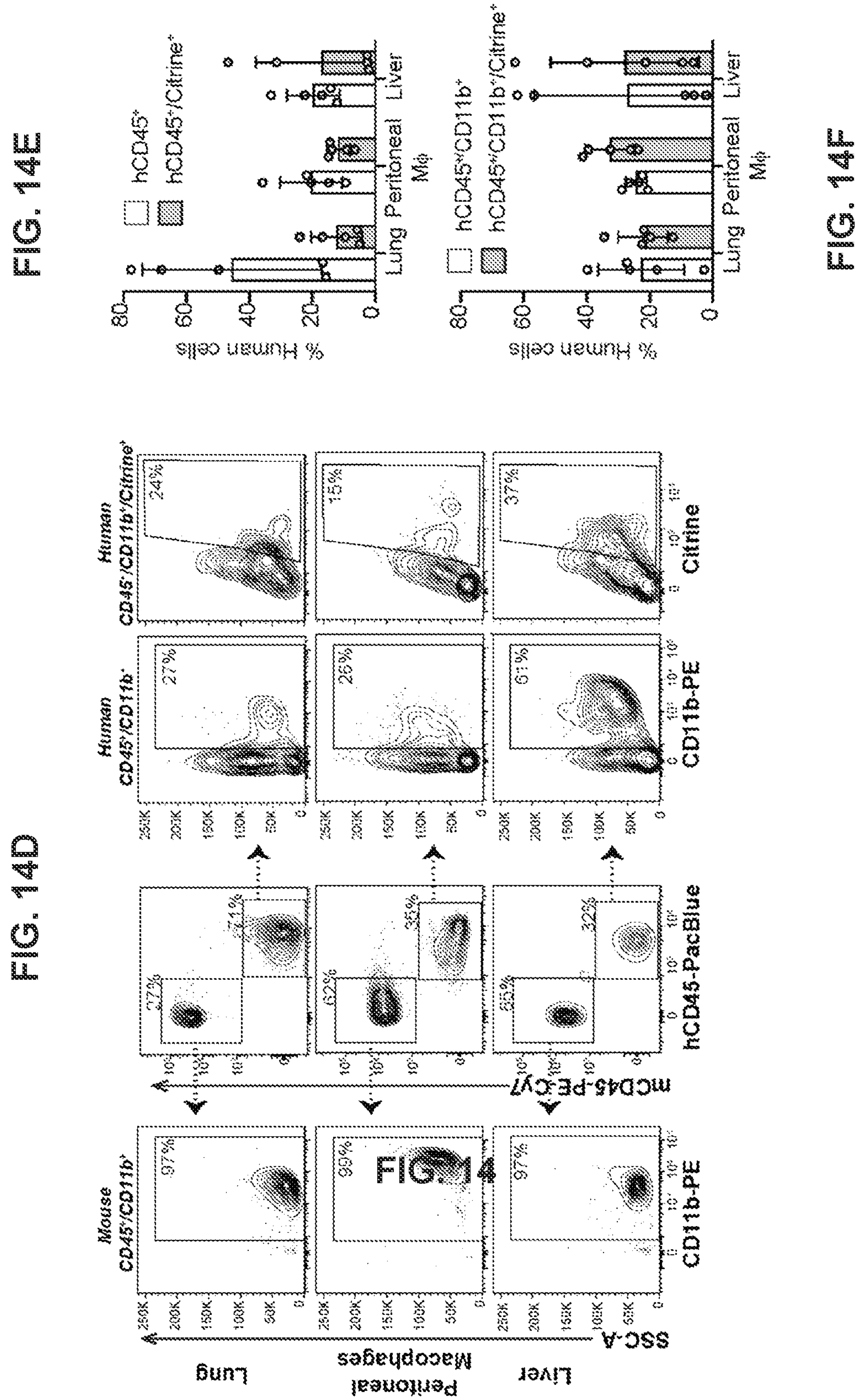
Figure 14H:
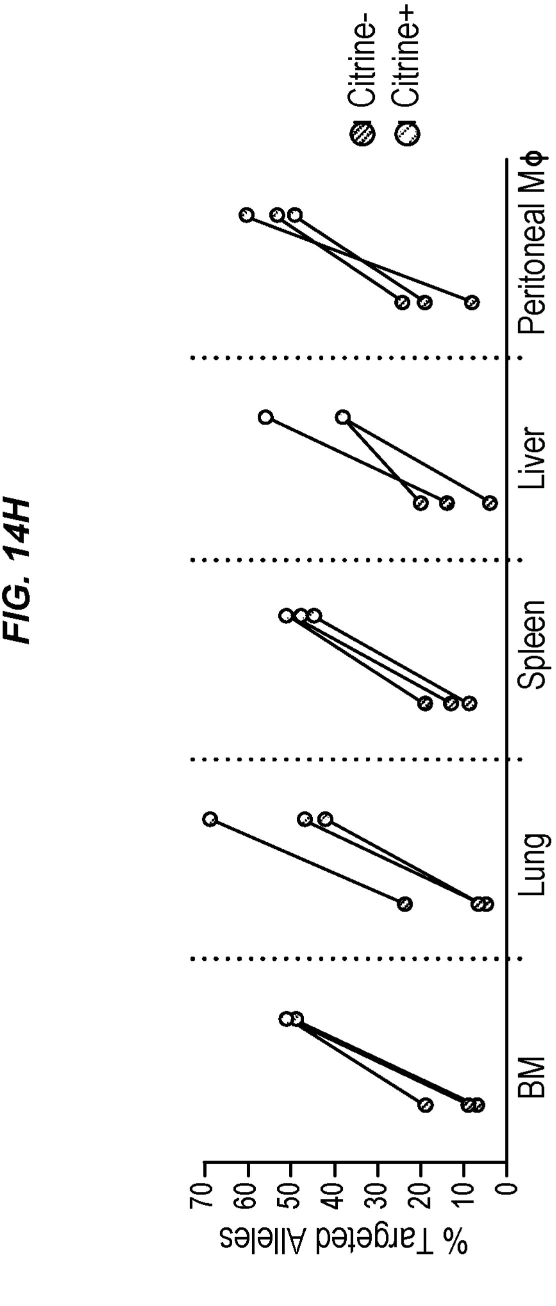
Figure 14G:
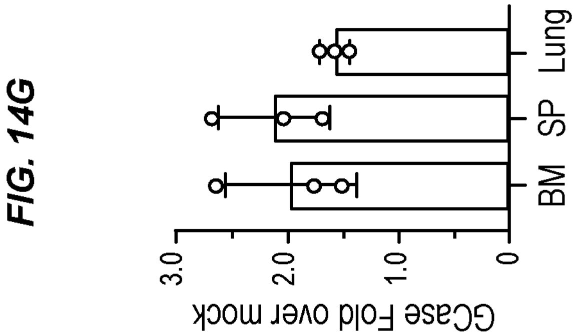

To improve engraftment and differentiation of myeloid lineages of our modified HSPCs in vivo, we performed transplantation experiments in NSG-SGM3 mice. These are NSG mice expressing human interleukin-3 (IL-3), human granulocyte/macrophage-stimulating factor (GM-CSF), and human Stem Cell Factor (SCF or KIT-ligand), cytokines that support the engraftment and differentiation of human myeloid lineages (45,46). At 16-weeks, transplantation of CD68S-GCase-P2A-Citrine-targeted cells resulted in median human cell chimerism of 17.7% (min: 5.1%; max: 39.6%), 61.7% (min: 22.1%; max: 85.8%), and 33.6% (min: 1.8%; max: 72%) in the bone marrow, spleen, and peripheral blood respectively (FIG. 14A). The median allele targeting frequencies of the engrafted cell populations were 15.6% (min: 12%; max: 20%), 20.4% (min: 16%; max: 25%), 5.0% (min: 2%; max: 29%) in the same tissues (FIG. 14B). The observed drop in modified engrafted cells relative to the pre-transplant level (43%) was 2.7-fold in the bone marrow, consistent with but in the low range of studies in NSG mice (FIG. 12E). We observed B, myeloid, and monocyte development with less preponderance of B-lymphoid population compared to NSG mice. As before, Citrine+ cells were seen exclusively in the myeloid and monocyte cells (FIG. 14C). Tissue macrophages were extracted from liver and lung using an enzymatic method and peritoneal macrophages were obtained by analysis of peritoneal fluid. We found robust human cell populations that were $CD45^+$ or CD45/CD11b+ as well as Citrine+ in these macrophage cell preparations (FIGS. 14D-14F). Samples with high cell numbers that allowed enrichment of live human-myeloid-Citrine+ for enzymatic analysis were sorted and the GCase activity measured. Consistent with our studies of HSPCs differentiated in culture, the Citrine+ cells expressed 2.0 (bone marrow), 2.1 (spleen), and 1.6-fold (lungs) higher GCase than Citrine− cells (FIGS. 11E and 14G). Analysis of targeted CCR5 alleles from sorted cells populations including bone marrow, lung, spleen, liver, and peritoneal macrophages show enrichment of targeted alleles and consistent transgene expression. In addition to the hematopoietic system, the liver has also been considered as potential enzyme replacement depot and in vivo liver-directed approaches using zinc finger nucleases have also been investigated in mouse models (70b). However, it is not clear the liver-secreted GCase would have the proper glycosylation to cross-correct affected cells or that it could cross into the CNS. Transplantation of ex vivo genome-edited HSPCs can provide direct replacement of pathological cells and leverages the ability of graft-derived macrophages that can migrate to the brain (19b) and bone. Therefore, autologous transplantation of gene-corrected cells, if coupled with safer conditioning regimens, could be a promising therapy for GD patients regardless of disease subtype.

To begin the development of autologous transplantation of genome-edited hematopoietic stem cells, we established an efficient application of CRISPR/Cas9 to target a functional copy of GCase into human $CD34^+$ HSPCs. Here, we use sgRNA/Cas9 and AAV6-mediated template delivery to target GCase to the CCR5 locus, a gene previously used for the insertion and expression of therapeutic genes (33b,34b). CCR5 is considered a safe harbor because germline deletions in this gene are common (up to 10% in the Northern European population) and have no overt developmental phenotype (35b). Germline CCR5 loss might be beneficial as it provides protection against HIV36, and possibly smallpox (71b), although it also appears to reduce protection against influenza (72b) and West Nile virus (73b). Compared to genetic correction of the affected locus, the use of a safe harbor constitutes a universal therapy for all patient mutations and has greater designability as regulatory and GCase protein sequences can be engineered with enhanced therapeutic properties. For targeting Gaucher disease specifically, it circumvents the design of genetic tools for the GBA locus, which can be non-specific given the presence of GBAP, a pseudogene with 96% sequence homology to the GBA gene (74b).

To express GCase from the CCR5 locus, we used a previously characterized derivative of the CD68 promoter and confirmed through in vitro and in vivo differentiation protocols that it achieves monocyte/macrophage specific expression of GCase (38b-40b). We reasoned that because the primary manifestations of Gaucher disease are due to pathology in monocyte/macrophage lineage cells, enzyme reconstitution in this lineage should be sufficient to provide phenotypic correction in this disease. Furthermore, our studies with the SFFV promoter did not consistently result in sustained GCase and reporter expression in human HSPCs, suggesting that high and sustained GCase in the stem and progenitor compartment might have detrimental effects. This would not be surprising, as negative impact in long-term therapeutic potential, provided the therapeutic cassettes are within the packaging capacity of AAV. These studies exemplify a specific use for this approach for the expression of human glucocerebrosidase as a potential intervention for the definitive treatment of GD and support further preclinical development of this strategy.

Methods

AAV Vector Plasmid Construction

The CCR5 donor vectors have been constructed by PCR amplification of ~500 bp left and right homology arms for the CCR5 locus from human genomic DNA. SFFV and GBA sequences were amplified from plasmids. The CD68S sequence was obtained from Dahl et al, 201581 and was cloned from a gblock Gene Fragment (IDT, San Jose, CA, USA). Primers were designed using an online assembly tool (NEBuilder, New England Biolabs, Ipswich, MA, USA) and were ordered from Integrated DNA Technologies (IDT, San Jose, CA, USA). Fragments were Gibson-assembled into a the pAAV-MCS plasmid (Agilent Technologies, Santa Clara, CA, USA).

rAAV Production rAAV was produced using a dual-plasmid system as previously described82. Briefly, HEK293 cells were transfected with plasmids encoding an AAV vector and AAV rep and cap genes. HEK293 cells were harvested 48-hours post-transfection and lysed using three cycles of freeze-thaw. Cellular debris was pelleted by centrifugation at 1350 g for 20 minutes and the supernatant collected. Active rAAV particles were purified using iodixanol density gradient ultracentrifugation, dialyzed in PBS, and stored in PBS at −80° C. rAAV vectors for in vivo applications was ordered from Vigene Biosciences (Rockville, MD, USA). Viral titers were determined using droplet digital PCR with the following primer/probe combination: F: GGA ACC CCT AGT GAT GGA GTT (SEQ ID NO: 26), R: CGG CCT CAG TGA GCG A (SEQ ID NO: 27), P: /56FAM/CAC TCC CTC/ZEN/TCT GCG CGC TCG/3IABkFQ/(SEQ ID NO: 28).

HSPC Isolation and Culturing

Human CD34$^+$ HSPCs mobilized from peripheral blood were purchased frozen from AllCells (Alameda, CA, USA) and thawed per manufacturer's instructions. Cord-blood derived human CD34$^+$ HSPCs were obtained through the Binns Program for Cord Blood Research at Stanford University. Briefly, mononuclear cells were isolated by density gradient centrifugation using Ficoll Plaque Plus density gradient medium followed by two platelets washes. CD34$^+$ mononuclear cells were positively selected using CD34$^+$ Microbead Kit Ultrapure (Miltenyi Biotec, San Diego, CA, USA) per manufacturer's instructions. Purity of the isolation was assessed by staining cells with APC-conjugated anti-human CD34$^+$ (Clone 561; Biolegend, San Jose, CA, USA) and analyzing the fraction of APC$^+$ cells using an Accuri C6 flow cytometer (BD Biosciences, San Jose, CA, USA). Cells were cultured in media consisting of StemSpan SFEM II (Stemcell Technologies, Vancouver, Canada) supplemented with SCF (100 ng/ml), TPO (100 ng/ml), Flt3-Ligand (100 ng/ml), IL-6 (100 ng/ml), UM171 (35 nM), and StemRegenin1 (0.75 mM).

Gene Editing in HSPCs

An sgRNA targeting CCR5 exon 3 (sequence; 5'-GCAGCATAGTGAGCCCAGAA-3' (SEQ ID NO: 4)) was purchased from TriLink Biotechnologies (San Diego, CA, USA) with the chemical modification 2'-O-methyl-3'-phosphorothioate (31b). Cas9 and Hifi Cas9 were purchased from Integrated DNA Technologies (IDT, San Jose, CA, USA Catalog #1081058 and #1081060). The editing procedure was performed as follows: sgRNA and Cas9 protein were complexed at a molar ration of 1:2.5 (sgRNA:Cas9) at room temperature for 5 minutes. The RNP was electroporated into human CD34$^+$ HSPCs 48 hours after thawing using the Lonza 4D nucleofector with the following conditions: pulse code: DZ100; cell density: $1\times10^6$ cells in 100 μl; [Cas9]: 30 μg; [sgRNA]: 15 ug. Following electroporation, cells were immediately rescued with HSPC culture media pre-warmed to 37° C. rAAV6 was applied to cells at an MOI of 10,000-20,000.

Measurement of Cassette Integration using ddPCR

Genomic DNA was extracted from selected or unselected cell populations using QuickExtract DNA Extract Solution and digested using AFIII (New England Biosciences). Two detection probes were used in the assay to simultaneously quantify wildtype CCLR2 reference alleles gene-targeted CCR5 alleles. The ratio of detected CCLR2/CCR5 events gave the fraction of targeted alleles in the original cell population. The CCR5 detection assay was designed as follows: F:5'-GGG AGG ATT GGG AAG ACA-3' (SEQ ID NO: 13), R: 5'-AGG TGT TCA GGA GAA GGA CA-3' (SEQ ID NO: 14), labeled probe: 5'-FAM/AGC AGG CAT/ZEN/GCT GGG GAT GCG GTG G/3IABkFQ-3' (SEQ ID NO: 15). The reference assay was designed as follows: F:5'-CCT CCT GGC TGA GAA AAA G-3' (SEQ ID NO: 16), R: 5'-GCT GTA TGA ACT CAG GTC C/3IABkFQ-3' (SEQ ID NO: 29). Primer and probes final concentrations were 900 nM and 250 nM, respectively. 20 μL of the PCR reaction was used for droplet generation. 40 μL of droplets was used in a PCR reaction with the conditions: 95° C. for 10 min, 45 cycles of melting at 94° C. for 30 s, annealing at 57° C. for 30 s, and extension at 72° C. for 2 min, with a final extension at 98° C. for 10 min. All steps were performed with ramping of 2C/s and reactions were stored at 4° C. covered from light until droplet analysis. Analysis was performed on a Qx200 Droplet Reader (Bio-Rad) detecting FAM and HEX positive droplets. Control samples included Mock (non-modified) genomic DNA and no-template control. Data analysis was performed using Quantasoft (Bio-Rad).

Colony-Forming Unit Assay and Clonal Genotyping

Colony-Forming Unit assays were performed using Methocult methylcellulose (StemCell Technologies) as per the manufacturer's protocol. Briefly, CD34$^+$ HSPCs were single-sorted into 96-well flat-bottom plates (Corning) pre-filled with 100 ul Methocult. Cells were cultured for fourteen days at 37° C., 5% $O_2$ and 5% $CO_2$. Colonies were quantified and characterized morphologically by color, size and shape as burst-forming unit-erythroid (E-BFU), colony-forming unit-erythroid (E-CFU), colony-forming unit-granulocyte/monocyte (CFU-GM) or colony-forming unit-granulocyte/erythroid/macrophage/megakaryocyte.

Colonies were genotyped by extracting genomic DNA in QuickExtract DNA Extraction Reagent (Lucigen, QE09050) and performing a 3-primer in-and-out PCR to amplify both wild-type CCR5 alleles and CCR5 alleles with targeted integrations. The 3-primer in-and-out PCR utilized a forward primer out the left CCR5 homology arm (5'-CACCATGCTTGACCCAGTTT-3' (SEQ ID NO: 19)), a forward primer binding the poly-adenylation signal in the cassette (5'-CGCATTGTCTGAGTAGGTGT-3' (SEQ ID NO: 20)), and a reverse primer binding inside the right homology arm (5'-AGGTGTTCAGGAGAAGGACA-3' (SEQ ID NO: 14)). Accupower pre-mix (Bioneer, Oakland, CA) was used for the PCR with cycling parameters: 95° C. for 5 min, and 35 cycles of 95° C. for 20 s, 72° C. for 60 seconds. DNA fragments were detected by agarose gel electrophoresis. Wild-type and targeted CCR5 alleles yielded bands of 590 base-pairs and 1100 base-pairs, respectively.

Macrophage Differentiation and Flow Cytometry

CD34+ HSPCs were seeded at a density of 2×105 cells/mL in non-treated 6-well plates in differentiation medium (SFEM II supplemented with SCF (200 ng/ml), Il-3 (10 ng/mL), IL-6 (10 ng/mL), FLT3-L (50 ng/mL), M-CSF (10 ng/ml) and penicillin/streptomycin 7b. Pandey, M. K. et al. Gaucher disease: chemotactic factors and immunological cell invasion in a mouse model. Molecular genetics and metabolism 111, 163-171, doi:10.1016/j.ymgme.2013.09.002 (2014).

8b. Deegan, P. et al. Treatment patterns from 647 patients with Gaucher disease: An analysis from the Gaucher Outcome Survey. Blood Cells Mol Dis 68, 218-225, doi:10.1016/j.bcmd.2016.10.014 (2018).

9b. Hughes, D. A. et al. Velaglucerase alfa (VPRIV) enzyme replacement therapy in patients with Gaucher disease: Long-term data from phase III clinical trials. American journal of hematology 90, 584-591, doi:10.1002/ajh.24012 (2015).

10b. Lukina, E. et al. Improvement in hematological, visceral, and skeletal manifestations of Gaucher disease type 1 with oral eliglustat tartrate (Genz-112638) treatment: 2-year results of a phase 2 study. Blood 116, 4095-4098, doi: 10.1182/blood-2010-06-293902 (2010).

11b. Pastores, G. M., Barnett, N. L. & Kolodny, E. H. An open-label, noncomparative study of miglustat in type I Gaucher disease: efficacy and tolerability over 24 months of treatment. Clin Ther 27, 1215-1227, doi:10.1016/j.clinthera.2005.08.004 (2005).

12b. Weinreb, N. J. et al. Long-term clinical outcomes in type 1 Gaucher disease following 10 years of imiglucerase treatment. J Inherit Metab Dis 36, 543-553, doi: 10.1007/s10545-012-9528-4 (2013).

13b. Zimran, A., Wajnrajch, M., Hernandez, B. & Pastores, G. M. Taliglucerase alfa: safety and efficacy across 6 clinical studies in adults and children with Gaucher disease. Orphanet journal of rare diseases 13, 36, doi: 10.1186/s13023-018-0776-8 (2018).

14b. Ito, S. & Barrett, A. J. Gauchers disease—a reappraisal of hematopoietic stem cell transplantation. Pediatric hematology and oncology 30, 61-70, doi:10.3109/08880018.2012.762076 (2013).

15b. Machaczka, M. Allogeneic hematopoietic stem cell transplantation for treatment of Gaucher disease. Pediatric hematology and oncology 30, 459-461, doi:10.3109/08880018.2013.793757 (2013).

16b. Somaraju, U. R. & Tadepalli, K. Hematopoietic stem cell transplantation for Gaucher disease. The Cochrane database of systematic reviews 10, Cd006974, doi: 10.1002/14651858.CD006974.pub4 (2017).

17b. Correll, P. H., Colilla, S., Dave, H. P. & Karlsson, S. High levels of human glucocerebrosidase activity in macrophages of long-term reconstituted mice after retroviral infection of hematopoietic stem cells. Blood 80, 331-336 (1992).

18b. Dunbar, C. E. et al. Retroviral transfer of the glucocerebrosidase gene into CD34+ cells from patients with Gaucher disease: in vivo detection of transduced cells without myeloablation. Human gene therapy 9, 2629-2640, doi:10.1089/hum.1998.9.17-2629 (1998).

19b. Krall, W. J., Challita, P. M., Perlmutter, L. S., Skelton, D. C. & Kohn, D. B. Cells expressing human glucocerebrosidase from a retroviral vector repopulate macrophages and central nervous system microglia after murine bone marrow transplantation. Blood 83, 2737-2748 (1994).

20b. Schiffmann, R. et al. Transfer of the human glucocerebrosidase gene into hematopoietic stem cells of nonablated recipients: successful engraftment and long-term expression of the transgene. Blood 86, 1218-1227 (1995).

21b. Kim, E. Y. et al. Long-term expression of the human glucocerebrosidase gene in vivo after transplantation of bone-marrow-derived cells transformed with a lentivirus vector. The journal of gene medicine 7, 878-887, doi: 10.1002/jgm.732 (2005).

22b. Enquist, I. B. et al. Effective cell and gene therapy in a murine model of Gaucher disease. Proceedings of the National Academy of Sciences of the United States of America 103, 13819-13824, doi:10.1073/pnas.0606016103 (2006).

23b. Dahl, M. et al. Lentiviral gene therapy using cellular promoters cures type 1 Gaucher disease in mice. Mol Ther 23, 835-844, doi:10.1038/mt.2015.16 (2015).

24b. McCormack, M. P. & Rabbitts, T. H. Activation of the T-cell oncogene LMO2 after gene therapy for X-linked severe combined immunodeficiency. N Engl J Med 350, 913-922, doi:10.1056/NEJMra032207 (2004).

25b. Ranzani, M. et al. Lentiviral vector-based insertional mutagenesis identifies genes associated with liver cancer. Nat Methods 10, 155-161, doi:10.1038/nmeth.2331 (2013). 26b. Porteus, M. H. A New Class of Medicines through DNA Editing. N Engl J Med 380, 947-959, doi:10.1056/NEJMra1800729 (2019).

27b. Bak, R. O., Dever, D. P. & Porteus, M. H. CRISPR/Cas9 genome editing in human hematopoietic stem cells. Nat Protoc 13, 358-376, doi:10.1038/nprot.2017.143 (2018).

```
sgRNA sequence
                                                              SEQ ID NO: 6
5'-2'OMe(G(ps)C(ps)A(ps)) GCA UAG UGA GCC CAG AAG UUU UAG AGC UAG

AAA UAG CAA GUU AAA AUA AGG CUA GUC CGU UAU CAA CUU GAA AAA

GUG GCA CCG AGU CGG UGC UU 2'OMe(U(ps)U(ps)U(ps)) U -3'
```

-continued (ps) indicates phosphorothioate
MPS1: Strategy is to knock in IDUA cDNA into Exon 3 of CCR5 safe harbor gene to overexpress IDUA enzyme and the selectable marker INGFR. Otherwise identical or substantially identical sequences in which the tNGFR marker (nucleotides 2961-3848) is replaced with another selectable can also be used.
Left homology arm: 1-500 bp
PGK promoter: 501-1001 bp
IDUA cDNA: 1002-2960 bp
T2A-tNGFR: 2961-3848 bp
BgH Poly A: 3849-4099 bp
Right homology arm: 4100-4599 bp

SEQ ID NO: 7

TTTCATGAATTCCCCCAACAGAGCCAAGCTCTCCATCTAGTGGACAGGGAAGCTA

GCAGCAAACCTTCCCTTCACTACAAAACTTCATTGCTTGGCCAAAAAGAGAGTTA

ATTCAATGTAGACATCTATGTAGGCAATTAAAAACCTATTGATGTATAAAACAGT

TTGCATTCATGGAGGGCAACTAAATACATTCTAGGACTTTATAAAAGATCACTTT

TTATTTATGCACAGGGTGGAACAAGATGGATTATCAAGTGTCAAGTCCAATCTAT

GACATCAATTATTATACATCGGAGCCCTGCCAAAAAATCAATGTGAAGCAAATC

GCAGCCCGCCTCCTGCCTCCGCTCTACTCACTGGTGTTCATCTTTGGTTTTGTGGG

CAACATGCTGGTCATCCTCATCCTGATAAACTGCAAAAGGCTGAAGAGCATGACT

GACATCTACCTGCTCAACCTGGCCATCTCTGACCTGTTTTTCCTTCTTACTGTCCC

CTTCTctagataccgggtaggggaggcgcttttcccaaggcagtctggagcatgcgctttagcagccccgctgggcacttggcgc tacacaagtggcctctggcctcgcacacattccacatccaccggtaggcgccaaccggctccgttctttggtggccccttcgcgccac cttctactcctcccctagtcaggaagttcccccccgccccgcagctcgcgtcgtgcaggacgtgacaaatggaagtagcacgtctcac tagtctcgtgcagatggacagcaccgctgagcaatggaagcgggtaggcctttggggcagcggccaatagcagctttgctccttcgct ttctgggctcagaggctgggaaggggggtccgggggggctcaggggcgggctcaggggggggggggcccgaaggt cctccggaggcccggcattctgcacgcttcaaaagcgcacgtctgccgcgctgttctcctcttcctcaggatccATGCGTCCC

CTGCGCCCCCGCGCCGCGCTGCTGGCGCTCCTGGCCTCGCTCCTGGCCGCGCCCC

CGGTGGCCCCGGCCGAGGCCCCGCACCTGGTGCATGTGGACGCGGCCCGCGCGC

TGTGGCCCCTGCGGCGCTTCTGGAGGAGCACAGGCTTCTGCCCCCCGCTGCCACA

CAGCCAGGCTGACCAGTACGTCCTCAGCTGGGACCAGCAGCTCAACCTCGCCTAT

GTGGGCGCCGTCCCTCACCGCGGCATCAAGCAGGTCCGGACCCACTGGCTGCTG

GAGCTTGTCACCACCAGGGGGTCCACTGGACGGGGCCTGAGCTACAACTTCACC

CACCTGGACGGGTACCTGGACCTTCTCAGGGAGAACCAGCTCCTCCCAGGGTTTG

AGCTGATGGGCAGCGCCTCGGGCCACTTCACTGACTTTGAGGACAAGCAGCAGG

TGTTTGAGTGGAAGGACTTGGTCTCCAGCCTGGCCAGGAGATACATCGGTAGGTA

CGGACTGGCGCATGTTTCCAAGTGGAACTTCGAGACGTGGAATGAGCCAGACCA

CCACGACTTTGACAACGTCTCCATGACCATGCAAGGCTTCCTGAACTACTACGAT

GCCTGCTCGGAGGGTCTGCGCGCCGCCAGCCCCGCCCTGCGGCTGGGAGGCCCC

GGCGACTCCTTCCACACCCCACCGCGATCCCCGCTGAGCTGGGGCCTCCTGCGCC

ACTGCCACGACGGTACCAACTTCTTCACTGGGGAGGCGGGCGTGCGGCTGGACT

ACATCTCCCTCCACAGGAAGGGTGCGCGCAGCTCCATCTCCATCCTGGAGCAGGA

GAAGGTCGTCGCGCAGCAGATCCGGCAGCTCTTCCCCAAGTTCGCGGACACCCCC

ATTTACAACGACGAGGCGGACCCGCTGGTGGGCTGGTCCCTGCCACAGCCGTGG

AGGGCGGACGTGACCTACGCGGCCATGGTGGTGAAGGTCATCGCGCAGCATCAG

AACCTGCTACTGGCCAACACCACCTCCGCCTTCCCCTACGCGCTCCTGAGCAACG

-continued

ACAATGCCTTCCTGAGCTACCACCCGCACCCCTTCGCGCAGCGCACGCTCACCGC

GCGCTTCCAGGTCAACAACACCCGCCCGCCGCACGTGCAGCTGTTGCGCAAGCC

GGTGCTCACGGCCATGGGGCTGCTGGCGCTGCTGGATGAGGAGCAGCTCTGGGC

CGAAGTGTCGCAGGCCGGGACCGTCCTGGACAGCAACCACACGGTGGGCGTCCT

GGCCAGCGCCCACCGCCCCCAGGGCCCGGCCGACGCCTGGCGCGCCGCGGTGCT

GATCTACGCGAGCGACGACACCCGCGCCCACCCCAACCGCAGCGTCGCGGTGAC

CCTGCGGCTGCGCGGGGTGCCCCCCGGCCCGGGCCTGGTCTACGTCACGCGCTAC

CTGGACAACGGGCTCTGCAGCCCCGACGGCGAGTGGCGGCGCCTGGGCCGGCCC

GTCTTCCCCACGGCAGAGCAGTTCCGGCGCATGCGCGCGGCTGAGGACCCGGTG

GCCGCGGCGCCCCGCCCCTTACCCGCCGGCGGCCGCCTGACCCTCAGACCTGCAC

TTAGATTGCCTTCCCTTTTGTTGGTCCACGTTTGCGCTAGGCCCGAGAAACCGCCA

GGACAAGTAACACGGCTTCGGGCGCTGCCACTTACTCAGGGGCAGCTGGTGCTG

GTTTGGTCAGACGAGCATGTCGGAAGCAAATGCCTTTGGACCTACGAGATACAA

TTTTCACAGGATGGTAAGGCTTACACTCCGGTCTCAAGAAAGCCCAGTACCTTTA

ACCTTTTTGTGTTCAGTCCAGATACTGGAGCAGTAAGCGGTTCATATAGAGTCAG

AGCGCTGGATTACTGGGCCAGGCCCGGACCTTTCTCAGATCCGGTCCCCTACCTG

GAAGTTCCCGTGCCGCGGGGTCCTCCATCACCAGGCAACCCAGGAAGCGGAGCT

ACTAACTTCAGCCTGCTGAAGCAGGCTGGAGACGTGGAGGAGAACCCTGGACCT

GGGGCAGGTGCCACCGGCCGCGCCATGGACGGGCCGCGCCTGCTGCTGTTGCTG

CTTCTGGGGGTGTCCCTTGGAGGTGCCAAGGAGGCATGCCCCACAGGCCTGTACA

CACACAGCGGTGAGTGCTGCAAAGCCTGCAACCTGGGCGAGGGTGTGGCCCAGC

CTTGTGGAGCCAACCAGACCGTGTGTGAGCCCTGCCTGGACAGCGTGACGTTCTC

CGACGTGGTGAGCGCGACCGAGCCGTGCAAGCCGTGCACCGAGTGCGTGGGGCT

CCAGAGCATGTCGGCGCCaTGCGTGGAGGCCGACGACGCCGTGTGCCGCTGCGCC

TACGGCTACTACCAGGATGAGACGACTGGGCGCTGCGAGGCGTGCCGCGTGTGC

GAGGCGGGCTCGGGCCTCGTGTTCTCCTGCCAGGACAAGCAGAACACCGTGTGC

GAGGAGTGCCCCGACGGCACGTATTCCGACGAGGCCAACCACGTGGACCCGTGC

CTGCCCTGCACCGTGTGCGAGGACACCGAGCGCCAGCTCCGCGAGTGCACACGC

TGGGCCGACGCCGAGTGCGAGGAGATCCCTGGCCGTTGGATTACACGGTCCACA

CCCCCAGAGGGCTCGGACAGCACAGCCCCCAGCACCCAGGAGCCTGAGGCACCT

CCAGAACAAGACCTCATAGCCAGCACGGTGGCGGGTGTGGTGACCACAGTGATG

GGCAGCTCCCAGCCCGTGGTGACCCGAGGCACCACCGACAACCTCATCCCTGTCT

ATTGCTCCATCCTGGCTGCTGTGGTTGTGGGTCTTGTGGCCTACATAGCCTTCAAG

AGGTAAtaacTCGAGCCGCTGAtcagcctcgactgtgccttctagttgccagccatctgttgtttgcccctcccccgtgc cttccttgaccctggaaggtgccactcccactgtcctttcctaataaaatgaggaaattgcatcgcattgtctgagtaggtgtcattctattct ggggggtggggtggggcaggacagcaagggggaggattgggaagacaatagcaggcatgctggggatgcggtgggctctatgg gggctcactatgctgccgcccagtgggactttggaaatacaatgtgtcaactcttgacagggctctattttataggcttcttctctggaatct tcttcatcatcctcctgacaatcgataggtacctggctgtcgtccatgctgtgtttgctttaaaagccaggacggtcacctttggggtggtg acaagtgtgatcacttgggtggtggctgtgtttgcgtctctcccaggaatcatctttaccagatctcaaaaagaaggtcttcattacacctg cagctctcattttccatacagtcagtatcaattctggaagaatttccagacattaaagatagtcatcttggggctggtcctgccgctgcttgt -continued

```
catggtcatctgctactcgggaatcctaaaaactctgcttcggtgtcgaaatgagaagaagaggcacagggctgtgaggcttatcttca

ccatcatgattgtttattttctcttctgggctccctacaa
```

MPS1: Strategy is to knock in IDUA cDNA into Exon 3 of CCR5 safe harbor gene to overexpress IDUA enzyme without a selectable marker
Left homology arm: 1-500 bp
PGK promoter: 507-995 bp
IDUA cDNA: 1002-2960 bp
BgH Poly A: 2987-3194 bp
Right homology arm: 3212-3711 bp

SEQ ID NO: 8

```
TTTCATGAATTCCCCCAACAGAGCCAAGCTCTCCATCTAGTGGACAGGGAAGCTA

GCAGCAAACCTTCCCTTCACTACAAAACTTCATTGCTTGGCCAAAAAGAGAGTTA

ATTCAATGTAGACATCTATGTAGGCAATTAAAAACCTATTGATGTATAAAACAGT

TTGCATTCATGGAGGGCAACTAAATACATTCTAGGACTTTATAAAAGATCACTTT

TTATTTATGCACAGGGTGGAACAAGATGGATTATCAAGTGTCAAGTCCAATCTAT

GACATCAATTATTATACATCGGAGCCCTGCCAAAAAATCAATGTGAAGCAAATC

GCAGCCCGCCTCCTGCCTCCGCTCTACTCACTGGTGTTCATCTTTGGTTTTGTGGG

CAACATGCTGGTCATCCTCATCCTGATAAACTGCAAAAGGCTGAAGAGCATGACT

GACATCTACCTGCTCAACCTGGCCATCTCTGACCTGTTTTTCCTTCTTACTGTCCC

CTTCTctagataccgggtaggggaggcgcttttcccaaggcagtctggagcatgcgctttagcagccccgctgggcacttggcgc

tacacaagtggcctctggcctcgcacacattccacatccaccggtaggcgccaaccggctccgttctttggtggccccttcgcgccac

cttctactcctcccctagtcaggaagttcccccccgccccgcagctcgcgtcgtgcaggacgtgacaaatggaagtagcacgtctcac

tagtctcgtgcagatggacagcaccgctgagcaatggaagcgggtaggcctttggggcagcggccaatagcagctttgctccttcgct

ttctgggctcagaggctgggaaggggtgggtccgggggcgggctcaggggcgggctcaggggcgggcgcccgaaggt

cctccggaggcccggcattctgcacgcttcaaaagcgcacgtctgccgcgctgttctcctcttcctcaggatccATGCGTCCC

CTGCGCCCCCGCGCCGCGCTGCTGGCGCTCCTGGCCTCGCTCCTGGCCGCGCCCC

CGGTGGCCCCGGCCGAGGCCCCGCACCTGGTGCATGTGGACGCGGCCCGCGCGC

TGTGGCCCCTGCGGCGCTTCTGGAGGAGCACAGGCTTCTGCCCCCCGCTGCCACA

CAGCCAGGCTGACCAGTACGTCCTCAGCTGGGACCAGCAGCTCAACCTCGCCTAT

GTGGGCGCCGTCCCTCACCGCGGCATCAAGCAGGTCCGGACCCACTGGCTGCTG

GAGCTTGTCACCACCAGGGGGTCCACTGGACGGGGCCTGAGCTACAACTTCACC

CACCTGGACGGGTACCTGGACCTTCTCAGGGAGAACCAGCTCCTCCCAGGGTTTG

AGCTGATGGGCAGCGCCTCGGGCCACTTCACTGACTTTGAGGACAAGCAGCAGG

TGTTTGAGTGGAAGGACTTGGTCTCCAGCCTGGCCAGGAGATACATCGGTAGGTA

CGGACTGGCGCATGTTTCCAAGTGGAACTTCGAGACGTGGAATGAGCCAGACCA

CCACGACTTTGACAACGTCTCCATGACCATGCAAGGCTTCCTGAACTACTACGAT

GCCTGCTCGGAGGGTCTGCGCGCCGCCAGCCCCGCCCTGCGGCTGGGAGGCCCC

GGCGACTCCTTCCACACCCCACCGCGATCCCCGCTGAGCTGGGGCCTCCTGCGCC

ACTGCCACGACGGTACCAACTTCTTCACTGGGGAGGCGGGCGTGCGGCTGGACT

ACATCTCCCTCCACAGGAAGGGTGCGCGCAGCTCCATCTCCATCCTGGAGCAGGA

GAAGGTCGTCGCGCAGCAGATCCGGCAGCTCTTCCCCAAGTTCGCGGACACCCCC

ATTTACAACGACGAGGCGGACCCGCTGGTGGGCTGGTCCCTGCCACAGCCGTGG

AGGGCGGACGTGACCTACGCGGCCATGGTGGTGAAGGTCATCGCGCAGCATCAG

AACCTGCTACTGGCCAACACCACCTCCGCCTTCCCCTACGCGCTCCTGAGCAACG
```

-continued

ACAATGCCTTCCTGAGCTACCACCCGCACCCCTTCGCGCAGCGCACGCTCACCGC

GCGCTTCCAGGTCAACAACACCCGCCCGCCGCACGTGCAGCTGTTGCGCAAGCC

GGTGCTCACGGCCATGGGGCTGCTGGCGCTGCTGGATGAGGAGCAGCTCTGGGC

CGAAGTGTCGCAGGCCGGGACCGTCCTGGACAGCAACCACACGGTGGGCGTCCT

GGCCAGCGCCCACCGCCCCCAGGGCCCGGCCGACGCCTGGCGCGCCGCGGTGCT

GATCTACGCGAGCGACGACACCCGCGCCCACCCCAACCGCAGCGTCGCGGTGAC

CCTGCGGCTGCGCGGGGTGCCCCCCGGCCCGGGCCTGGTCTACGTCACGCGCTAC

CTGGACAACGGGCTCTGCAGCCCCGACGGCGAGTGGCGGCGCCTGGGCCGGCCC

GTCTTCCCCACGGCAGAGCAGTTCCGGCGCATGCGCGCGGCTGAGGACCCGGTG

GCCGCGGCGCCCCGCCCCTTACCCGCCGGCGGCCGCCTGACCCTGCGCCCCGCGC

TGCGGCTGCCGTCGCTTTTGCTGGTGCACGTGTGTGCGCGCCCCGAGAAGCCGCC

CGGGCAGGTCACGCGGCTCCGCGCCCTGCCCCTGACCCAAGGGCAGCTGGTTCTG

GTCTGGTCGGATGAACACGTGGGCTCCAAGTGCCTGTGGACATACGAGATCCAG

TTCTCTCAGGACGGTAAGGCGTACACCCCGGTCAGCAGGAAGCCATCGACCTTCA

ACCTCTTTGTGTTCAGCCCAGACACAGGTGCTGTCTCTGGCTCCTACCGAGTTCG

AGCCCTGGACTACTGGGCCCGACCAGGCCCCTTCTCGGACCCTGTGCCGTACCTG

GAGGTCCCTGTGCCAAGAGGGCCCCCATCCCCGGGCAATCCATAGcTCGAGCCGC

TGAtcagcctcgactgtgccttctagttgccagccatctgttgtttgcccctcccccgtgccttccttgaccctggaaggtgccactccc actgtcctttcctaataaaatgaggaaattgcatcgcattgtctgagtaggtgtcattctattctggggggtggggtggggcaggacagc aagggggaggattgggaagacaatagcaggcatgctggggatgcggtgggctactagttgggctcactatgctgccgcccagtggg actttggaaatacaatgtgtcaactcttgacagggctctattttataggcttcttctctggaatcttcttcatcatcctcctgacaatcgatagg tacctggctgtcgtccatgctgtgtttgctttaaaagccaggacggtcacctttggggtggtgacaagtgtgatcacttgggtggtggctg tgtttgcgtctctcccaggaatcatctttaccagatctcaaaaagaaggtcttcattacacctgcagctctcattttccatacagtcagtatca attctggaagaatttccagacattaaagatagtcatcttggggctggtcctgccgctgcttgtcatggtcatctgctactcgggaatcctaa aaactctgcttcggtgtcgaaatgagaagaagaggcacagggctgtgaggcttatcttcaccatcatgattgtttattttctcttctgggctc
cctacaa Gaucher Disease: Strategy is to knock in GBA cDNA into Exon 3 of CCR5 safe harbor gene
to overexpress GBA enzyme under macrophage-specific CD68 promoter.
Left homology arm: 1-500 bp
CD68 promoter: 507-969 bp
GBA cDNA: 982-2589 bp
BgH Poly A: 2616-2823 bp
Right homology arm: 2841-3340 bp

TTTCATGAATTCCCCCAACAGAGCCAAGCTCTCCATCTAGTGGACAGGGAAGCTA

GCAGCAAACCTTCCCTTCACTACAAAACTTCATTGCTTGGCCAAAAAGAGAGTTA

ATTCAATGTAGACATCTATGTAGGCAATTAAAAACCTATTGATGTATAAAACAGT

TTGCATTCATGGAGGGCAACTAAATACATTCTAGGACTTTATAAAAGATCACTTT

TTATTTATGCACAGGGTGGAACAAGATGGATTATCAAGTGTCAAGTCCAATCTAT

GACATCAATTATTATACATCGGAGCCCTGCCAAAAAATCAATGTGAAGCAAATC

GCAGCCCGCCTCCTGCCTCCGCTCTACTCACTGGTGTTCATCTTTGGTTTTGTGGG

CAACATGCTGGTCATCCTCATCCTGATAAACTGCAAAAGGCTGAAGAGCATGACT

GACATCTACCTGCTCAACCTGGCCATCTCTGACCTGTTTTTCCTTCTTACTGTCCC

CTTCTctagaCTGTTCCCATAGCTACTTGCCACAACTGCCAAGCAAGTTTCGCTGAG

38. The donor template of embodiment 37, wherein the therapeutic protein is iduronidase.
39. The donor template of embodiment 38, wherein the template comprises the sequence shown as SEQ ID NO: 6 or SEQ ID NO: 7.
40. The donor template of embodiment 37, wherein the therapeutic protein is glucocerebrosidase.
41. The donor template of embodiment 40, wherein the template comprises the sequence shown as SEQ ID NO: 8.
42. The donor template of embodiment 37, wherein the therapeutic protein is galactocerebrosidase.
43. An HSPC comprising the sgRNA of any one of embodiments 32 to 36, or a homologous donor template of any one of embodiments 37 to 42.
44. A genetically modified HSPC comprising an integrated transgene at the CCR5 locus, wherein the integrated transgene comprises a coding sequence for iduronidase, glucocerebrosidase, or galactocerebrosidase.
45. The genetically modified HSPC of embodiment 44, wherein the HSPC was modified using the method of any one of embodiments 1 to 26.

What is claimed is:

1. A method of genetically modifying a cell from a subject with a lysosomal storage disorder (LSD), the method comprising:

introducing into a cell isolated from the subject a single guide RNA (sgRNA) targeting the CCR5 locus, an RNA-guided nuclease, and a homologous donor template comprising a transgene encoding a therapeutic protein that is absent or deficient in the subject, wherein:

the sgRNA binds to the nuclease and directs it to a target sequence at the CCR5 locus in the genome of the cell whereupon the nuclease cleaves the CCR5 locus at the target sequence, wherein:

the homologous donor template comprises a sequence having 96% or greater identity to SEQ ID NO: 7 and the transgene is integrated into the genome by homology directed recombination (HDR) at the site of the cleaved CCR5 locus, and wherein the integrated transgene directs the expression of the therapeutic protein in the cell.

2. The method of claim 1, wherein the sgRNA comprises chemical modifications at one or more nucleotides.

3. The method of claim 1, wherein the target sequence of the sgRNA comprises the sequence of SEQ ID NO:3 or SEQ ID NO:4.

4. The method of claim 3, wherein the sgRNA comprises a sequence having 95% or greater identity to SEQ ID NO:5.

5. The method of claim 1, wherein the RNA-guided nuclease is Cas9.

6. The method of claim 1, wherein the sgRNA and the RNA-guided nuclease are introduced into the cell as a ribonucleoprotein (RNP).

7. The method of claim 1, wherein the homologous donor template is introduced into the cell using a recombinant adeno-associated virus (rAAV) vector.

8. The method of claim 1, wherein the LSD is mucopolysaccharidosis type 1, and the therapeutic protein is iduronidase.

9. The method of claim 8, wherein the cell is a CD34+ hematopoietic stem and progenitor cell (HSPC).

10. The method of claim 1, wherein the homologous donor template comprises a sequence having 97% or greater identity to SEQ ID NO: 7.

11. The method of claim 1, wherein the homologous donor template comprises a sequence having 98% or greater identity to SEQ ID NO: 7.

12. The method of claim 1, wherein the homologous donor template comprises a sequence having 99% or greater identity to SEQ ID NO: 7.

13. The method of claim 1, wherein the homologous donor template comprises the sequence of SEQ ID NO: 7.

* * * * *